US009393309B2

(12) United States Patent
Nishikawa et al.

(10) Patent No.: US 9,393,309 B2
(45) Date of Patent: Jul. 19, 2016

(54) SELF-GELATINIZABLE NUCLEIC ACID

(75) Inventors: Makiya Nishikawa, Kyoto (JP); Yuki Takahashi, Kyoto (JP); Yoshinobu Takakura, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/112,648

(22) PCT Filed: Apr. 19, 2012

(86) PCT No.: PCT/JP2012/060613
§ 371 (c)(1),
(2), (4) Date: Oct. 18, 2013

(87) PCT Pub. No.: WO2012/144560
PCT Pub. Date: Oct. 26, 2012

(65) Prior Publication Data
US 2014/0079738 A1 Mar. 20, 2014

(30) Foreign Application Priority Data

Apr. 19, 2011 (JP) .................................. 2011-093082

(51) Int. Cl.
| *C07H 19/00* | (2006.01) |
| *C07H 21/00* | (2006.01) |
| *C12Q 1/68* | (2006.01) |
| *A61K 45/00* | (2006.01) |
| *A61K 47/26* | (2006.01) |
| *A61K 31/7088* | (2006.01) |
| *A61K 39/39* | (2006.01) |
| *A61L 27/52* | (2006.01) |
| *A61L 27/22* | (2006.01) |
| *A61K 9/00* | (2006.01) |
| *A61K 9/06* | (2006.01) |
| *A61K 47/34* | (2006.01) |

(52) U.S. Cl.
CPC ............... *A61K 47/26* (2013.01); *A61K 9/0019* (2013.01); *A61K 9/0024* (2013.01); *A61K 9/06* (2013.01); *A61K 31/7088* (2013.01); *A61K 39/39* (2013.01); *A61K 47/34* (2013.01); *A61L 27/227* (2013.01); *A61L 27/52* (2013.01)

(58) Field of Classification Search
CPC .......... C07H 19/00; C07H 21/00; C12Q 1/68; A61K 45/00
USPC .......................... 536/22.1; 435/6.1; 424/280.1
See application file for complete search history.

(56) References Cited

U.S. PATENT DOCUMENTS

| 7,060,814 B2 * | 6/2006 | Usui et al. ..................... 536/24.3 |
| 2007/0117177 A1 * | 5/2007 | Luo et al. ..................... 435/68.1 |
| 2009/0118218 A1 | 5/2009 | Stopek | |

FOREIGN PATENT DOCUMENTS

| JP | 2002-018270 | 1/2002 |
| JP | 2005-239860 | 9/2005 |

OTHER PUBLICATIONS

Data sheet melting temperature rule [Down loaded from the internet http://parts.igem.org/], printed on Feb. 21, 2015, pp. 1 and 2.*
Data sheet-1 instant SEQ ID No. 2 with CpGXb of Nishikawa Blast search results [down loaded from the internet http://blast.ncbi.nlm.nih.gov/Blast.cgi], printed on Dec. 15, 2015, p. 1.*
Data sheet-2 instant SEQ ID No. 4 with CpGXa of Nishikawa Blast search results [down loaded from the internet http://blast.ncbi.nlm.nih.gov/Blast.cgi], printed on Dec. 15, 2015, p. 1.*
Data sheet-3 instant SEQ ID No. 5 with CpGXc of Nishikawa Blast search results [down loaded from the internet http://blast.ncbi.nlm.nih.gov/Blast.cgi], printed on Dec. 15, 2015, p. 1.*
Data sheet-4 instant SEQ ID No. 6 with CpGXd of Nishikawa Blast search results [down loaded from the internet http://blast.ncbi.nlm.nih.gov/Blast.cgi], printed on Dec. 15, 2015, p. 1.*
International Search Report issued in International corresponding (PCT) Application No. PCT/JP2012/060613.
Soong Ho Um et al.; "Enzyme-catalysed assembly of DNA hydrogel"; Nature Materials; vol. 5; 2006; pp. 797-801.
Diana Costa et al.; "Responsive Polymer Gels: Double-Stranded versus Single-Stranded DNA"; J. Phys. Chem. B.; vol. 111, No. 37; 2007; pp. 10886-10896.
Enjun Cheng et al.; "A pH-Triggered, Fast-Responding DNA Hydrogel**"; Angew. Chem. Int. Ed.; vol. 48; 2009; pp. 7660-7663.
Yongzheng Xing et al.; "Self-Assembled DNA Hydrogels with Designable Thermal and Enzymatic Responsiveness"; Advanced Materials; vol. 23, No. 9; 2011; pp. 1117-1121.
Makiya Nishikawa et al.; "Biodegradable CpG DNA hydrogels for sustained delivery of doxorubicin and immunostimulatory signals in tumor-bearing mice"; Biomaterials; vol. 32, No. 2; 2011; pp. 488-494.
Kota Mori et al.; "Development of oligonucleotide-based nano-sized DDS"; Drug Delivery System; vol. 25, No. 6; 2010; pp. 573-578 (with English language abstract).
Extended European Search Report issued Oct. 27, 2014 in corresponding European Application No. 12774101.5.
Translation of the International Preliminary Report on Patentability issued Nov. 14, 2013 in corresponding International Application No. PCT/JP2012/060613.

* cited by examiner

*Primary Examiner* — Narayan Bhat
(74) *Attorney, Agent, or Firm* — Wenderoth, Lind & Ponack, L.L.P.

(57) ABSTRACT

A method for preparing a hydrogel composed substantially only of nucleic acids. Further, a nucleic acid sol-like composition for producing a nucleic acid gel without requiring the use of any nucleic acid ligase, wherein the composition comprises at least two nucleic acid monomers which are partly complementary to each other and are independently selected from the group consisting of a nucleic acid, a nucleic acid derivative, a modified nucleic acid, a compound capable of binding to a nucleic acid in a complementary manner and a mixture thereof, one of the nucleic acid monomers has a moiety that constitutes a cohesive protruding end and a complementary nucleotide sequence moiety that can bind to at least one of the other nucleic acid monomers to form a double strand, and the composition contains no nucleic acid ligase. Still further, a nucleic acid gel produced using the sol-like composition.

5 Claims, 24 Drawing Sheets

Fig. 4
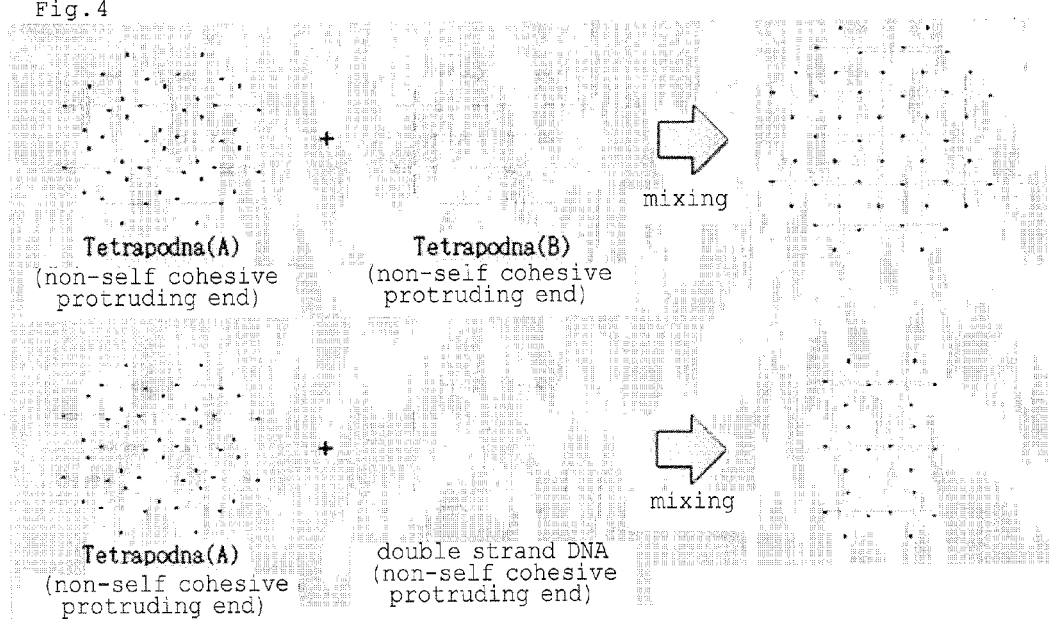
Fig. 5
gel encapsulating various substances
protocol
Tetrapodna (4-18-18)
0.5 mM DNA×4
5mM NaCl
 encapsulated substance,
↓ concentration of NaCl
150 mM NaCl
doxorubicin
egg albumin
RAW264.7 cell
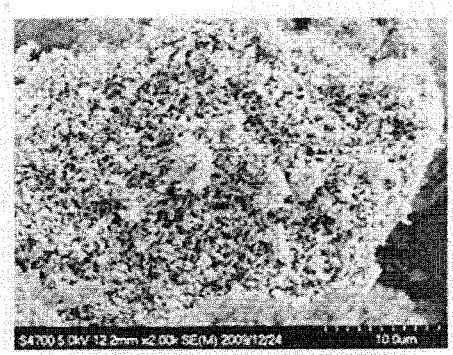

comparison between Y-type monomer and dendrimer-like DNA produced by linking Y-type monomers sol administration → gelation in living body

Fig.9

| Tetrapodna | (immunologically inactive) | Tetrapodna | (immunologically active, immunostimulation activity) |

AGCT AGGCACCGTAGTCAATCG CCGATGTGTCCAAAGCCT
AGCT AGGCTTTGGACACATCGG TGCTCCTACCGTACTCCT
AGCT AGGAGTACCGTAGGAGCA GTTTCGGCATGTCCACCT
AGCT AGGTGGACATGCCGAAAC CGATTGACTACGGTGCCT

ACGT TCGCTGACGTTGCAGACA TCACGTTGACGCTGTCGA
ACGT TCGACAGCGTCAACGTGA AACGTGAAGCGTCTGCGA
ACGT TCGCAGACGCTTCACGTT GCAGACAGACGTTGACGA
ACGT TCGTCAACGTCTGTCTGC TGTCTGCAACGTCAGCGA

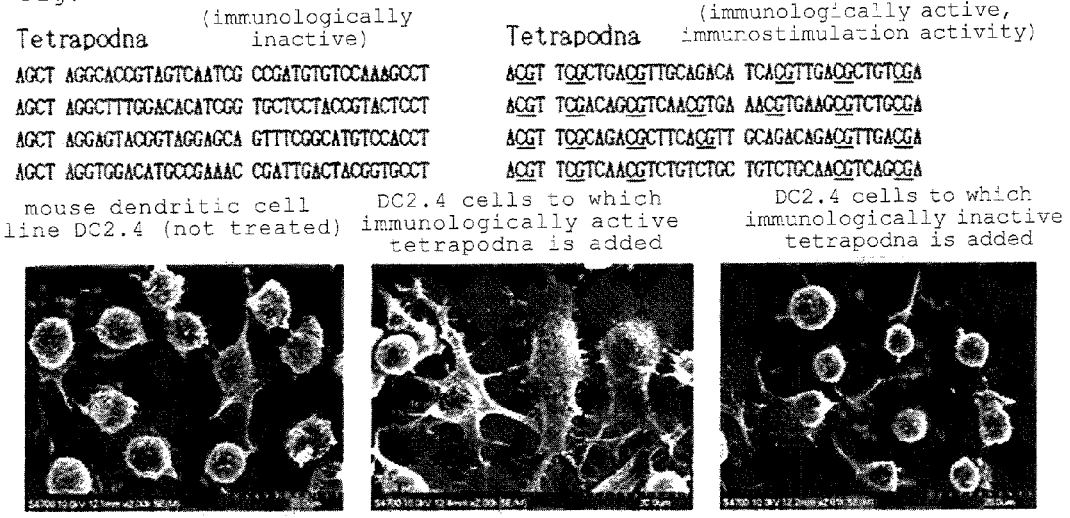

mouse dendritic cell line DC2.4 (not treated) | DC2.4 cells to which immunologically active tetrapodna is added | DC2.4 cells to which immunologically inactive tetrapodna is added

Fig.10

| tri01 | ACGT TCGTCAACGTCTGTGCTC TCACGTTGACGCTGTCGA |
| tri02,tet02,pen02,hex02 | ACGT TCGACAGCGTCAACGTGA AACGTGAAGCGTCTGCGA |
| tri03,pen03,hex03 | ACGT TCGCAGACGCTTCACGTT GAGCACAGACGTTGACGA |
| tet01,pen01,hex01 | ACGT TCGCTGACGTTGCAGACA TCACGTTGACGCTGTCGA |
| tet03 | ACGT TCGCAGACGCTTCACGTT GCAGACAGACGTTGACGA |
| tet04 | ACGT TCGTCAACGTCTGTCTGC TGTCTGCAACGTCAGCGA |
| pen04,hex04 | ACGT TCGTCAACGTCTGTGCTC GCAGCGTCTTAACGTCGA |
| pen05 | ACGT TCGACGTTAAGACGCTGC TGTCTGCAACGTCAGCGA |
| hex05 | ACGT TCGACGTTAAGACGCTGC AGACGTTCAGGACTACGA |
| hex06 | ACGT TCGTAGTCCTGAACGTCT TGTCTGCAACGTCAGCGA |
| 6-17-17 tet01 | AACGTT TACGCACGACATCAGCG TCTGGACGCTTCGTCGA |
| 6-17-17 tet02 | AACGTT TCGACGAAGCGTCCAGA TCTCGTCAACGCTGCGA |
| 6-17-17 tet03 | AACGTT TCGCAGCGTTGACGAGA CAGACGCTGTGACGCTA |
| 6-17-17 tet04 | AACGTT TAGCGTCACAGCGTCTG CGCTGATGTCGTGCGTA |
| 8-16-16 tet01 | ACGTACGT TAGCACGACATCAGCG TCTGACGCTTCGTCGA |
| 8-16-16 tet02 | ACGTACGT TCGACGAAGCGTCAGA TCTCGTCAACGCTGCA |
| 8-16-16 tet03 | ACGTACGT TGCAGCGTTGACGAGA CAGACGCTTGACGCTA |
| 8-16-16 tet04 | ACGTACGT TAGCGTCAAGCGTCTG CGCTGATGTCGTGCTA |
| 10-15-15 tet01 | ACGTTAACGT TGCACGACATCAGCG TCTGACGCTCGTCGA |
| 10-15-15 tet02 | ACGTTAACGT TCGACGAGCGTCAGA TCTCGCAACGCTGCA |
| 10-15-15 tet03 | ACGTTAACGT TGCAGCGTTGCGAGA CAGACGCTTGACGCA |
| 10-15-15 tet04 | ACGTTAACGT TGCGTCAAGCGTCTG CGCTGATGTCGTGCA |
| 12-14-14 tet01 | ACGTCATGACGT TGCACGACATCACGT TGACGCTCGTCGA |
| 12-14-14 tet02 | ACGTCATGACGT TCGACGAGCGTCAAT CTCGCAACGTGCA |
| 12-14-14 tet03 | ACGTCATGACGT TGCACGTTGCGAGAC AGACGCTTGACGA |
| 12-14-14 tet04 | ACGTCATGACGT TCGTCAAGCGTCTGC GTGATGTCGTGCA | boldface: cohesive end

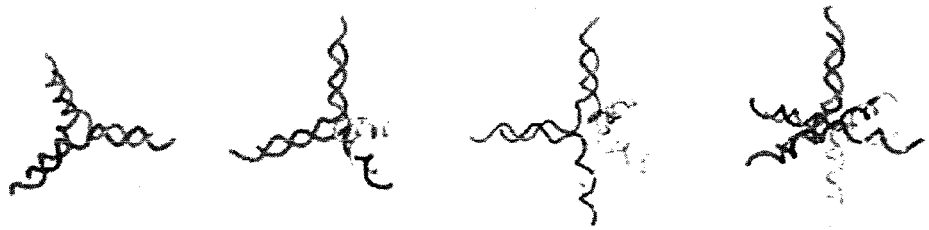

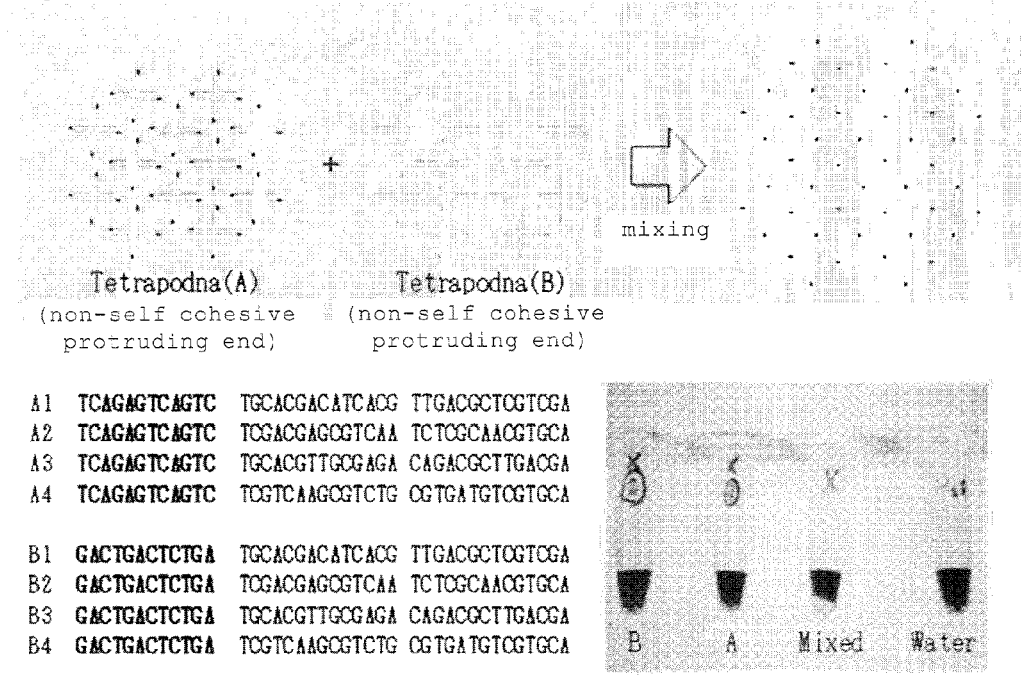

enhancement of egg albumin (OVA) immune response

Fig.15
Estimated steric structure
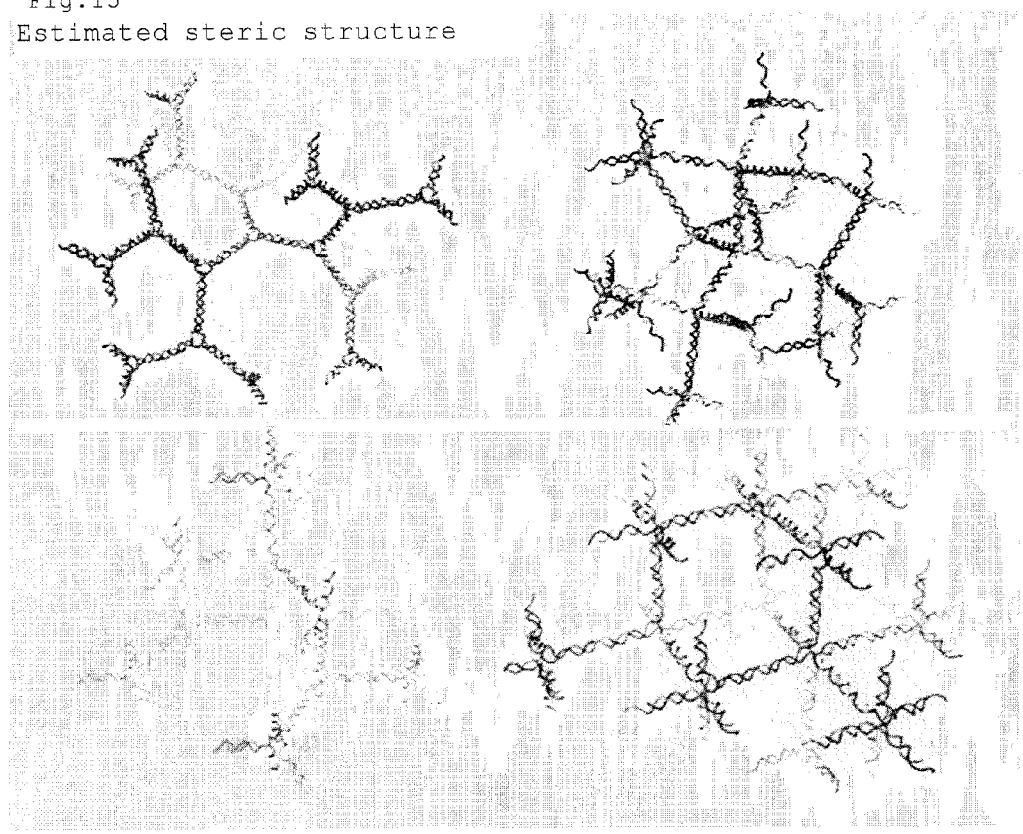
Fig.16
difference in structure
Tripodna (4-18-18)
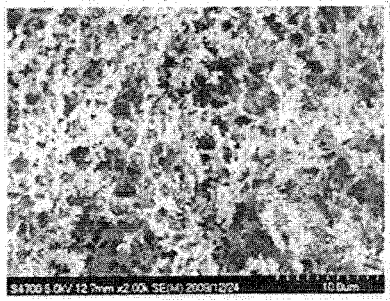
Hexapodna (4-18-18)
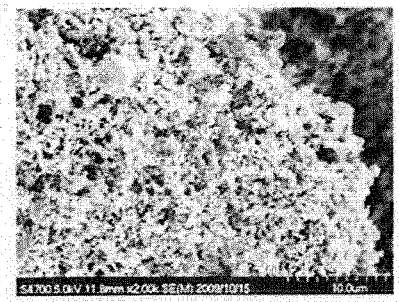
Tetrapodna (4-18-18)
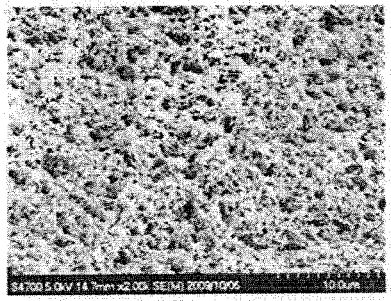
Tetrapodna (12-14-14)

release control of encapsulated egg albumin (OVA)

utilization of nucleic acid having modifying group,
utilization of cholesterol-modified DNA cell uptake by cholesterol modified DNA, increase of tissue transferability sol administration → gelation in living body Fig.21
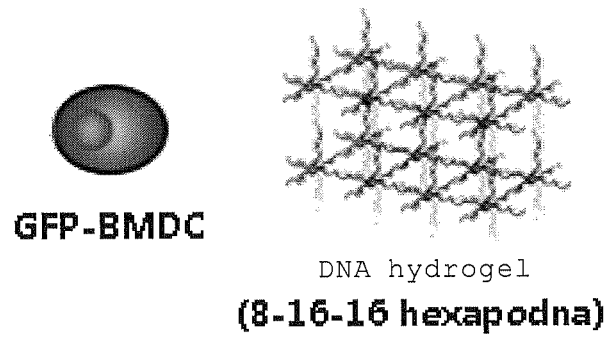
GFP-BMDC    DNA hydrogel
            (8-16-16 hexapodna)
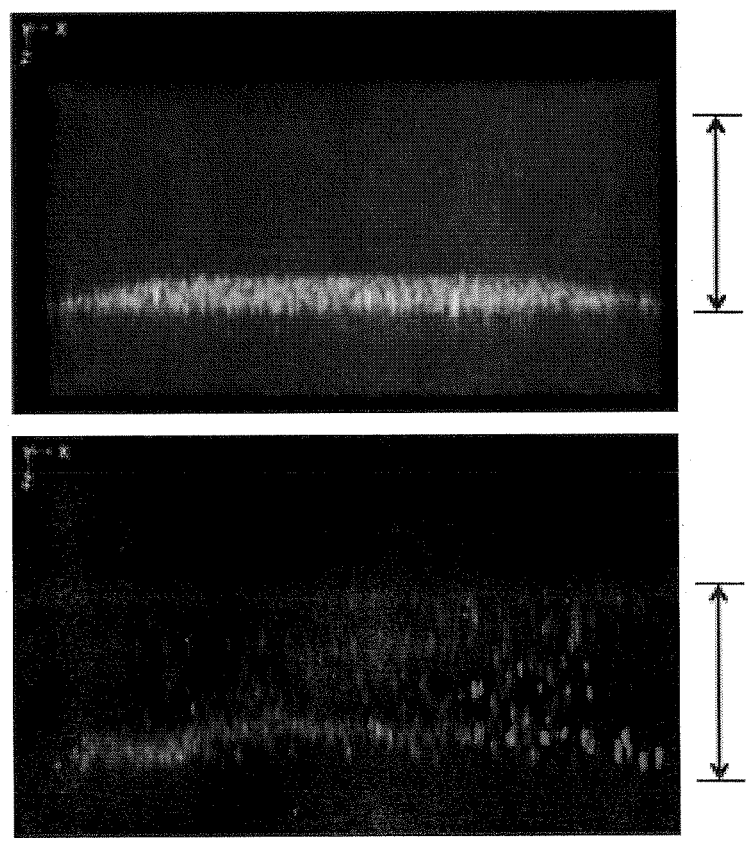

Fig.24
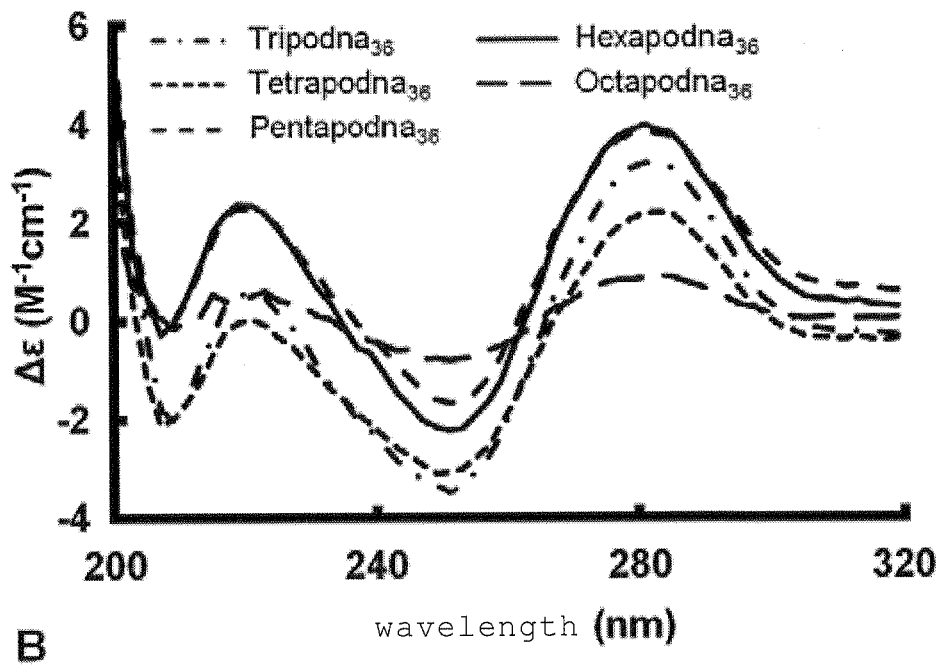
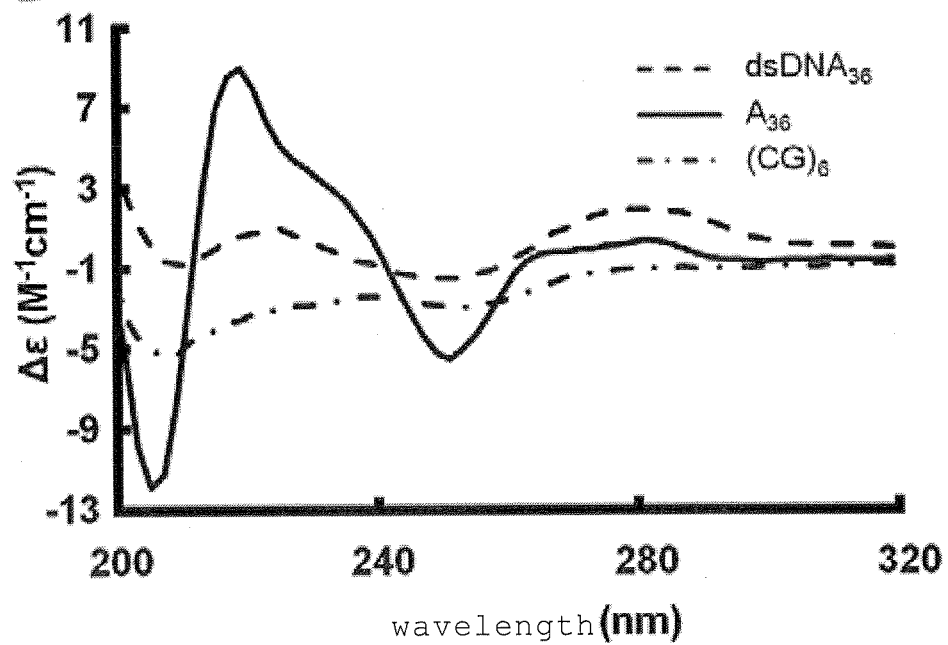

Fig. 25
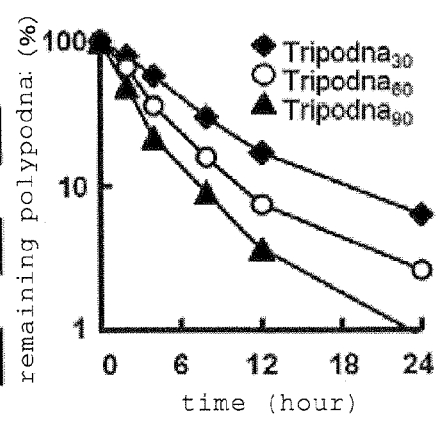
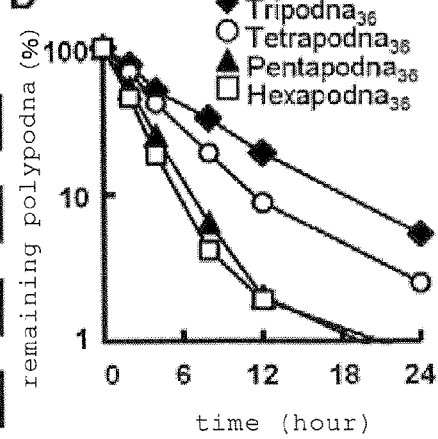

Fig. 31
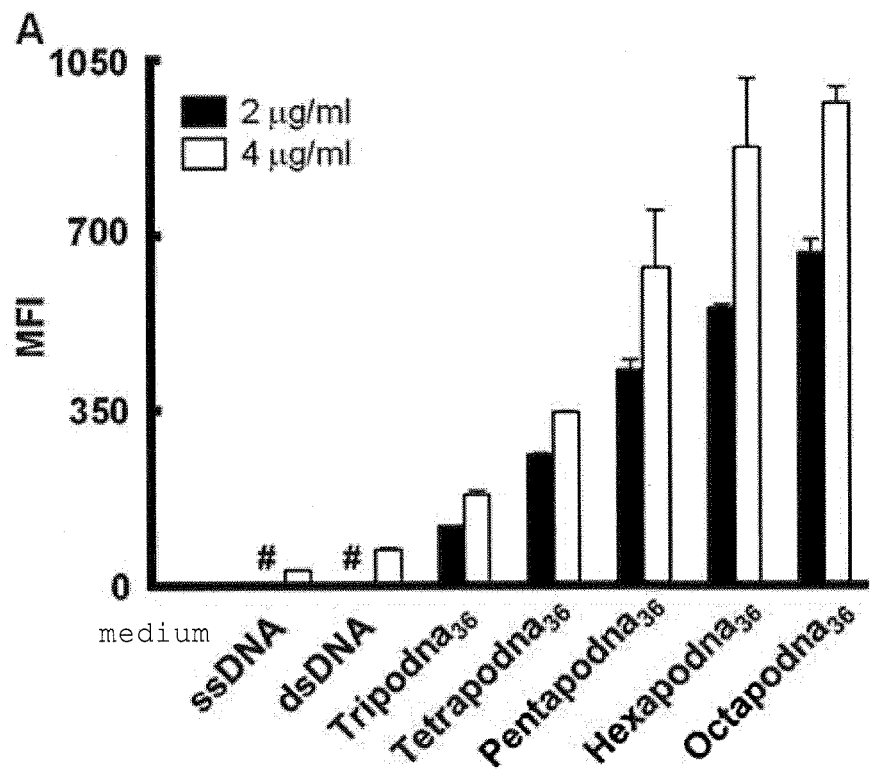
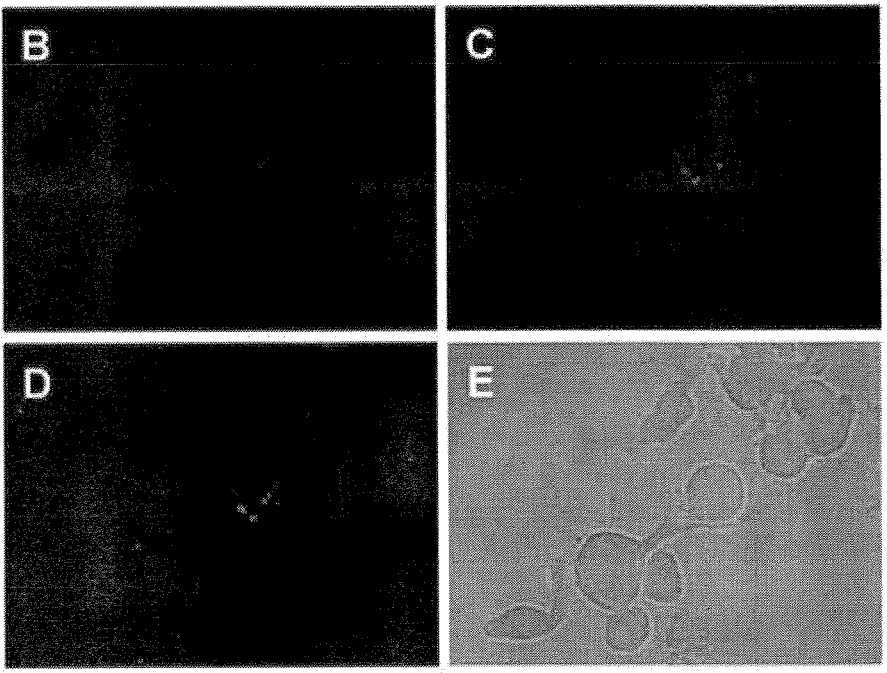

SELF-GELATINIZABLE NUCLEIC ACID

TECHNICAL FIELD

The present invention relates to a self-gelatinizable nucleic acid. Specifically, the present invention relates to a method for preparing a hydrogel composed only substantially of nucleic acid without using a nucleic acid linking enzyme such as ligase.

BACKGROUND ART

A trial for producing a gel by using nucleic acid, in particular, DNA has been reported (Non-patent Document 1). In the method disclosed in Non-patent Document 1, the ends of a DNA monomer are subjected to covalent linkage by using a DNA ligase. More specifically, Non-patent Document 1 reports that DNA chains each having a complementary sequence at the ends are synthesized; X-type DNA, Y-type DNA, and T-type DNA are produced by using a T4 ligase; and a hydrogel is produced by using such DNAs. However, since the gel produced by using the DNA disclosed in Non-patent Document 1 includes a remaining enzyme (DNA ligase) which is used for gelation, there have been problems in terms of safety and antigenicity.

Furthermore, the method disclosed in Non-patent Document 1 needs an enzyme reaction for gelation, and thus when a gel is administered to a living body, the gel is produced outside the living body in advance, and needs to be administered in its original form. This is a large limit to administration. Furthermore, the gelation reaction disclosed in Cited Document 1 is reaction using an enzyme, and thus in order to enclose a relatively large substance into a gel, it is necessary to add a substance to be enclosed at the time of gelation, that is, a ligation reaction. However, this has a high risk for damaging a function of the substance to be enclosed. Furthermore, with the gel prepared by using a ligase, sufficiently high viscoelasticity can not be obtained.

In addition to this, a large number of trials for formation of a hydrogel including DNA as a constituent element have been carried out. There have been many reports of formation using chemical cross-linking, formation depending upon heat and pH and the like (Non-patent Documents 2, 3 and Patent Document 1).

For example, Non-patent Document 2 reports that DNA extracted from salmon testis is chemically cross-linked (with the use of ethylene glycol diglycidyl ether), 1 M NaOH and TEMED are then added thereto, and the mixture is heated for about two hours (50° C.) to obtain a gel. In such a method, however, an organic compound is used which is concerned about safety to a living body in addition to nucleic acid, and therefore the safety in administration of the gel to a living body is concerned. Furthermore, the gelation needs heating, and therefore a substance that is easily denatured cannot be contained.

Furthermore, Non-patent Document 3 relates to production of pH-dependent Y-type DNA. The method utilizes a change of a state of a DNA molecule dependent upon pH change. This method permits gelation by adding HCl into a DNA solution so as to be acidic. Substances that have once been gelled can be returned to be a state of solution by adding NaOH. However, in order to maintain a gel state, the environment is required to be kept to be acidic, thus making the gel to be unstable with respect to the surrounding environment.

Patent Document 1 discloses a method for providing a synthesis hydrogel, which does not include a chemical reaction or a polymerization reaction, and which can simply and rapidly produce a hydrogel having sufficient strength around the body temperature (37° C.) in a physiological condition. The gel obtained by the method is a hydrogel obtained by mixing a water-soluble polymer such as polysaccharide and nucleic acid with each other, and permits temperature-dependent gel-sol transition. However, the gel contains a large amount of polysaccharide, and therefore it cannot be said that the gel is a hydrogel composed of nucleic acid.

Meanwhile, various hydrogel formulations have been developed utilizing gelatin, a synthesized polymer, or the like. Also in the case of the gels prepared therefrom, the gelation is carried out before administration, and systems to be gelled after administration are few. Also, injectable gels are reported, but they are gels having a submicron to micron size capable of passing through an injector needle. Therefore, in a case of administration by injection or the like, minute gels are used and, in such a case, gel properties such as sustained release properties are largely damaged.

Furthermore, hydrogels using sol-gel transition by temperatures have been reported in plural documents (for example, Patent Document 2). However, compounds to be used partially utilize chemical modification, and therefore the gels are not gels composed of pure natural materials such as nucleic acid.

It should be noted that many trials using CpG DNA as an adjuvant have been made. Reports of enhancement in activating ability by cholesterol modification or phosphorothioation have been made. However, in such cases, even when the adjuvant (CpG DNA) and an antigen are administrated simultaneously, there is a concern that behaviors thereof in a living body may be carried out separately. Furthermore, in the case of phosphorothioate-type DNA, there is a problem that tissue disorder may occur by high protein binding properties.

PRIOR ART DOCUMENTS

Patent Documents

Patent Document 1: JP-A-2002-18270
Patent Document 2: JP-A-2005-239860

Non-Patent Documents

Non-patent Document 1: Nat. Mater. 5: 797-801, 2006
Non-patent Document 2: J Phys Chem B. 2007 Sep. 20; 111(37): 10886-96
Non-patent Document 3: Angew Chem Int Ed Engl. 2009; 48(41): 7660-3

SUMMARY OF INVENTION

Problems to be Solved by Invention

A controlled release system for carrying out sustained-releasing of a physiologically active substance such as a hydrogel is effective in obtaining a long-lasting therapeutic effect and reduction of an adverse effect. An object of the present invention is to provide a method of preparing a hydrogel composed only substantially of nucleic acid and having high viscoelasticity as compared with that of gels using ligase by preparing nucleic acid units having various structures with a nucleic acid monomer such as DNA or RNA as a basic unit, and linking the nucleic acid units without using an enzyme such as a DNA ligase.

Solutions to the Problems

The present inventors have found that it is possible to provide a hydrogel composed only substantially of nucleic acid and having high viscoelasticity by adjusting the salt concentration and the nucleic acid concentration, and the number of bases at protruding ends in the nucleic acid unit. That is, the present invention provides a method for preparing a hydrogel composed only substantially of nucleic acid and having high viscoelasticity without using enzymes such as a ligase.

The conventional method employs a method of binding oligonucleotides each having an end to which a phosphoric acid group is bound with a DNA ligase. On the contrary, the method of the present invention enables a hydrogel to be prepared without enzyme reaction by adjusting the number of bases of the protruding end, the salt concentration, the nucleic acid concentration, and the like. According to the method of the present invention, an enzyme is not used. In addition to this, heat, pH change or the like is not utilized. Therefore, administration in a sol state is possible. After administration, gelation in a living body can be carried out. Furthermore, two or more kinds of nucleic acid monomers are designed, so that a gelation system by mixing can be constructed. In this case, the gelation does not need enzymes, heat or the like, so that chemically and physically unstable substances can be internally enclosed.

That is, the present invention provides the followings in a first aspect.

(1-1) A nucleic acid sol-like composition for producing a nucleic acid gel without using a nucleic acid linking enzyme, the composition comprising two or more nucleic acid monomers which are partly complementary to each other and which are selected from the group consisting of nucleic acid, a nucleic acid derivative, a modified nucleic acid, a compound binding to nucleic acid in a complementary manner, and a mixture thereof, wherein one nucleic acid monomer has a moiety which constitutes a cohesive protruding end and a complementary base sequence moiety that can form a double strand with one or more other nucleic acid monomers, and the composition does not contain a nucleic acid linking enzyme.

(1-2) The sol-like composition according to (1-1), for producing a gel in a living body.

(1-3) The sol-like composition according to (1-1) or (1-2), wherein the nucleic acid monomer has a sequence structure which binds to the complementary base sequence moiety in a complementary manner, and which is complementary to such a degree that the cohesive protruding end forms a double strand sequence showing a melting temperature that is equal to or higher than the body temperature in a physiological condition.

(1-4) A method for producing a nucleic acid gel without using a nucleic acid linking enzyme by increasing a nucleic acid concentration and/or a salt concentration of the nucleic acid sol-like composition according to any one of (1-1) to (1-3).

(1-5) A kit for producing a nucleic acid gel which does not contain a nucleic acid linking enzyme without using the nucleic acid linking enzyme, the kit independently comprising:

a first sol-like composition which includes a first nucleic acid monomer according to (1-1) and which does not contain the nucleic acid linking enzyme; and a second sol-like composition which includes a second nucleic acid monomer according to (1-1) and which does not contain the nucleic acid linking enzyme, wherein a cohesive protruding end in the first nucleic acid monomer includes a first sequence;

a cohesive protruding end in the second nucleic acid monomer includes a second sequence; and the first sequence and the second sequence are complementary to each other to such a degree as to form a double strand sequence which shows a melting temperature that is equal to or higher than the body temperature in a physiological condition.

(1-6) A method for producing a nucleic acid gel which does not contain a nucleic acid linking enzyme, the method comprising forming a gel by mixing the first sol-like composition and the second sol-like composition in the kit according to (1-5).

(1-7) A kit for producing a nucleic acid gel which does not contain a nucleic acid linking enzyme without using the nucleic acid linking enzyme, the kit independently comprising:

a first sol-like composition which includes a nucleic acid monomer according to (1-1) and which does not contain the nucleic acid linking enzyme; and a second sol-like composition which contains double strand nucleic acid having cohesive single strand protruding ends at both ends and which does not contain the nucleic acid linking enzyme, wherein a cohesive protruding end in the first nucleic acid monomer includes a first sequence;

the protruding ends at both ends of the double strand nucleic acid include a second sequence; and the first sequence and the second sequence are complementary to each other to such a degree as to form a double strand sequence which shows a melting temperature that is equal to or higher than the body temperature in a physiological condition.

(1-8) A method for producing a nucleic acid gel which does not contain a nucleic acid linking enzyme, the method comprising forming gel by mixing the first sol-like composition and the second sol-like composition in the kit according to (1-7).

(1-9) A nucleic acid gel produced by the method according to any one of (1-4), (1-6) and (1-8), which does not contain a nucleic acid linking enzyme.

(1-10) A method for producing a nucleic acid gel which encloses an encapsulated substance and which does not contain a nucleic acid linking enzyme, the method comprising adding the encapsulated substance to be enclosed in a gel before formation of the gel into a sol-like composition, in the method according to any one of (1-4), (1-6) and (1-8).

(1-11) The method according to (1-10), wherein the encapsulated substance is selected from a low-molecular compound, a protein, and a cell.

(1-12) A nucleic acid gel produced by the method according to (1-10) or (1-11), which contains an encapsulated substance and which does not contain a nucleic acid linking enzyme.

Furthermore, the present invention also provides the followings.

(1-13): The sol-like composition according to (1-1) or (1-2), wherein the nucleic acid monomer binds to a complementary base sequence moiety in a complementary manner, and the cohesive protruding end includes a palindrome sequence structure.

The present invention further provides the followings in a second aspect.

(2-1): A sol-like composition for producing a nucleic acid gel which does not contain a nucleic acid linking enzyme, the composition containing a mixture of two or more oligonucleotides composed of a cohesive protruding end moiety and a complementary base sequence moiety in the composition at a nucleic acid concentration of 0.3 mM+1.6/x (the number of bases in the protruding end moiety) mM or less, not containing a nucleic acid linking enzyme, and having a salt concentration of 80 mM/x (the number of bases in the protruding end moiety) or less in terms of a NaCl concentration:

[wherein the cohesive protruding end moiety is a single strand nucleic acid moiety having 4 to 12 nucleotide length and being complementary to a cohesive protruding end moiety in at least another oligonucleotide to such a degree as to form a double strand sequence showing a melting temperature that is equal to or higher than the body temperature in a physiological condition, and the complementary base sequence moiety that binds to the other oligonucleotide in a complementary manner has 8 to 45 nucleotide length and is complementary to the complementary base sequence moiety in the other oligonucleotide to such a degree as to form a double strand sequence showing a melting temperature that is equal to or higher than the body temperature in a physiological condition].

(2-2) The sol-like composition according to (2-1), for producing a gel in a living body.

(2-3): The sol-like composition according to (2-1), wherein the cohesive protruding end includes a palindrome sequence structure.

(2-4): A method for producing a nucleic acid gel which does not contain a nucleic acid linking enzyme, the method comprising forming a gel by increasing the nucleic acid concentration of the sol-like composition according to (2-3) to 3.2/x (the number of bases in the protruding end moiety) mM or more and increasing the salt concentration to 640 mM/x (the number of bases in the protruding end moiety)–60 mM or more in terms of a NaCl concentration, respectively.

(2-5): A kit for producing a nucleic acid gel which does not contain a nucleic acid linking enzyme, the kit independently comprising:

a first sol-like composition which contains the mixture of oligonucleotides according to (2-1) and which does not contain a nucleic acid linking enzyme; and a second sol-like composition which contains the mixture of oligonucleotides according to (2-1) and which does not contain a nucleic acid linking enzyme, wherein a cohesive protruding end moiety of the first oligonucleotide includes a first sequence;

a cohesive protruding end moiety of the second oligonucleotide includes a second sequence; and the first sequence and the second sequence are complementary to each other to such a degree as to form a double strand sequence showing a melting temperature that is equal to or higher than the body temperature in a physiological condition.

(2-6): A method for producing a nucleic acid gel which does not contain a nucleic acid linking enzyme, the method comprising forming a gel by mixing the first sol-like composition and the second sol-like composition in the kit according to (2-5) in the condition in which the nucleic acid concentration is adjusted to 3.2/x (the number of bases in the protruding end moiety) mM or more and the salt concentration is adjusted to 640 mM/x (the number of bases in the protruding end moiety)–60 mM or more in terms of a NaCl concentration.

(2-7): A kit for producing a nucleic acid gel which does not contain a nucleic acid linking enzyme, the kit independently comprising:

a first sol-like composition which contains the mixture of oligonucleotides according to (2-1) and which does not contain a nucleic acid linking enzyme; and a second sol-like composition which does not contain a nucleic acid linking enzyme, and which contains nucleic acid having cohesive single strand protruding end moieties at both ends, and having a double strand complementary base sequence moiety interposed therebetween;

[in the second sol-like composition, the protruding end moiety has 4 to 12 nucleotide length and is a single strand nucleic acid moiety which is complementary to a cohesive protruding end moiety in the oligonucleotide in the first sol-like composition to such a degree as to form a double strand sequence showing a melting temperature that is equal to or higher than the body temperature in a physiological condition; and the complementary base sequence moiety has 8 to 45 nucleotide length and is a double strand nucleic acid moiety which is complementary to a complementary base sequence moiety in the oligonucleotide in the first sol-like composition to such a degree as to form a double strand sequence showing a melting temperature that is equal to or higher than the body temperature in a physiological condition], wherein a cohesive protruding end moiety of the oligonucleotide in the first sol-like composition includes a first sequence;

the protruding end moieties at both ends of the complementary base sequence moiety made of the double strand includes a second sequence; and the first sequence and the second sequence are complementary to each other to such a degree as to form a double strand sequence showing a melting temperature that is equal to or higher than the body temperature in a physiological condition.

(2-8): A method for producing a nucleic acid gel which does not contain a nucleic acid linking enzyme, the method comprising forming a gel by mixing the first sol-like composition and the second sol-like composition in the kit according to (2-7) in the condition in which the nucleic acid concentration is adjusted to 3.2/x (the number of bases in the protruding end moiety) mM or more and the salt concentration is adjusted to 640 mM/x (the number of bases in the protruding end moiety)–60 mM or more in terms of a NaCl concentration.

(2-9) A nucleic acid gel produced by the method according to any one of (2-4), (2-6) and (2-8), which does not contain a nucleic acid linking enzyme.

(2-10) A method for producing a nucleic acid gel which encloses an encapsulated substance and which does not contain a nucleic acid linking enzyme, the method comprising adding the encapsulated substance to be enclosed in a gel before formation of the gel into a sol-like composition, in the method according to any one of (2-4), (2-6) and (2-8).

(2-11) The method according to (2-10), wherein the encapsulated substance is selected from a low-molecular compound, a protein, and a cell.

(2-12) A nucleic acid gel produced by the method according to (2-10) or (2-11), which contains an encapsulated substance and which does not contain a nucleic acid linking enzyme.

(3-1): The nucleic acid sol-like composition, method, kit, or nucleic acid gel according to any one of (1-12) and (2-12), wherein the nucleic acid monomer includes a CpG motif.

(3-2): The nucleic acid sol-like composition, method, kit, or nucleic acid gel according to any one of (1-12), (2-12) and (3-1), wherein the number of kinds of the nucleic acid monomers is 3 to 8.

(3-3): The sol-like composition for producing an immunological adjuvant according to any one of (1-1) to (1-3) and (2-1) to (2-3), wherein the nucleic acid monomer includes a CpG motif.

(3-4): An immunological adjuvant comprising the nucleic acid gel according to any one of (1-9), (1-12), (2-9) and (2-12), wherein the nucleic acid monomer includes a CpG motif.

Effects of Invention

According to the present invention, gelation of nucleic acid having various sequences can be carried out by adjusting the salt concentration, the nucleic acid concentration and the number of bases of protruding ends without adding a nucleic acid linking enzyme such as a ligase, so that a hydrogel having less content of additives can be produced. Furthermore, in the present invention, it is not necessary to use an organic compound which may have a concern about safety in gel production. Furthermore, problems of safety and antigenicity in using an enzyme such as a ligase are also overcome. Furthermore, it has been difficult to prepare a nucleic acid gel having excellent viscoelasticity according to the conventional method using a ligase. However, it has been found that a nucleic acid gel having excellent viscoelasticity can be prepared according to the method of the present invention.

Furthermore, DNA and RNA can be a ligand of Toll-like receptors (TLRs) expressing in mammalian cells including human cells, and fine particles like hydrogel can be easily taken into an immunologically competent cell expressing TLRs, and therefore the system of the present invention which is formed based on nucleic acid has a function as an immunological adjuvant efficiently activating the immunologically competent cell in addition to a function of carrying out sustained release of a physiologically active substance. Furthermore, the present invention can overcome a problem that a behavior of the adjuvant and a behavior of the antigen in a living body are carried out separately. Furthermore, according to the gelation by the method of the present invention, for example, by using the CpG motif, it is possible to a obtain nucleic acid preparation exhibiting high cellular immunological stimulation properties when this is introduced into a living body. Moreover, according to the present invention, it is possible to prepare an immunological adjuvant with less adverse effect.

In general, there is a problem that gel formulations need section or the like in administration, but according to the system of the present invention, gelation can be carried out in a body after administration in a sol state. This makes it possible to carry out administration by injection, nebulization, instillation, or application. Furthermore, unlike microfabricated gel, since gelation is carried out in a body after administration in a sol state, gel properties such as sustained release may not be damaged. Furthermore, the gel of the present invention has thixotropy and is gelated again in a body even when it is administered via a syringe, and therefore gel properties such as sustained release are not damaged.

Furthermore, gelation proceeds by change of the nucleic acid concentration or the salt concentration, and heating or the like is not necessary for gelation. Therefore, it is also possible to encapsulate substances that are weak to heat or chemical reaction, for example, antigen proteins or cells, and there is a small possibility of denature even when an unstable substances is encapsulated. Therefore, even when relatively large substances are enclosed in a gel, there is a small risk that a function of the enclosed substances is damaged. Also, the gel according to the present invention is stable with respect to surrounding environments.

Furthermore, nucleic acid drugs such as antisense DNA, siRNA, CpG DNA can be also incorporated into a structure. As to immunological activation, a system that does not activate immunization can be constructed by selecting a suitable base sequence. The strength of the gel can be controlled by a structure of a nucleic acid unit and the number of protruding ends, and gelation can be controlled by adjusting the nucleic acid concentration, the salt concentration and the number of bases at protruding ends. With such adjustment, the internal structure of the gel, the gel strength, the releasing rate of the encapsulated substance can be also controlled. Furthermore, various functional molecules can be inserted into a part of the end of the nucleic acid unit, and this makes it possible to largely change physical properties. Various modified nucleic acids can be also used.

BRIEF DESCRIPTION OF DRAWINGS

FIG. 4 Estimated schematic views showing formation of a gel by mixing a group of nucleic acid monomer capable of forming two kinds of nucleic acid units.

FIG. 5 A protocol for forming a hydrogel in which an encapsulated substance is internally enclosed, and scanning electron microscope images of the gel.

FIG. 8-1 Photographs showing that after the sol-like composition is administered, a gel is formed in a living body, and a scanning electron microscope image of the gel formed in the living body.

FIG. 8-2 Photographs (A) showing a DNA solution or a DNA hydrogel in a syringe and after it is extruded from the syringe; a photograph (C) showing a site in which the DNA solution or the DNA hydrogel is intradermally administered; and graphs (B) showing viscoelasticity of hydrogel before passing through the syringe (B left) and after passing through the syringe (B right).

FIG. 9 Photographs showing a sequence of an immunologically active or immunologically inactive oligonucleotide which contains or does not contain a CpG motif, and a stimulation activity of a gel which is obtained by using the oligonucleotide after addition to dendritic cells. The left column of tetrapodna includes SEQ ID NOs:14-17 from the top to the bottom of the column, respectively. The right column of tetrapodna includes SEQ ID NOs:4, 2, 5, and 6 from the top to the bottom of the column, respectively.

FIG. 10 Examples of oligonucleotides having various sequences. The examples shown include SEQ ID NOs:1-10 and 18-33 from the top to the bottom of the recited sequences, respectively.

FIG. 11 An estimated schematic view showing formation of a gel by mixing two kinds of Tetrapodnas, and a photograph showing an outline of the hydrogel formed by mixing. Tetrapodna A1 through A4 include SEQ ID NOs:34-37, respectively. Tetrapodna B1 through B4 include SEQ ID NOs:38-41, respectively.

FIG. 12 An estimated schematic view showing formation of a gel by mixing Tetrapodna and double strand DNA (ds-DNA), and a photograph showing an outline of the hydrogel formed by mixing. Tetrapodna A1 through A4 include SEQ ID NOs:34-37, respectively. Double stranded DNA ds1 and ds2 include SEQ ID NOs:42 and 43, respectively.

FIG. 15 Estimated steric structures of the gel of the present invention.

FIG. 16 Scanning electron microscope images showing a difference in the internal structure of a gel obtained by using various nucleic acid units.

FIG. 21 Fluorescence microscope images showing that GFP-labeled bone marrow-derived cells (BMDCs) are incorporated into a DNA hydrogel.

FIG. 24 Graphs showing CD spectra of DNA preparations.

FIG. 25 Photographs (A and B) as well as graphs (C and D) showing degradation of polypodna preparations in mouse serum.

FIG. 31 A graph showing uptake of polypodna preparations containing CpG by cells.

MODE FOR CARRYING OUT THE INVENTION

1. Definition

Figure 1:
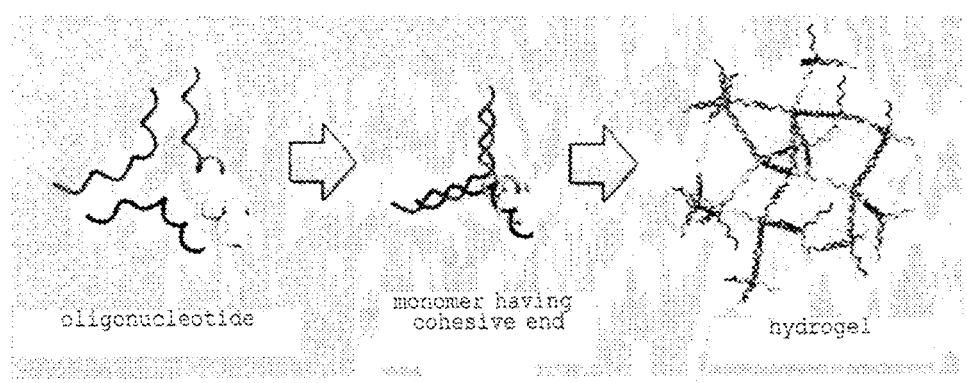
FIG. 1 An estimated schematic view showing formation of a hydrogel from an oligonucleotide in accordance with the present invention.

In the claims, the term "body temperature" means 37° C., and the term "in the physiological condition" denotes a condition in which the salt concentration is 150 mM in terms of a NaCl concentration.

In the present specification and the claims, the term "nucleic acid monomer" is selected from the group consisting of nucleic acid, a nucleic acid derivative, a modified nucleic acid, a compound binding to nucleic acid in a complementary manner, and a mixture thereof, and denotes a compound forming the below-defined "nucleic acid unit." Specifically, one "nucleic acid monomer" includes a moiety that constitutes a cohesive protruding end (an "x moiety" in the following schematic view) and a complementary base sequence moiety (a "y moiety" in the following schematic view) capable of forming a double strand together with another nucleic acid monomer.

In the present specification and the claims, the term "nucleic acid unit" is an estimated structure unit constituting a hydrogel (hereinafter, also referred to as a "gel" simply) formed when the nucleic acid monomer concentration and the salt concentration in an aqueous solution including the above-mentioned nucleic acid monomer are increased to a predetermined concentration or higher, and has structures shown in the below-mentioned schematic views (n=2 to 12). However, the internal structure of the gel obtained by the present invention is not actually confirmed, and it is estimated that each nucleic acid monomer in the formed gel forms a gel via formation of the nucleic acid unit having the following structure. Note here that the "nucleic acid unit" is conveniently shown in a plan view in the following schematic views, but it is estimated that it actually has a complicated steric structure shown in the lower part of FIG. 10. It is estimated that such "nucleic acid units" bind to each other with mutual complementarity of cohesive protruding ends constituting the nucleic acid unit in the nucleic acid monomer, so that gels having complicated high-order structures shown in FIG. 15 are formed.

[Schematic Views of Nucleic Acid Unit]

[Chemical Formula 1]

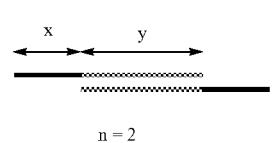

n = 2

[Chemical Formula 2]

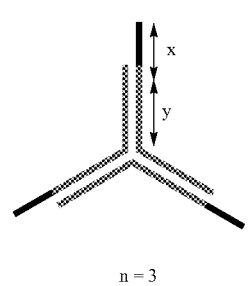

n = 3

-continued

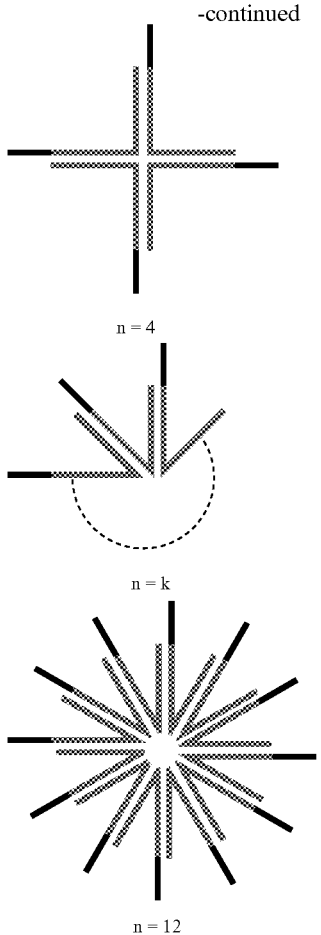

In the schematic views, x denotes a moiety constituting a "cohesive protruding end" for linking one nucleic acid unit to another nucleic acid unit with the complementarity thereof, and y denotes a "complementary base sequence moiety" capable of forming a double strand of a nucleic acid monomer constituting a nucleic acid unit and another nucleic acid monomer. Hereinafter, the "cohesive protruding end" may be also referred to as simply "x", and the "complementary base sequence moiety" may be also referred to as simply "y."

In the present specification and the claims, a "nucleic acid unit" that is estimated to be formed into a gel or a "nucleic acid monomer aggregate capable of forming a nucleic acid unit" in a sol may be also referred to as "xxxpodna." The xxx portion includes, for example, tri, tetra, hepta, hexa, and the like, representing the number of n in the above-mentioned nucleic acid unit. That is, when n=3 is satisfied in the schematic view, a nucleic acid unit or a nucleic acid monomer aggregate capable of forming a nucleic acid unit may be referred to as "tripodna," and similarly, it may be referred to as "tetrapodna" when n=4 is satisfied. Furthermore, in the term "xxxpodna (a-b-b)," "a" represents the number of bases of oligonucleotide forming an x moiety in the schematic view, and "b" represents the number of oligonucleotide forming a y moiety in the schematic view. However, when n=2 is satisfied, exceptionally, it is represented as "double strand nucleic acid" or "ds" or "dsDNA."

In the present specification and the claims, the term "complementarity" or a numerical value represented by the term "complementary" plus % denotes a moiety constituting two nucleic acid monomers having the same length, for example, a numerical value given by the formula: number of bases forming a base pair with each other/total number of bases×100 when two xs or two ys are compared with each other.

2. Summary of the Invention

The present invention will be described below simply with reference to the above-mentioned schematic views.
(A) Formation of Gel from One Kind of Nucleic Acid Unit First, a gel composed of one kind of nucleic acid unit defined above is described.

When a gel is formed from one kind of nucleic acid unit, the nucleic acid unit is one kind selected from units represented by the below-mentioned schematic views.

[Chemical Formula 3]

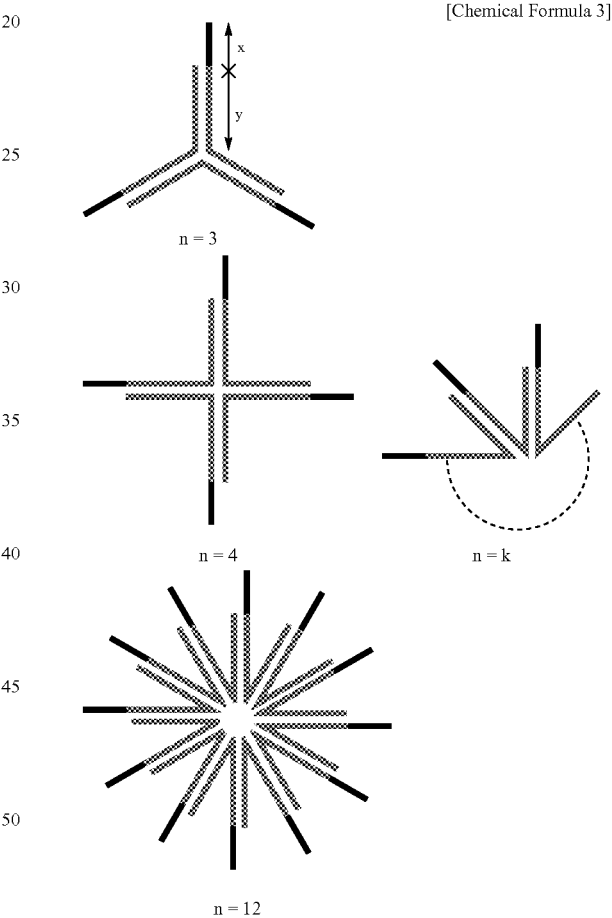

In the above-mentioned schematic view, the range of n is 3 to 12, preferably 3 to 8, and further preferably 3 to 6. When the value of n is too small or too large, a gel tends to be hardly formed.

According to the present invention, an aqueous solution including a nucleic acid monomer capable of forming the nucleic acid unit exists as a sol at a low salt concentration and a low nucleic acid concentration, but in the conditions of combination of a predetermined high salt concentration and high nucleic acid concentration, y moieties constituting a nucleic acid monomer form a double strand with the complementarity thereof, and thereby a nucleic acid unit having the estimated structure is formed, and an x moiety constituting a nucleic acid monomer in one nucleic acid unit and an x moiety constituting a nucleic acid monomer in another nucleic acid unit form a double strand with the complementarity thereof, so that a large number of nucleic acid units are linked to each other to form a gel. This mechanism is shown in FIG. 1 and the estimated internal structure of the gel is shown in FIG. 15.

(B) Formation of Gel from Two or More Nucleic Acid Units

Next, a gel composed of two or more nucleic acid units defined above is described.

When a gel is formed from two or more nucleic acid units, the nucleic acid units are two or more nucleic acid units selected from the units shown in the following schematic views; however, in at least one kind, n is not 2 (n is 3 to 12).

[Chemical Formula 4]

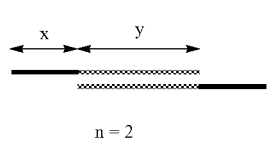

n = 2

[Chemical Formula 5]

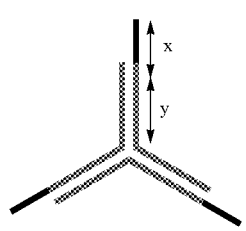

n = 3

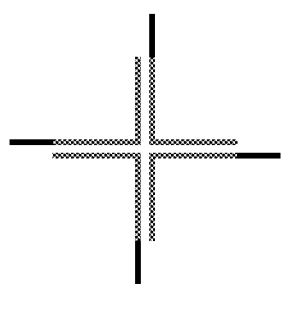

n = 4

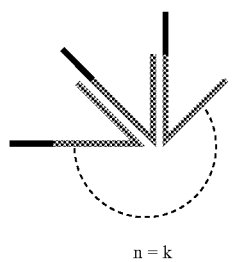

n = k

-continued

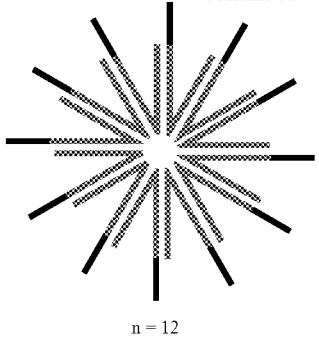

n = 12

That is, in the above-mentioned schematic views, the range of n is 2 to 12, preferably 2 to 8, and further preferably 2 to 6. When n is 2 in one kind of the nucleic acid unit, n is 3 to 12, preferably 3 to 8, and further preferably 3 to 6 in at least another kind of the nucleic acid unit.

An aqueous solution including nucleic acid monomers capable of forming two or more kinds of the nucleic acid units exists as a sol at a low salt concentration and a low nucleic acid concentration. Furthermore, in two or more kinds of the nucleic acid units, x of one kind of the nucleic acid unit and x of another kind of the nucleic acid unit need to be complementary to each other, but x does not need to be complementary to x itself (self-complementary, for example, palindrome sequence). When x moieties of two or more kinds of the nucleic acid units are not self-complementary, an aqueous solution including one of the nucleic acid units does not form a gel even at a high salt concentration and a high nucleic acid concentration, and always exists as a sol. On the other hand, an aqueous solution including two kinds of the nucleic acid units exists as a sol at a low salt concentration and a low nucleic acid concentration, but in the conditions of combination of a predetermined high salt concentration and high nucleic acid concentration, y moieties constituting a nucleic acid monomer form a double strand with the complementarity thereof, and thereby a nucleic acid unit having the above-mentioned estimated structure is formed, and an x moiety constituting a nucleic acid monomer in one nucleic acid unit and an x moiety constituting a nucleic acid monomer in another nucleic acid unit form a double strand with the complementarity thereof, so that a large number of nucleic acid units are linked to each other to form a gel.

Therefore, when nucleic acid monomers capable of forming two or more kinds of the nucleic acid units are provided as separate aqueous solutions each including a nucleic acid monomer capable of forming one kind of the nucleic acid unit, they are singly a sol state regardless of the salt concentration and the nucleic acid concentration. However, when they are mixed with each other in conditions of combination of a predetermined high salt concentration and high nucleic acid concentration, a gel is formed. That is, aqueous solutions with high salt concentration, each of which includes the nucleic acid monomer capable of forming each nucleic acid unit at a high concentration, are singly a sol. However, a gel can be formed by only mixing the aqueous solutions. The mechanism of the formation of a gel by the mixing is shown in FIG. 4, FIG. 11 and FIG. 12.

3. Detailed Description of the Invention

Hereinafter, the present invention will be described in detail; however, the present invention is limited by the claims, and is not limited by specific description in the above-mentioned summary of the invention and the below-mentioned detailed description of the invention.

Cohesive Protruding End (x in Schematic View)

In the present invention, the length of x necessary for forming a gel is, in the number of bases, 4 bases or more, preferably 6 bases or more, and further preferably 8 bases or more. The upper limit thereof is not particularly limited, but for example, it is preferable that the length is 12 bases or less. Suitable length of x is, although depending upon the number of n, preferably 4 to 12 bases, and further preferably 8 to 12 bases. When the length of x is long, a gel tends to be easily formed, but when the length of x is short, the internal structure of a gel tends to become finer (dense).

The sequence of x is not particularly limited, but as described in (A) described above, when a gel is produced from one kind of nucleic acid unit, for example, x can be complementary to x itself (self-complementary), the sequence of such x includes a palindrome sequence. As described in (B) described above, when a gel is produced from two or more kinds of the nucleic acid units, x needs to be complementary to x in the nucleic acid monomer capable of forming at least one kind of other nucleic acid unit. In both cases, the degree of the complementarity may be such a degree as to form a double strand sequence showing a melting temperature that is equal to or higher than the body temperature in a physiological condition. The complementarity of x is, when it is represented by a numerical value, for example, preferably 90% or more complementary, more preferably 95% or more complementary, and most preferably 100% complementary (a palindrome sequence). A cohesive protruding ends in a nucleic acid monomer may be the same in all kinds of nucleic acid monomers capable of constituting one kind of nucleic acid unit. Furthermore, the cohesive protruding end in the nucleic acid monomer may have a palindrome sequence structure which has the same sequence in all parts. A cohesive protruding end in a nucleic acid monomer for constituting a certain nucleic acid unit may be complementary to a cohesive protruding end in all parts or a part of nucleic acid monomer for constituting another nucleic acid unit. Furthermore, a cohesive protruding end in a nucleic acid monomer may not be complementary to a cohesive protruding end in all parts or a part of nucleic acid monomer for constituting the same nucleic acid unit together with the nucleic acid monomer.

Complementary Base Sequence Moiety (y in Schematic Views)

In the present invention, the length of y necessary for forming a gel is, in the number of bases, 8 bases or more, preferably 14 bases or more, and further preferably 18 bases or more although depending upon the number of n. The upper limit of the length of y is not particularly limited, but when, for example, n is 3, the length of y is 8 bases or more and 45 base or less. The upper limit of the length of y is, for example, 45 or less, preferably 30 or less, and more preferably 20 or less. When the number of n is increased, the length of y necessary for forming a gel tends to be increased, but when the length of y is short, the internal structure of a gel tends to become finer (dense).

The sequence of y is not particularly limited, but the sequence of y in one nucleic acid monomer needs to be complementary to the sequence of y in another nucleic acid monomer that is a constituent element of a nucleic acid unit constituted thereby so that a nucleic acid unit in the above-mentioned schematic view can be formed. The degree of the complementarity may be such a degree as to form a double strand sequence showing a melting temperature that is equal to or higher than the body temperature in a physiological condition. The complementarity of two ys forming a double strand in the same nucleic acid unit is, although depending upon the number of n, for example, preferably 85% or more complementary, more preferably 90% or more complementary, further preferably 95% or more complementary, and the most preferably 100% complementary when it is represented by a numerical value. For example, it is demonstrate that when the number of n is 6 and the complementarity of two ys is 89%, a gel can be formed.

The sequences of n arms (composed of a double strand of two ys) forming the nucleic acid unit may preferably have sequences different from each other. For example, when n is 4, the sequence of the nucleic acid monomer can be represented by x-a-b (in this case, a and b denote y, respectively), x-c-d, x-e-f and x-g-h. However, in order to form a complete nucleic acid unit, b and c, d and e, f and g, as well as h and a needs to be complementary to each other. For example, when a gel is formed in a living body, the complementarity thereof needs to be complementary to such a degree as to form a double strand sequence showing a melting temperature that is equal to or higher than the body temperature in a physiological condition. When the complementarity between the other sequences (for example, b and e) is high, a uniform nucleic acid unit may not be formed. However, in the formation stage of a gel, conditions can be set strictly (for example, it is thought that temperature is lowered very slowly), and n arms may have a similar sequence.

The sequences of two ys in one nucleic acid monomer may be appropriately designed by predicting the complementarity to the other nucleic acid monomer or the stability of a hairpin structure that can be formed from one nucleic acid monomer. That is, free energy involved in binding to the hairpin structure or a sequence in the nucleic acid monomer out of interest may be made to be larger than free energy involved in forming arms of interest (double strand). That is, the sequence of y may be appropriately designed such that, in a gel formation condition, the nucleic acid monomer is stabilized in terms of energy when the nucleic acid unit is formed as compared with the case where the nucleic acid monomers exist separately or in a structure form other than the estimated nucleic acid unit.

Sequence and Modification in Consideration of Functions of Nucleic Acid Monomer

The nucleic acid monomer of the present invention may have various nucleic acid sequences according to functions required for a gel to be formed, or may include a modified nucleic acid, or may include a modifying group for addition other than nucleic acid. For example, a nucleic acid monomer including DNA may contain a CpG motif, thereby enabling the immune activity of the resulting gel to be enhanced. Note here that the optimum sequence of the "CpG motif" is said to be GTCGTT for human, and GACGTT for rodents (mouse and rat). In the argument for mice, generalized purine-purine-C-G-pyrimidine-pyrimidine may be used, but it is not suitable for an optimum human sequence. Furthermore, other than this, it has been reported that a large number of CpG motifs show immunological activation. Furthermore, it has been reported that there is a positive correlation between the number of the CpG motifs in the sequence and the immune activity. Note here that in the present specification, the CpG motif may be simply abbreviated as CpG.

Alternatively, other than the DNA sequence, an RNA sequence can be also utilized. For example, a gel including siRNA that is known as a functional nucleic acid can be formed. Furthermore, a modified nucleic acid may be included in a nucleic acid monomer. Examples of the modified nucleic acid include 2'-O-methyl modified nucleic acid, phosphorothioate-modified nucleic acid, morpholino nucleic acid, LNA, PNA, and the like. They can be used for preparation of any gels in the form of derivatives and analogs which have been developed to date. Only a natural type nucleic acid may be used, and a modified nucleic acid may be used from the viewpoint of stability.

Furthermore, other than the modified nucleic acid, modification groups such as cholesterol and other lipids may be directly added to the nucleic acid monomer. For example, in a gel obtained by adding cholesterol to the nucleic acid monomer, transferability to a target tissue (for example, skin tissue in the case of dermal administration) or cell uptake rate can be increased.

Formation of Gel Including Encapsulated Substance

According to the present invention, a gel composed of nucleic acid can internally enclose various substances. Examples of the substances to be internally enclosed include, but are not particularly limited to, DNA intercalators such as doxorubicin and daunomycin; peptides and peptide pharmaceutical agents such as insulin; protein antigens such as egg albumin and *Cryptomeria japonica* antigen; proteins and protein pharmaceutical agents such as growth factors and cytokines; cells, genetically modified cells, and the like. Detail of the mechanism of internal enclosure is not clear, but it is thought that an encapsulated substance that exists during binding between nucleic acid units occurs is trapped in a gel. Therefore, first, a sol is prepared, and an encapsulated substance is added thereto so as to increase, for example, the salt concentration and the nucleic acid concentration, thereby enabling a gel internally enclosing an encapsulated substance to be formed. Furthermore, the addition amount of the encapsulated substance is not particularly limited, and the encapsulated substance can be enclosed even when the amount may be the same level as the weight of the gel.

Note here that the size of the gel of the present invention is not particularly limited, and basically there is no upper limit. For example, when 0.5 mM DNA produces 500 µl of gel, a numerical value such as $0.5 \times 10^{-3}$ (mol/l)$\times 500 \times 10^{-6}$ (l)$\times 6 \times 10^{23}$ (molecule/mol)$=1.5 \times 10^{17}$ is obtained, but the strict size is not clear.

Factors Involved in Gelation

As mentioned above, the sol-state composition of the present invention, which is capable of forming a gel, tends to be gelled by increasing the salt concentration or increasing the nucleic acid concentration. As to temperatures, at high temperatures, solation tends to occur rather than gelation, and at low temperatures, gelation tends to occur. Furthermore, the gelation can be controlled also by the sequence of a nucleic acid monomer forming a gel or the length of the cohesive protruding end. For example, when a gel is intended to be formed in a living body, the sequence may be designed such that Tm of the double strand and the cohesive protruding end of each nucleic acid monomer forming a gel is made to be higher than the living body temperature (about 37° C.)

As the salt, sodium ions that are monovalent cations are used in Example, but the salt is not limited thereto, divalent cations such as magnesium ions and calcium ions can be utilized. The divalent cation enables gelation of nucleic acid at a lower concentration as compared with the case where the monovalent cation is used;

It is essential that the composition of the present invention does not include a nucleic acid linking enzyme. Examples of components contained in the composition include a nucleic acid monomer, salts (the above-mentioned monovalent or divalent cations and counter anions thereof), a buffer agent, the above-mentioned encapsulated substances, and the like, in addition to water. Any other components may be contained as long as they do not inhibit the purpose of the present invention.

Formation of Gel in Living Body

The composition of the present invention can be administered in a sol state and then gelled in a living body. Examples of the administration embodiments include, but are not limited to, skin administration, injection, intranasal administration, and the like. When the composition is administered to the skin surface, gelation occurs on the skin. When the composition is administered by injection, according to injection sites, gelation occurs in the subcutaneous site, in the intradermal site, in the intramuscular site, in the intraperitoneal site, and the like. When the composition is administered by intranasal administration, gelation occurs in the nasal cavity.

As (A) described above, when a gel is formed from one kind of nucleic acid unit in a living body, it is preferable that the sol-like composition of the present invention for administration in a living body is maintained at a low salt concentration and a low nucleic acid concentration in order to prevent gelation from occurring before administration. When the sol-like composition of the present invention with a low salt concentration and a low nucleic acid concentration is administered, the salt concentration is lower than the living body salt concentration (about 150 mM in terms of a NaCl concentration), and therefore absorption of moisture and secretion of salt occurs in a living body after administration. Thus, the nucleic acid concentration and the salt concentration are increased, which drives gelation.

As (B) described above, when a gel is formed from two or more kinds of the nucleic acid units in a living body, two or more kinds of sol-like compositions whose salt concentration and nucleic acid concentration are kept low as mentioned above may be administered. However, each of the sol-like compositions including a monomer capable of forming one kind each of different nucleic acid units is not gelled at a high salt concentration and a high nucleic acid concentration as a single composition, and therefore each of them may be administered as a sol-like composition with a high salt concentration and a high nucleic acid concentration. When two or more kinds of sol-like compositions with a low salt concentration and a low nucleic acid concentration are used, even when they are administered simultaneously or separately, the salt concentration and the nucleic acid concentration become high in a living body and therefore a gel is formed. However, when two or more kinds of sol-like compositions with a high salt concentration and a high nucleic acid concentration are used, they are gelled only by being mixed with each other. Therefore, it is preferable that they are administered separately and then mixed to be gelled for the first time in a living body.

Administration in Gel State

Furthermore, the gel of the present invention has thixotropy, so that it may be administered in a gel state. The gel of the present invention has viscoelasticity that is the same level as that of the gel before it is allowed to pass through a syringe, even after it is allowed to pass through the syringe, and therefore administration by injection is possible.

Number of Nucleic Acid Monomers Constituting Nucleic Acid Unit

The number of nucleic acid monomers for forming a nucleic acid unit is dependent upon the number of bases in the nucleic acid monomer, kinds of salts to be used for gel formation, a salt concentration, pH and other buffer agents. When nucleic acid having immune stimulation properties, for example, a CpG motif, is included, the more the number of bases of the nucleic acid monomer is, the higher the immune stimulation properties become. Furthermore, as to a nucleic acid monomer including a motif having immune stimulation properties, when nucleic acid units having the same nucleic acid amount and the same motif amount are compared with each other, the more the number of the nucleic acid monomers constituting the nucleic acid unit is, the higher the immune stimulation properties become. However, when the number of the nucleic acid monomer is increased, formation of nucleic acid units may not be carried out sufficiently in a physiological condition. A non-physiological condition is not suitable for pharmacological application of a gel using a nucleic acid unit. Furthermore, in nucleic acid monomers having a large number of bases, the cost is high and purification is difficult. Furthermore, when the number of nucleic acid monomers constituting the nucleic acid unit is increased, the number of nucleic acid ends in the nucleic acid gel is increased so that the nucleic acid is susceptible to degradation due to exonuclease, and the stability in the serum is lowered. Accordingly, when a motif such as a CpG motif having immune stimulation properties is used, in order to increase the immune stimulation properties, the number of nucleic acid monomers constituting the nucleic acid unit is suitably 3 to 12, further suitably 4 to 8, and particularly suitably 6 to 8.

Improvement of Immune Stimulation Properties by Gelation of Present Invention

Figure 28:
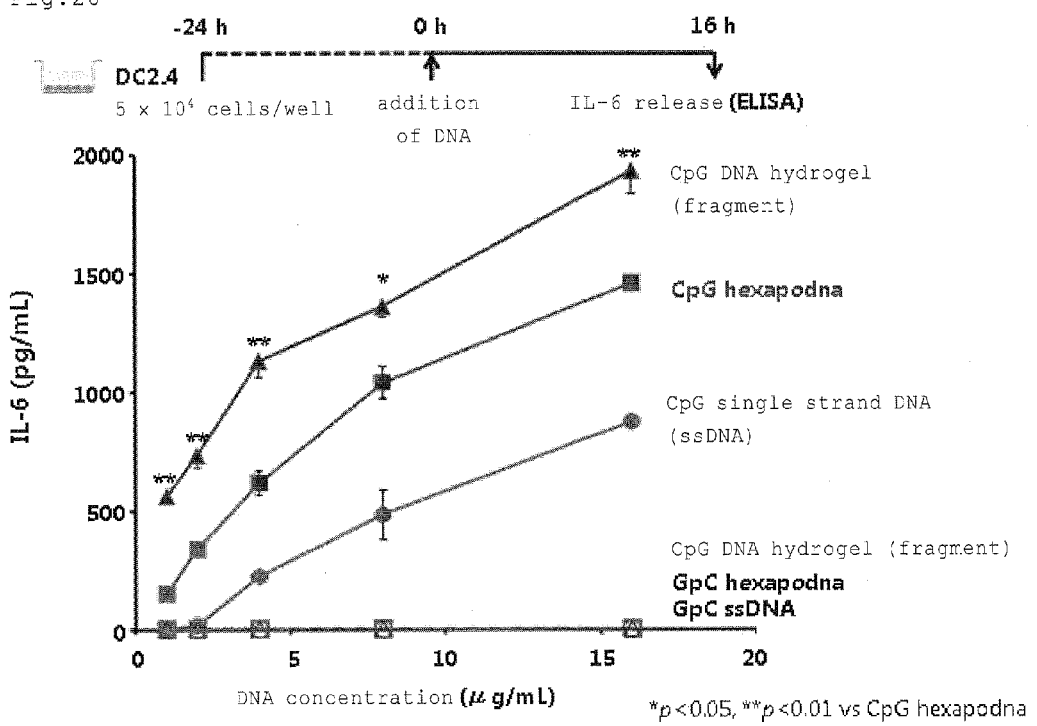
FIG. 28 A graph showing an induction effect of IL-6 release by the CpG DNA hydrogel.
Figure 34:
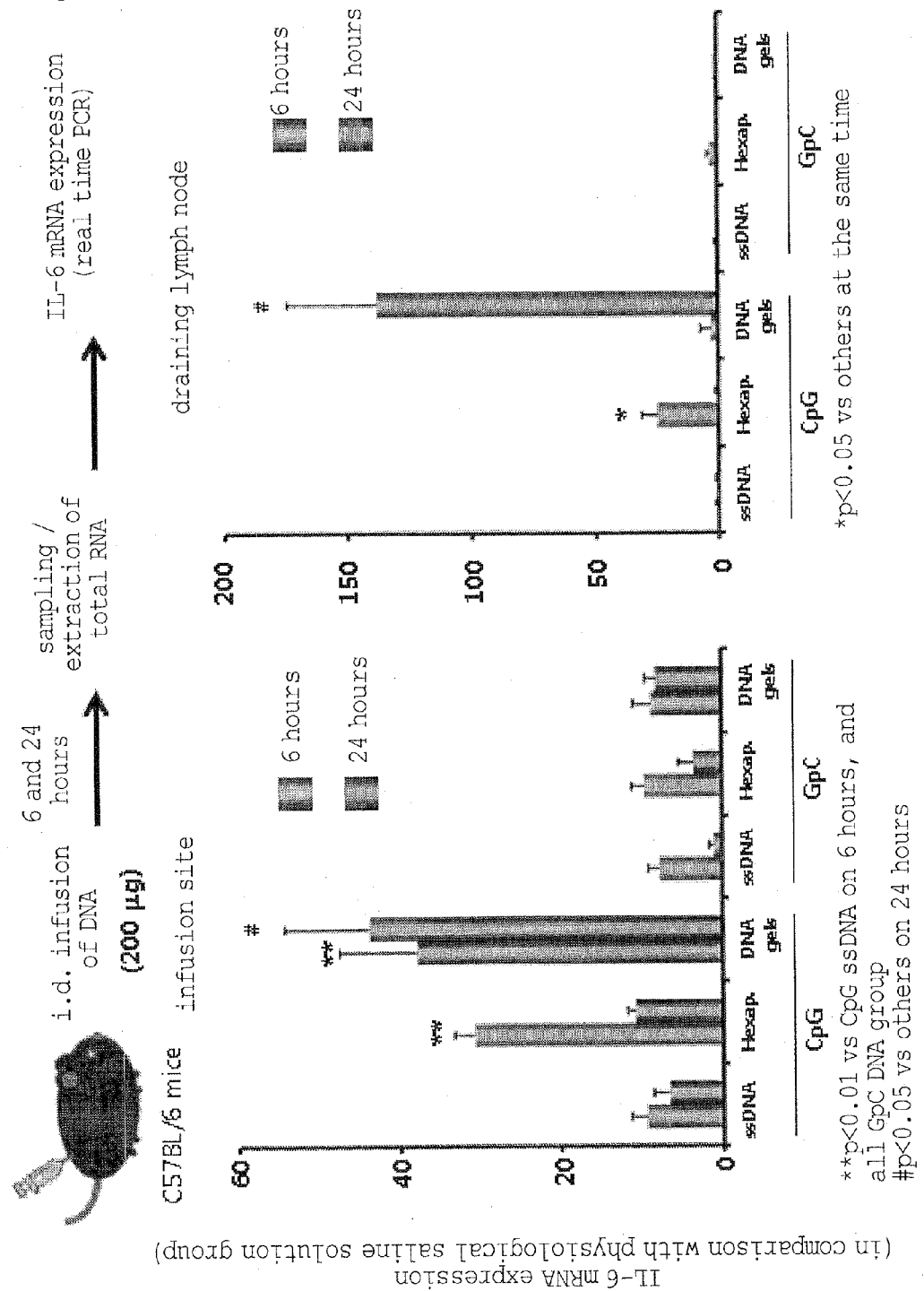
FIG. 34 Graphs showing that a DNA hydrogel containing CpG continuously and strongly induces IL-6 mRNA expression.
Figure 35:
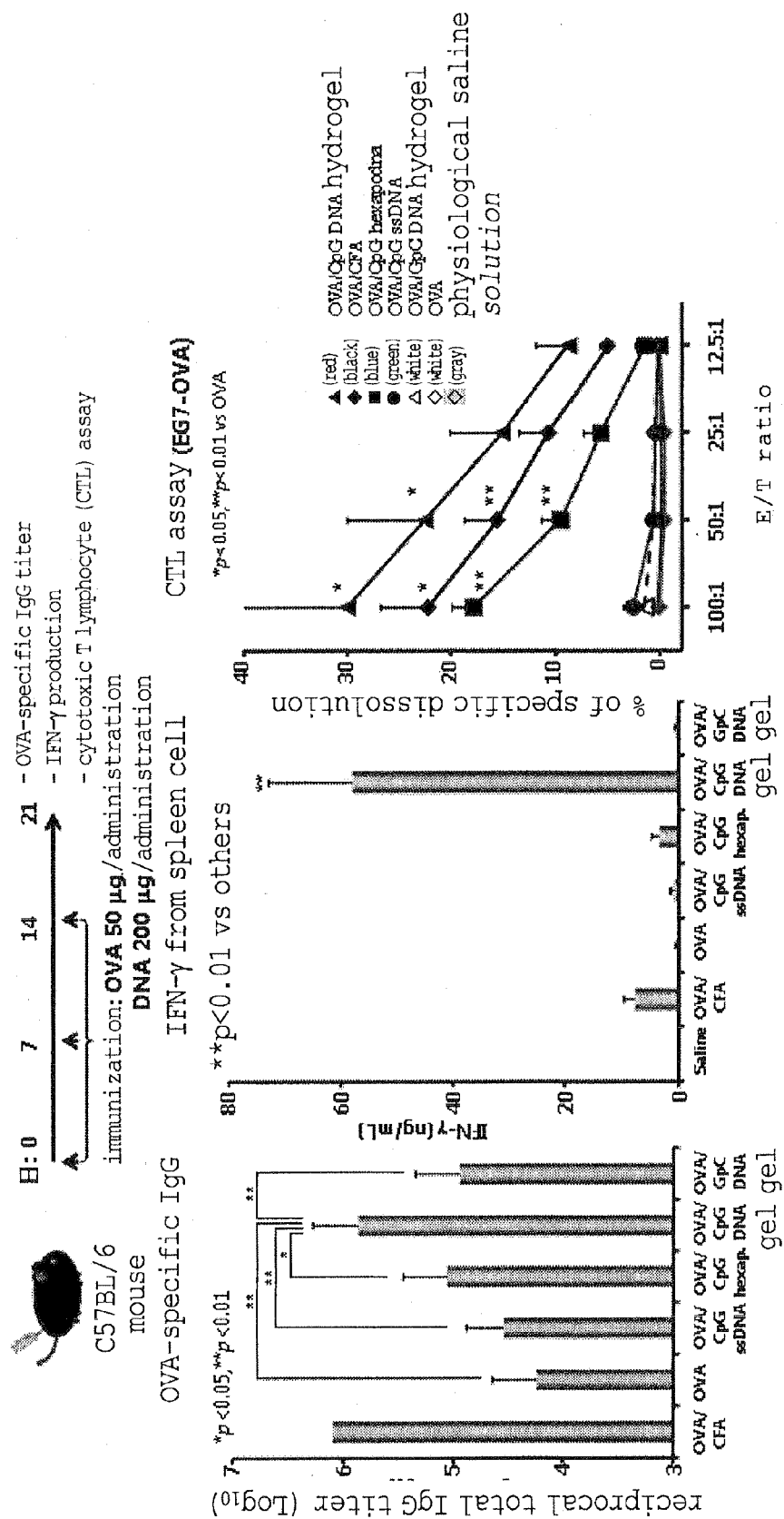
FIG. 35 Graphs showing that a CpG DNA hydrogel internally containing OVA strongly induces an adaptive immune response.

As shown in Examples described below, a nucleic acid monomer containing an element having immune stimulation properties, for example, a CpG motif, shows a high degree of activation of immune response in the case where it is used in a single strand state as compares with the case where it is used in a state of a nucleic acid unit (polypodna) or in a state of a nucleic acid gel (FIG. 28, FIG. 34, and FIG. 35). In this way, according to the gelation by the method of the present invention, it is possible to obtain a nucleic acid preparation showing high cell immune stimulation properties in the case of introduction into a living body.

4. Detailed Description of Each Invention

As mentioned above, the present invention including action mechanism is described with reference to preferable embodiments; however, the invention is not limited by the above-mentioned summary of the invention and specific description in the detailed description of the invention.

The present invention can provide (1-1) and (2-1), that is, the followings:

a nucleic acid sol-like composition for producing a nucleic acid gel without using a nucleic acid linking enzyme, the composition comprising two or more nucleic acid monomers which are partly complementary to each other and which are selected from the group consisting of nucleic acid, a nucleic acid derivative, a modified nucleic acid, a compound binding to nucleic acid in a complementary manner, and a mixture thereof, wherein one nucleic acid monomer has a moiety which constitutes a cohesive protruding end and a complementary base sequence moiety that can form a double strand with one or more other nucleic acid monomers, and the composition does not contain a nucleic acid linking enzyme, and a sol-like composition for producing a nucleic acid gel which does not contain a nucleic acid linking enzyme, the composition containing a mixture of two or more oligonucleotides composed of a cohesive protruding end moiety and a complementary base sequence moiety in the composition at a nucleic acid concentration of 0.3 mM+1.6/x (the number of bases in the protruding end moiety) mM or less, not containing a nucleic acid linking enzyme, and having a salt concentration of 80 mM/x (the number of bases in the protruding end moiety) or less in terms of a NaCl concentration:

[wherein the cohesive protruding end moiety is a single strand nucleic acid moiety having 4 to 12 nucleotide length and being complementary to a cohesive protruding end moiety in at least another oligonucleotide to such a degree as to form a double strand sequence showing a melting temperature that is equal to or higher than the body temperature in a physiological condition, and the complementary base sequence moiety that binds to the other oligonucleotide in a complementary manner has 8 to 45 nucleotide length and is complementary to the complementary base sequence moiety in the other oligonucleotide to such a degree as to form a double strand sequence showing a melting temperature that is equal to or higher than the body temperature in a physiological condition].

The inventions according to (1-1) and (2-1) relate to a nucleic acid sol-like composition for producing a nucleic acid gel without using a nucleic acid linking enzyme, which does not contain a nucleic acid linking enzyme.

In (1-1), the terms "nucleic acid monomer" and "complementary" are defined as mentioned above. The nucleic acid monomer is constituted of a "cohesive protruding end" and a "complementary base sequence moiety." Furthermore, preferably, as in (2-1), the "nucleic acid monomer" is so-called an "oligonucleotide."

In both (1-1) and (2-1), the "cohesive protruding end" is a portion corresponding to x described with reference to the schematic view in the detailed description, and when two or more of certain "nucleic acid monomers" gather to form a certain estimated "nucleic acid unit", the portion is a portion remaining as a single strand moiety in the nucleic acid unit, and is a portion capable of forming a double strand in specific conditions when it is mutually complementary to the same portion remaining as a single strand moiety in a nucleic acid unit in a nucleic acid monomer constituting another "nucleic acid unit."

In both (1-1) and (2-1), the "complementary base sequence moiety" is a moiety corresponding to y (two ys) described with reference to the schematic view in the detailed description, and when two or more of certain "nucleic acid monomers" gather to form a certain estimated "nucleic acid unit", the moiety is a moiety capable of forming a double strand in specific conditions when it is mutually complementary to the same moiety in another nucleic acid monomer constituting the same nucleic acid unit in the nucleic acid unit.

In (1-1), the "nucleic acid monomer" is selected from the group consisting of nucleic acid, a nucleic acid derivative, a modified nucleic acid, a compound binding to nucleic acid in a complementary manner, and a mixture thereof. The nucleic acid denotes naturally occurring DNA or RNA or a mixture thereof. Preferably, as in (2-1), the nucleic acid monomer is an oligonucleotide. The nucleic acid derivative is a derivative obtained by adding a modifying group to naturally occurring DNA or RNA or a mixture thereof. Examples of the modifying group include, but are not particularly limited to, lipids such as cholesterol. The modified nucleic acid is obtained by adding modification that is known to persons skilled in the art to at least any one moiety of a sugar moiety, a base moiety, and a phosphate-bond moiety of naturally occurring DNA or RNA or a mixture thereof. Examples of the modified nucleic acid include, but are not particularly limited to, 2'-O-methyl modified nucleic acid, phosphorothioated-modified nucleic acid, morpholino nucleic acid, LNA, and the like. Furthermore, the compound binding to nucleic acid in a complementary manner is a compound that can be bound to nucleic acid molecules such as DNA and RNA by non-covalent bond due to the structural properties thereof, and examples of the compound include PNA.

The sol-like compositions of (1-1) and (2-1) respectively include the "nucleic acid monomer" and two or more kinds of "oligonucleotides" as a mixture. As described in (A) described above, in the sol-like composition for forming a gel from one kind of nucleic acid unit, the kinds of the "nucleic acid monomer" and "oligonucleotide" are 3 to 12, preferably 3 to 8, and further preferably 3 to 6 as described in "n" of (A). As described in (B) described above, in the sol-like composition for forming a gel from two or more kinds of the nucleic acid units, the kinds of the "nucleic acid monomer" and "oligonucleotide" are 2 to 12, preferably 2 to 8, and further preferably 2 to 6 as described in "n" of (B).

The structure, that is, the length, sequence, and mutual complementarity of the "cohesive protruding ends" and the "complementary nucleotide sequence moieties" of the "nucleic acid monomer" and "oligonucleotide" included in the sol-like compositions of (1-1) and (2-1) are not particularly limited, but are preferably as described in the description of x and y in the detailed description of the invention.

The sol-like composition of (2-1) is a further limited composition of the sol-like composition of (1-1), and characterized in that the sol-like composition contains a mixture of two or more oligonucleotides in the composition at a nucleic acid concentration of 0.3 mM+1.6/x (the number of bases in the protruding end moiety) mM or less and at a salt concentration of 80 mM/x (the number of bases in the protruding end moiety) or less in terms of a NaCl concentration. The "x" to be used herein denotes the number of bases forming the protruding end moiety of oligonucleotide. The expression "80 mM/x or less in terms of a NaCl concentration" refers to as 80 mM/x or less when the salt in the composition is a monovalent cation, and refers to as the half of the concentration when the salt in the composition is a divalent cation.

The sol-like composition of (2-1) is further characterized in that the cohesive protruding end moiety of the oligonucleotide is 4 to 12 nucleotide length, and that the sequence of the cohesive protruding end moiety is complementary to the cohesive protruding end moiety in at least another oligonucleotide to such a degree as to form a double strand sequence showing a melting temperature that is equal to or higher than the body temperature in a physiological condition. Furthermore, the sol-like composition of (2-1) is further characterized in that the complementary base sequence moiety of the oligonucleotide is 8 to 45 nucleotide length, and the sequence of the complementary base sequence moiety is complementary to the complementary base sequence moiety in the other oligonucleotide to such a degree as to form a double strand sequence showing a melting temperature that is equal to or higher than the body temperature in a physiological condition. Herein, the physiological condition refers to a conditions of 37° C. and a salt concentration of 150 mM in terms of a NaCl concentration.

In (1-1), unlike (2-1), the salt concentration and the nucleic acid concentration are not limited, but the salt concentration and the nucleic acid concentration are kept low to such a degree that a gel is not formed at room temperature according to the nature of the nucleic acid monomers constituting thereof, and thus it exist as a sol.

The present invention can provide (1-1) and (2-1), that is, the followings:
the sol-like composition according to (1-1), for producing a gel in a living body, and
the sol-like composition according to (2-1), for producing a gel in a living body.

In the inventions according to (1-2) and (2-2), the applications of the sol-like compositions of (1-1) and (2-1) are limited to "production of a gel in a living body," and, specifically, the "nucleic acid monomer" and the "oligonucleotide" constituting the composition have a feature such that the "nucleic acid monomer" and the "oligonucleotide" are gelated in a physiological condition, that is, in the conditions of 37° C. and a salt concentration of 150 mM.

The present invention can provide (1-3) and (2-3), that is, the followings:
the sol-like composition according to (1-1) or (1-2), wherein the nucleic acid monomer has a sequence structure which binds to the complementary base sequence moiety in a complementary manner, and which is complementary to such a degree that the cohesive protruding end forms a double strand sequence showing a melting temperature that is equal to or higher than the body temperature in a physiological condition, and
the sol-like composition according to (2-1), wherein the cohesive protruding end includes a palindrome sequence structure.

In the invention of (2-3), the cohesive protruding end moiety forming a nucleic acid monomer and an oligonucleotide may have entirely the same palindrome sequence structure. The invention of (1-3) is characterized in that the nucleic acid monomer binds to a complementary base sequence moiety in a complementary manner in the invention of (1-1) or (1-2). Herein, binding in a complementary manner denotes that a complementary base sequence moiety in the nucleic acid monomer capable of forming the nucleic acid unit is complementary to a complementary base sequence moiety of another nucleic acid monomer capable of forming the same nucleic acid unit with at least 85% complementary, preferably 90% or more complementary, more preferably 95% or more complementary, and particularly preferably 100% complementary.

The present invention can provide (1-4) and (2-4), that is, the followings:
a method for producing a nucleic acid gel without using a nucleic acid linking enzyme by increasing a nucleic acid concentration and/or a salt concentration of the nucleic acid sol-like composition according to any one of (1-1) to (1-3), and
a method for producing a nucleic acid gel which does not contain a nucleic acid linking enzyme, the method comprising forming a gel by increasing the nucleic acid concentration of the sol-like composition according to (2-3) to 3.2/x (the number of bases in the protruding end moiety) mM or more and increasing the salt concentration to 640 mM/x (the number of bases in the protruding end moiety)–60 mM or more in terms of a NaCl concentration, respectively.

Both (1-4) and (2-4) relate to a method for producing a nucleic acid gel without using a nucleic acid linking enzyme by increasing the nucleic acid concentration and/or salt concentration of the nucleic acid sol-like composition of the present invention. The present invention is characterized in that a nucleic acid linking enzyme is not used in production of a nucleic acid gel. That is, each of the inventions of (1-4) and (2-4) is a method for producing a gel only by increasing the nucleic acid concentration and/or salt concentration of the nucleic acid sol-like composition of the present invention.

In (1-4), the nucleic acid concentration and/or the salt concentration for forming a gel is not particularly limited, and they can be appropriately selected by a person skilled in the art based on the nature of a nucleic acid monomer constituting a sol-like composition. The method for producing a gel of (2-4) includes increasing the nucleic acid concentration of the sol-like composition according to (2-3) to 3.2/x (the number of bases in the protruding end moiety) mM or more and increasing the salt concentration to 640 mM/x (the number of bases in the protruding end moiety)–60 mM or more in terms of a NaCl concentration, respectively. Herein, "x" and "in terms of a NaCl concentration" are the same as those described in the invention of (2-1).

The present invention can provide (1-5) and (2-5), that is, the followings:

a kit for producing a nucleic acid gel which does not contain a nucleic acid linking enzyme without using the nucleic acid linking enzyme, the kit independently comprising:
  a first sol-like composition which includes a first nucleic acid monomer according to (1-1) and which does not contain the nucleic acid linking enzyme; and
  a second sol-like composition which includes a second nucleic acid monomer according to (1-1) and which does not contain the nucleic acid linking enzyme, wherein
  a cohesive protruding end in the first nucleic acid monomer includes a first sequence;
  a cohesive protruding end in the second nucleic acid monomer includes a second sequence; and the first sequence and the second sequence are complementary to each other to such a degree as to form a double strand sequence which shows a melting temperature that is equal to or higher than the body temperature in a physiological condition, and a kit for producing a nucleic acid gel which does not contain a nucleic acid linking enzyme, the kit independently comprising:
  a first sol-like composition which contains the mixture of oligonucleotides according to (2-1) and which does not contain a nucleic acid linking enzyme; and
  a second sol-like composition which contains the mixture of oligonucleotides according to (2-1) and which does not contain a nucleic acid linking enzyme, wherein
  a cohesive protruding end moiety of the first oligonucleotide includes a first sequence;
  a cohesive protruding end moiety of the second oligonucleotide includes a second sequence; and
  the first sequence and the second sequence are complementary to each other to such a degree as to form a double strand sequence showing a melting temperature that is equal to or higher than the body temperature in a physiological condition.

(1-5) and (2-5) relate to a sol-like composition for forming a gel from two or more kinds of the nucleic acid units in (B).

Specifically, the invention of (1-5) relates to a kit for producing a nucleic acid gel which does not contain a nucleic acid linking enzyme, the kit independently including the first sol-like composition and the second sol-like composition, which are defined in (1-1) and are different from each other (these include first and second nucleic acid monomers which are different from each other and do not contain a nucleic acid linking enzyme). Furthermore, in the invention of (1-5), a cohesive protruding end in the first nucleic acid monomer includes a first sequence, a cohesive protruding end in the second nucleic acid monomer includes a second sequence. Herein, the first sequence and the second sequence are characterized in that they are complementary to each other to such a degree as to form a double strand sequence showing a melting temperature that is equal to or higher than the body temperature in a physiological condition. Note here that the expression "in a physiological condition" in the definition of the degree of the complementarity of the first sequence and the second sequence denotes the conditions of 37° C. and a NaCl concentration of 150 mM. The percentage of the complementarity is different depending upon the first sequence and the second sequence, that is, the length of the cohesive protruding end, but is preferably 90% or more complementary, further preferably 95% or more complementary, and particularly preferably 100% complementary.

Furthermore, the invention of (2-5) further limits the invention of (1-5), and the characteristic of the limitation is the same as in (2-1).

The present invention can provide (1-6) and (2-6), that is, the followings:

a method for producing a nucleic acid gel which does not contain a nucleic acid linking enzyme, the method comprising forming a gel by mixing the first sol-like composition and the second sol-like composition in the kit according to (1-5), and a method for producing a nucleic acid gel which does not contain a nucleic acid linking enzyme, the method comprising forming a gel by mixing the first sol-like composition and the second sol-like composition in the kit according to (2-5) in the condition in which the nucleic acid concentration is adjusted to 3.2/x (the number of bases in the protruding end moiety) mM or more and the salt concentration is adjusted to 640 mM/x (the number of bases in the protruding end moiety)–60 mM or more in terms of a NaCl concentration.

The inventions of (1-6) and (2-6) respectively relate to a method for producing a nucleic acid gel, which includes mixing the first sol-like composition and the second sol-like composition of (1-5) and (2-5) with each other. In the invention of (1-6), the nucleic acid concentration and/or the salt concentration for forming a gel are not particularly limited, and they can be appropriately determined by a person skilled in the art according to the nature of a nucleic acid monomer constituting two kinds of sol-like compositions. The method for producing a gel of (2-6) includes forming a gel by mixing the first sol-like composition and the second sol-like composition in the kit according to (2-5) in the condition in which the nucleic acid concentration is adjusted to 3.2/x (the number of bases in the protruding end moiety) mM or more and the salt concentration is adjusted to 640 mM/x (the number of bases in the protruding end moiety)–60 mM or more in terms of a NaCl concentration. Herein, "x" and "in terms of a NaCl concentration" are the same as those described in the invention of (2-1).

FIG. 11 shows the mechanisms of the methods of (1-6) and (2-6), but the mechanisms are not necessarily limited to the embodiment shown in this schematic view.

The present invention can provide (1-7) and (2-7), that is, the followings:

a kit for producing a nucleic acid gel which does not contain a nucleic acid linking enzyme without using the nucleic acid linking enzyme, the kit independently comprising:
  a first sol-like composition which includes a nucleic acid monomer according to (1-1) and which does not contain the nucleic acid linking enzyme; and
  a second sol-like composition which contains double strand nucleic acid having cohesive single strand protruding ends at both ends and which does not contain the nucleic acid linking enzyme, wherein
  a cohesive protruding end in the first nucleic acid monomer includes a first sequence;
  the protruding ends at both ends of the double strand nucleic acid include a second sequence; and
  the first sequence and the second sequence are complementary to each other to such a degree as to form a double strand sequence which shows a melting temperature that is equal to or higher than the body temperature in a physiological condition, and a kit for producing a nucleic acid gel which does not contain a nucleic acid linking enzyme, the kit independently comprising:
  a first sol-like composition which contains the mixture of oligonucleotides according to (2-1) and which does not contain a nucleic acid linking enzyme; and
  a second sol-like composition which does not contain a nucleic acid linking enzyme, and which contains nucleic acid having cohesive single strand protruding end moieties at both ends, and a double strand complementary base sequence moiety interposed therebetween;
  [in the second sol-like composition,
  the protruding end moiety has 4 to 12 nucleotide length and is a single strand nucleic acid moiety which is complementary to a cohesive protruding end moiety in the oligonucleotide in the first sol-like composition to such a degree as to form a double strand sequence showing a melting temperature that is equal to or higher than the body temperature in a physiological condition; and
  the complementary base sequence moiety has 8 to 45 nucleotide length and is a double strand nucleic acid moiety which is complementary to a complementary base sequence moiety in the oligonucleotide in the first sol-like composition to such a degree as to form a double strand sequence showing a melting temperature that is equal to or higher than the body temperature in a physiological condition], wherein
  a cohesive protruding end moiety of the oligonucleotide in the first sol-like composition includes a first sequence;
  the protruding end moieties at both ends of the complementary base sequence moiety made of the double strand includes a second sequence; and
  the first sequence and the second sequence are complementary to each other to such a degree as to form a double strand sequence showing a melting temperature that is equal to or higher than the body temperature in a physiological condition.

The invention of (1-7) is the same as the invention of (1-5) except that the "second nucleic acid monomer" included in the "second sol-like composition" in the invention of (1-5) is changed to the "double strand nucleic acid having cohesive single strand protruding ends at both ends". That is, the "nucleic acid unit" that can be formed of the "nucleic acid monomer" of the invention of (1-5) is changed to the "double strand nucleic acid having cohesive single strand protruding ends at both ends" when n is 2 in the above-mentioned schematic view.

The invention of (2-7) is the same as the invention of (2-5) except that the "second oligonucleotide" included in the "second sol-like composition" in the invention of (2-5) is changed to the "nucleic acid having cohesive single strand protruding end moieties at both ends, and a double strand complementary base sequence moiety between the protruding end moieties." That is, the "nucleic acid unit" that can be formed of the "oligonucleotide" of the invention of (2-5) is changed to "nucleic acid having cohesive single strand protruding end moieties at both ends, and a double strand complementary base sequence moiety between the protruding end moieties" when n is 2 in the above-mentioned schematic view. Furthermore, the invention of (2-7) limits, in the characteristic of the second sol-like composition, the "protruding end moiety" to the "protruding end moiety has 4 to 12 nucleotide length and is a single strand nucleic acid moiety which is complementary to a cohesive protruding end moiety in the oligonucleotide in the first sol-like composition to such a degree as to form a double strand sequence showing a melting temperature that is equal to or higher than the body temperature in a physiological condition," and limits the "complementary base sequence moiety" to the "the complementary base sequence moiety has 8 to 45 nucleotide length and is a double strand nucleic acid moiety which is complementary to a complementary base sequence moiety in the oligonucleotide in the first sol-like composition to such a degree as to form a double strand sequence showing a melting temperature that is equal to or higher than the body temperature in a physiological condition."

The present invention can provide (1-8) and (2-8), that is, the followings:
  a method for producing a nucleic acid gel which does not contain a nucleic acid linking enzyme, the method comprising forming gel by mixing the first sol-like composition and the second sol-like composition in the kit according to (1-7), and
  a method for producing a nucleic acid gel which does not contain a nucleic acid linking enzyme, the method comprising forming a gel by mixing the first sol-like composition and the second sol-like composition in the kit according to (2-7) in the condition in which the nucleic acid concentration is adjusted to 3.2/x (the number of bases in the protruding end moiety) mM or more and the salt concentration is adjusted to 640 mM/x (the number of bases in the protruding end moiety)−60 mM or more in terms of a NaCl concentration.

The inventions of (1-8) and (2-8) respectively relate to a method for producing a nucleic acid gel, which includes mixing the first sol-like composition and the second sol-like composition of (1-7) and (2-7) with each other. In the invention of (1-8), the nucleic acid concentration and/or the salt concentration for forming a gel are not particularly limited, and they can be appropriately determined by a person skilled in the art according to the nature of a nucleic acid monomer and a double strand nucleic acid constituting two kinds of sol-like compositions. The method for producing a gel of (2-8) includes forming a gel by mixing the first sol-like composition and the second sol-like composition in the kit according to (2-7) in the condition in which the nucleic acid concentration is adjusted to 3.2/x (the number of bases in the protruding end moiety) mM or more and the salt concentration is adjusted to 640 mM/x (the number of bases in the protruding end moiety)−60 mM or more in terms of a NaCl concentration. Herein, "x" and "in terms of a NaCl concentration" are the same as those described in the invention of (2-1).

FIG. 12 shows the mechanisms of the methods of (1-8) and (2-8), but the mechanisms are not necessarily limited to the embodiment shown in this schematic view.

The present invention can further provide (1-9) and (2-9), that is, the followings:
  a nucleic acid gel produced by the method according to any one of (1-4), (1-6) and (1-8), which does not contain a nucleic acid linking enzyme, and
  a nucleic acid gel produced by the method according to any one of (2-4), (2-6) and (2-8), which does not contain a nucleic acid linking enzyme.

The nucleic acid gels according to the inventions of (1-9) and (2-9) are characterized in that a nucleic acid linking enzyme is not contained.

The present invention can provide (1-10) and (2-10), that is, the followings:
  a method for producing a nucleic acid gel which encloses an encapsulated substance and which does not contain a nucleic acid linking enzyme, the method comprising adding the encapsulated substance to be enclosed in a gel before formation of the gel into a sol-like composition, in the method according to any one of (1-4), (1-6) and (1-8), and a method for producing a nucleic acid gel which encloses an encapsulated substance and which does not contain a nucleic acid linking enzyme, the method comprising adding the encapsulated substance to be enclosed in a gel before formation of the gel into a sol-like composition, in the method according to any one of (2-4), (2-6) and (2-8).

The inventions of (1-10) and (2-10) relate to a method for producing a nucleic acid gel which internally encloses an encapsulated substance and which does not contain a nucleic acid linking enzyme. The method further includes adding the encapsulated substance to be enclosed in a gel before formation of the gel into a sol-like composition, in the method for producing a nucleic acid gel of (1-4), (1-6) and (1-8) or (2-4), (2-6) and (2-8). The encapsulated substance is not particularly limited as long as the substance is intended to be internally enclosed in the gel except for the nucleic acid linking enzyme. Examples of the encapsulated substance include, but are not particularly limited to, DNA intercalators such as doxorubicin and daunomycin; peptides and peptide pharmaceutical agents such as insulin; protein antigens such as egg albumin and *Cryptomeria japonica* antigen; proteins and protein pharmaceutical agents such as a growth factor and cytokine; cells, genetically modified cells, and the like.

According to the inventions of (1-10) and (2-10), first, a sol is prepared, and an encapsulated substance is added thereto so as to increase, for example, the salt concentration and the nucleic acid concentration, thereby enabling a gel internally enclosing an encapsulated substance to be formed. Furthermore, the addition amount of the encapsulated substance is not particularly limited, and the encapsulated substance can be enclosed even when the amount may be the same level as the weight of the gel.

The present invention can provide (1-11) and (2-11), that is, the followings:

the method according to (1-10), wherein the encapsulated substance is selected from a low-molecular compound, a protein, and a cell, and the method according to (2-10), wherein the encapsulated substance is selected from a low-molecular compound, a protein, and a cell.

The inventions of (1-11) and (2-11) respectively limit the encapsulated substances in the inventions of (1-10) and (2-10) to a low-molecular compound, a protein, and a cell; however, the protein is not a nucleic acid linking enzyme. Examples of the low-molecular compound, the protein, and the cell are as mentioned above.

The present invention can provide (1-12) and (2-12), that is, the followings:

a nucleic acid gel produced by the method according to (1-10) or (1-11), which contains an encapsulated substance and which does not contain a nucleic acid linking enzyme, and a nucleic acid gel produced by the method according to (2-10) or (2-11), which contains an encapsulated substance and which does not contain a nucleic acid linking enzyme.

The inventions of (1-12) and (2-12) relate to a nucleic acid gel produced by the method according to (1-10), (1-11), (2-10) or (2-11), which contains an encapsulated substance and which does not contain a nucleic acid linking enzyme. The nucleic acid gel is a nucleic acid gel internally including a desired encapsulated substance in the complicated fine structure of the gel, which makes it possible, for example, to allow the encapsulated substance to gradually release in a living body.

The present invention can provide (1-13), that is, the following:

the sol-like composition according to (1-1) or (1-2), wherein the nucleic acid monomer binds to a complementary base sequence moiety in a complementary manner, and the cohesive protruding end includes a palindrome sequence structure.

The present invention can provide (3-1) to (3-4), that is, the followings:

(3-1): the nucleic acid sol-like composition, method, kit, or nucleic acid gel according to any one of (1-12) and (2-12), wherein the nucleic acid monomer includes a CpG motif, (3-2): the nucleic acid sol-like composition, method, kit, or nucleic acid gel according to any one of (1-12), (2-12) and (3-1), wherein the number of kinds of the nucleic acid monomers is 3 to 8, (3-3): the sol-like composition for producing an immunological adjuvant according to any one of (1-1) to (1-3) and (2-1) to (2-3), wherein the nucleic acid monomer includes a CpG motif, and (3-4): an immunological adjuvant comprising the nucleic acid gel according to any one of (1-9), (1-12), (2-9) and (2-12), wherein the nucleic acid monomer includes a CpG motif.

EXAMPLES

Hereinafter, the present invention will be described in detail with reference to Examples and the drawings, but Examples and the drawings are not intended to limit the scope of the present invention.

Materials and Methods

Chemical Substances

A RPMI1640 medium was supplied from Nissui Pharmaceutical Co., Ltd., Tokyo, Japan. Fetus bovine serum (FBS) was supplied from Equitech-Bio, Inc (Kerrville, Tex., USA). Opti-MEM (Opti-modified Eagle's medium) was purchased from Invitrogen (Carlsbad, Calif., USA). 20-bp DNA ladder was purchased from Takara Bio Inc. Otsu, Japan. All other reagents and substances are available ones in the highest grade, and they were used without further purification.

Oligodeoxy Nucleotide (Also Referred to as ODN)

Phosphodiester oligodeoxy nucleotide (ODN) was purchased from Integrated DNA Technologies, Inc. (Coralville, Iowa, USA). Sequences of ODN are listed in Table 1. In Table 1, each ODN was named as "Xpodna-Y-Z". Herein, X represents tri (3), tetra (4), penta (5), hexa (6) or octa (8), Y represents numbering of each Xpodna (1, 2, or the like), and Z represents numbering of ODN constituting each Xpodna. In study on cell uptake, ODN whose 5'-end was labeled with Alexa Fluor 488 was purchased from JBioS (Saitama, Japan), and used for preparation of fluorescence-labeled Polypodna.

Preparation of ODN Solution (Also Referred to as Polypodna)

Each ODN was dissolved in a TE buffer (10 mM Tris-HCl, 1 mM ethylenediaminetetraacetic acid (EDTA), pH 8) containing 5 mM sodium chloride (NaCl). Then, the mixture was incubated at 95° C. for 5 minutes, at 65° C. for 2 minutes, and at 62° C. for 1 minute by using a thermal cycler, and then the mixture was gradually cooled to 4° C. The product was analyzed with electrophoresis by subjecting the product to 12% polyacrylamide gel electrophoresis (PAGE) at room temperature (about 22 to 25° C.), at 200 V and for 45 minutes.

Evaluation of Gel Formation of Gel and Gel Strength

A NaCl solution was added to an ODN solution (polypodna) such that the final $Na^+$ concentration was 5 to 150 mM. The gel formation and the gel strength were measured by a gel strength analyzer (gel strength meter, Nakayamadenki Co., Ltd, Osaka).

Observation of DNA Hydrogel Under Scanning Electron Microscope

In order to observe an internal structure of a DNA hydrogel, the DNA hydrogel was fixed overnight with 2% glutaraldehyde at room temperature, and subjected to dehydration by using ethanol whose concentration was gradually increased. Then, the ethanol was substituted with buthyl alcohol, to lyophilize the DNA hydrogel. The dried material was cut with a knife, and the internal structure of the DNA hydrogel was observed under a field emission-type scanning electron microscope (FE-SEM: 54700, HITACHI, Japan).

TABLE 1

Names and sequences of oligonucleotides used in Examples

| Name | Sequence (SEQ ID No.) | Remarks |
|---|---|---|
| Tripodna(4-18-18)-1-01 | acgt tcgtcaacgtctgtgctc tcacgttgacgctgtcga (1) | |
| Tripodna(4-18-18)-1-02 | acgt tcgacagcgtcaacgtga aacgtgaagcgtctgcga (2) | Tetrapodna(4-18-18)-1-02, Pentapodna(4-18-18)-1-02, Hexapodna(4-18-18)-1-02, Octapodna(4-18-18)-1-03 |
| Tripodna(4-18-18)-1-03 | acgt tcgcagacgcttcacgtt gagcacagacgttgacga (3) | Pentapodna(4-18-18)-1-03, Hexapodna(4-18-18)-1-03, Octapodna(4-18-18)-1-04 |
| Tetrapodna(4-18-18)-1-01 | acgt tcgctgacgttgcagaca tcacgttgacgctgtcga (4) | Pentapodna(4-18-18)-1-01, Hexapodna(4-18-18)-1-01 |
| Tetrapodna(4-18-18)-1-03 | acgt tcgcagacgcttcacgtt gcagacagacgttgacga (5) | |
| Tetrapodna(4-18-18)-1-04 | acgt tcgtcaacgtctgtctgc tgtctgcaacgtcagcga (6) | |
| Pentapodna(4-18-18)-1-04 | acgt tcgtcaacgtctgtgctc gcagcgtcttaacgtcga (7) | Hexapodna(4-18-18)-1-04, Octapodna(4-18-18)-1-05 |
| Pentapodna(4-18-18)-1-05 | acgt tcgacgttaagacgctgc tgtctgcaacgtcagcga (8) | |
| Hexapodna(4-18-18)-1-05 | acgt tcgacgttaagacgctgc agacgttcaggactacga (9) | Octapodna(4-18-18)-1-06 |
| Hexapodna(4-18-18)-1-06 | acgt tcgtagtactgaacgtct tgtctgcaacgtcagcga (10) | Octapodna(4-18-18)-1-07 |
| Octapodna(4-18-18)-1-01 | acgt tcgatccagacgttgtag cctgacgtcgtacatcga (11) | |
| Octapodna(4-18-18)-1-02 | acgt tcgatgtacgacgtcagg tcacgttgacgctgtcga (12) | |
| Octapodna(4-18-18)-1-08 | acgt tcgctgacgttgcagaca ctacaacgtctggatcga (13) | |
| Tetrapodna(4-18-18)-2-01 | agct aggcaccgtagtcaatcg ccgatgtgtccaaagcct (14) | Not containing CpG |
| Tetrapodna(4-18-18)-2-02 | agct aggctttggacacatcgg tgctcctaccgtactcct (15) | Not containing CpG |
| Tetrapodna(4-18-18)-2-03 | agct aggagtacggtaggagca gtttcggcatgtccacct (16) | Not containing CpG |
| Tetrapodna(4-18-18)-2-04 | agct aggtggacatgccgaaac cgattgactacggtgcct (17) | Not containing CpG |
| Tetrapodna(6-17-17)-1-01 | aacgtt tacgcacgacatcagcg tctggacgcttcgtcga (18) | |
| Tetrapodna(6-17-17)-1-02 | aacgtt tcgacgaagcgtccaga tctcgtcaacgctgcga (19) | |
| Tetrapodna(6-17-17)-1-03 | aacgtt tcgcagcgttgacgaga cagacgctgtgacgcta (20) | |
| Tetrapodna(6-17-17)-1-04 | aacgtt tagcgtcacagcgtctg cgctgatgtcgtgcgta (21) | |
| Tetrapodna(8-16-16)-1-01 | acgtacgt tagcacgacatcagcg tctgacgcttcgtcga (22) | |
| Tetrapodna(8-16-16)-1-02 | acgtacgt tcgacgaagcgtcaga tctcgtcaacgctgca (23) | |
| Tetrapodna(8-16-16)-1-03 | acgtacgt tgcagcgttgacgaga cagacgcttgacgcta (24) | |
| Tetrapodna(8-16-16)-1-04 | acgtacgt tagcgtcaagcgtctg cgctgatgtcgtgcta (25) | |
| Tetrapodna(10-15-15)-1-01 | acgttaacgt tgcacgacatcagcg tctgacgctcgtcga (26) | |
| Tetrapodna(10-15-15)-1-02 | acgttaacgt tcgacgagcgtcaga tctcgcaacgctgca (27) | |
| Tetrapodna(10-15-15)-1-03 | acgttaacgt tgcagcgttgcgaga cagacgcttgacgca (28) | |
| Tetrapodna(10-15-15)-1-04 | acgttaacgt tgcgtcaagcgtctg cgctgatgtcgtgca (29) | |
| Tetrapodna(12-14-14)-1-01 | acgtcatgacgt tgcacgacatcacgt tgacgctcgtcga (30) | |

TABLE 1-continued

Names and sequences of oligonucleotides used in Examples

| | | |
|---|---|---|
| Tetrapodna(12-14-14)-1-02 | acgtcatgacgt tcgacgagcgtcaat ctcgcaacgtgca (31) | |
| Tetrapodna(12-14-14)-1-03 | acgtcatgacgt tgcacgttgcgagac agacgcttgacga (32) | |
| Tetrapodna(12-14-14)-1-04 | acgtcatgacgt tcgtcaagcgtctgc gtgatgtcgtgca (33) | |
| Mixed type (A + B) | | |
| Mix-1-A1 | | |
| Tetrapodna(12-14-14)-2-01 | tcagagtcagtc tgcacgacatcacg ttgacgctcgtcga (34) | |
| Tetrapodna(12-14-14)-2-02 | tcagagtcagtc tcgacgagcgtcaa tctcgcaacgtgca (35) | |
| Tetrapodna(12-14-14)-2-03 | tcagagtcagtc tgcacgttgcgaga cagacgcttgacga (36) | |
| Tetrapodna(12-14-14)-2-04 | tcagagtcagtc tcgtcaagcgtctg cgtgatgtcgtgca (37) | |
| Mix-1-B1 | | |
| Tetrapodna(12-14-14)-3-01 | gactgactctga tgcacgacatcacg ttgacgctcgtcga (38) | |
| Tetrapodna(12-14-14)-3-02 | gactgactctga tcgacgagcgtcaa tctcgcaacgtgca (39) | |
| Tetrapodna(12-14-14)-3-03 | gactgactctga tgcacgttgcgaga cagacgcttgacga (40) | |
| Tetrapodna(12-14-14)-3-04 | gactgactctga tcgtcaagcgtctg cgtgatgtcgtgca (41) | |
| Mix-1-B2 (dsDNA) | | |
| Ds(12-14)-1-01 | gactgactctga acgtcagcgtta (42) | |
| Ds(12-14)-1-02 | gactgactctga taacgctgacgt (43) | |
| Mix-2-A1 | | |
| Hexapodna(8-16-16)-2-01 | tcctgacg ttgctagacgctgtca gcacgtcgtagtgcaa (44) | Tetrapodna(8-16-16)-2-01 |
| Hexapodna(8-16-16)-2-02 | tcctgacg ttgcactacgacgtgc agcagacgtcgatcaa (45) | Tetrapodna(8-16-16)-2-02 |
| Hexapodna(8-16-16)-2-03 | tcctgacg ttgatcgacgtctgct tgacgctcagctgcaa (46) | Tetrapodna(8-16-16)-2-03 |
| Hexapodna(8-16-16)-2-04 | tcctgacg ttgcagctgagcgtca gacgctgatctagcaa (47) | |
| Hexapodna(8-16-16)-2-05 | tcctgacg ttgctagatcagcgtc ctcacgttgactacaa (48) | |
| Hexapodna(8-16-16)-2-06 | tcctgacg ttgtagtaaacgtgag tgacagcgtatagaaa (49) | |
| Mix-2-A2 | | |
| Tetrapodna(8-16-16)-2-04 | tcctgacg ttgcagctgagcgtca tgacagcgtctagcaa (50) | |
| Mix-2-B1 | | |
| Hexapodna(8-16-16)-3-01 | cgtcagga cgttgaatccatgacg ttgtatgactgcaacg (51) | Tetrapodna(8-16-16)-3-01 |
| Hexapodna(8-16-16)-3-02 | cgtcagga cgttgcagtcatacaa tcctgacgctctgacg (52) | Tetrapodna(8-16-16)-3-02 |
| Hexapodna(8-16-16)-3-03 | cgtcagga cgtcagagcgtcagga cgttcatcagtatacg (53) | Tetrapodna(8-16-16)-3-03 |
| Hexapodna(8-16-16)-3-04 | cgtcagga cgtatactgatgaacg aagtgacgtctcaacg (54) | |
| Hexapodna(8-16-16)-3-05 | cgtcagga cgttgagacgtcactt atcgacgtctgagacg (55) | |
| Hexapodna(8-16-16)-3-06 | cgtcagga cgtctcagacgtagat cgtcatggattcaacg (56) | |
| Mix-2-B2 | | |
| Tetrapodna(8-16-16)-3-04 | cgtcagga cgttaactgatgaacg cgtcatggattcaacg (57) | |
| Tetrapodna(I) | | |
| Tetra-I-01 | AGTC TCGCTGACGTTGCAGACA TCACGTTGACGCTGTCGA | (SEQ ID No. 58) |
| Tetra-I-02 | AGTC TCGACAGCGTCAACGTGA AACGTGAAGCGTCTGCGA | (SEQ ID No. 59) |

TABLE 1-continued

Names and sequences of oligonucleotides used in Examples

| Tetra-I-03 | AGTC TCGCAGACGCTTCACGTT GCAGACAGACGTTGACGA | (SEQ ID No. 60) |
| Tetra-I-04 | AGTC TCGTCAACGTCTGTCTGC TGTCTGCAACGTCAGCGA | (SEQ ID No. 61) |

| Name | Sequence (5' → 3') (SEQ ID No.) |
|---|---|
| Hexapodna (8-16-16)-4-01 | gcagacga cgttgaatccatgacg ttgtatgactgcaacg (62) |
| Hexapodna (8-16-16)-4-02 | gcagacga cgttgcagtcatacaa tcctgacgctctgacg (63) |
| Hexapodna (8-16-16)-4-03 | gcagacga cgtcagagcgtcagga cgttcatcagtatacg (64) |
| Hexapodna (8-16-16)-4-04 | gcagacga cgtatactgatgaacg aagtgacgtctcaacg (65) |
| Hexapodna (8-16-16)-4-05 | gcagacga cgttgagacgtcactt atcgacgtctgagacg (66) |
| Hexapodna (8-16-16)-4-06 | gcagacga cgtctcagacgtcgat cgtcatggattcaacg (67) |
| Hexapodna (8-16-16)-5-01 | tcctgagc ttgctagagcctgtca ggagcagctagtgcaa (68) |
| Hexapodna (8-16-16)-5-02 | tcctgagc ttgcactagctgctcc agcagagctcgatcaa (69) |
| Hexapodna (8-16-16)-5-03 | tcctgagc ttgatcgagctctgct tgagcctcagctgcaa (70) |
| Hexapodna (8-16-16)-5-04 | tcctgagc ttgcagctgaggctca gagcctgatctagcaa (71) |
| Hexapodna (8-16-16)-5-05 | tcctgagc ttgctagatcaggctc ctcagcttgactacaa (72) |
| Hexapodna (8-16-16)-5-06 | tcctgagc ttgtagtcaagctgag tgacaggctctagcaa (73) |
| Hexapodna (8-16-16)-6-01 | gctcagga gcttgaatccatgagc ttgtatgactgcaagc (74) |
| Hexapodna (8-16-16)-6-02 | gctcagga gcttgcagtcatacaa tcctgagcctctgagc (75) |
| Hexapodna (8-16-16)-6-03 | gctcagga gctcagaggctcagga gcttcatcagtatagc (76) |
| Hexapodna (8-16-16)-6-04 | gctcagga gctatactgatgaagc aagtgagctctcaagc (77) |
| Hexapodna (8-16-16)-6-05 | gctcagga gcttgagagctcactt atgcagctctgagagc (78) |
| Hexapodna (8-16-16)-6-06 | gctcagga gctctcagagctgcat gctcatggattcaagc (79) |
| Hexapodna (8-16-16)-7-01 | gctgtcca gcttgaatccatgagc ttgtatgactgcaagc (80) |
| Hexapodna (8-16-16)-7-02 | gctgtcca gcttgcagtcatacaa tcctgagcctctgagc (81) |
| Hexapodna (8-16-16)-7-03 | gctgtcca gctcagaggctcagga gcttcatcagtatagc (82) |
| Hexapodna (8-16-16)-7-04 | gctgtcca gctatactgatgaagc aagtgagctctcaagc (83) |
| Hexapodna (8-16-16)-7-05 | gctgtcca gcttgagagctcactt atgcagctctgagagc (84) |
| Hexapodna (8-16-16)-7-06 | gctgtcca gctctcagagctgcat gctcatggattcaagc (85) |

| Name | Sequence (5' → 3') (SEQ ID No.) | Remarks |
|---|---|---|
| Tripodna (0-18-18)-1-01 | tcgtcaacgtctgtgctctcacgttgacgctgtcga (86) | |
| Tripodna (0-18-18)-1-02 | tcgacagcgtcaacgtgaaacgtgaagcgtctgcga (87) | Tetrapodna (0-18-18)-1-02, pentapodna (0-18-18)-1-02, hexapodna (0-18-18)-1-02 |
| Tripodna (0-18-18)-1-03 | tcgcagacgcttcacgttgagcacagacgttgacga (88) | Pentapodna (0-18-18)-1-03, hexapodna (0-18-18)-1-03 |
| Tetrapodna (0-18-18)-1-01 | tcgctgacgttgcagacatcacgttgacgctgtcga (89) | Pentapodna (0-18-18)-1-01, hexapodna (0-18-18)-1-01 |
| Tetrapodna (0-18-18)-1-03 | tcgcagacgcttcacgttgcagacagacgttgacga (90) | |
| Tetrapodna (0-18-18)-1-04 | tcgtcaacgtctgtctgctgtctgcaacgtcagcga (91) | |
| Pentapodna (0-18-18)-1-04 | tcgtcaacgtctgtgctcgcagcgtcttaacgtcga (92) | Hexapodna (0-18-18)-1-04 |

TABLE 1-continued

Names and sequences of oligonucleotides used in Examples

| Name | Sequence (5' → 3') (SEQ ID No.) | Note |
|---|---|---|
| Pentapodna (0-18-18)-1-05 | tcgacgttaagacgctgctgtctgcaacgtcagcga (93) | |
| Hexapodna (0-18-18)-1-05 | tcgacgttaagacgctgcagacgttcaggactacga (94) | |
| Hexapodna (0-18-18)-1-06 | tcgtagtcctgaacgtcttgtctgcaacgtcagcga (95) | |

| Name | Sequence (5' → 3') (SEQ ID No.) | Note |
|---|---|---|
| Tripodna (0-18-18)-2-01 | TCGTCGTTCCGTCGTTACACTGCTCTGGCGGTCGTT (96) | Tetrapodna (0-18-18)-2-01, pentapodna (0-18-18)-2-01, hexapodna (0-18-18)-2-01 |
| Tripodna (0-18-18)-2-02 | AACGACCGCCAGAGCAGTCGTGTCGTACTACGACGA (97) | Tetrapodna (0-18-18)-2-02, pentapodna (0-18-18)-2-02, hexapodna (0-18-18)-2-02 |
| Tripodna (0-18-18)-2-03 | TCGTCGTAGTACGACACGGTAACGACGGAACGACGA (98) | |
| Tetrapodna (0-18-18)-2-03 | TCGTCGTAGTACGACACGGTCGTAAGCCTGGTCGTA (99) | Pentapodna (0-18-18)-2-03, hexapodna (0-18-18)-2-03 |
| Tetrapodna (0-18-18)-2-04 | TACGACCAGGCTTACGACGTAACGACGGAACGACGA (100) | |
| Pentapodna (0-18-18)-2-04 | TACGACCAGGCTTACGACAGTCTAGCTGATCGACGA (101) | Hexapodna (0-18-18)-2-04 |
| Pentapodna (0-18-18)-2-05 | TCGTCGATCAGCTAGACTGTAACGACGGAACGACGA (102) | |
| Hexapodna (0-18-18)-2-05 | TCGTCGATCAGCTAGACTGCTGTCGATGCCAACGAC (103) | |
| Hexapodna (0-18-18)-2-06 | GTCGTTGGCATCGACAGCGTAACGACGGAACGACGA (104) | |

| ODN | Sequence (5' → 3') (SEQ ID No.) |
|---|---|
| Tripodna$_{30}$-1 | CTAGCGTTGCTAGTGGTGTCCAAACGCTAG (105) |
| Tripodna$_{30}$-2 | CTAGCGTTTGGACACTCAGCCTAACGCTAG (106) |
| Tripodna$_{30}$-3 | CTAGCGTTAGGCTGACACTAGCAACGCTAG (107) |
| ssDNA$_{36}$, dsDNA$_{36}$-1, Tetrapodna$_{36}$-1, Pentapodna$_{36}$-1, Hexapodna$_{36}$-1 | TCGCTGACGTTGCAGACATCACGTTGACGCTGTCGA (108) |
| dsDNA$_{36}$-2 | TCGACAGCGTCAACGTGATGTCTGCAACGTCAGCGA (109) |
| Tripodna$_{36}$-1 | TCGTCAACGTCTGTGCTCTCACGTTGACGCTGTCGA (110) |
| Tripodna$_{36}$-2, Tetrapodna$_{36}$-2, Pentapodna$_{36}$-2, Hexapodna$_{36}$-2, Octapodna$_{36}$-2, Dodecapodna$_{36}$-2 | TCGACAGCGTCAACGTGAAACGTGAAGCGTCTGCGA (111) |
| Tripodna$_{36}$-3, Pentapodna$_{36}$-3, Hexapodna$_{36}$-3, Octapodna$_{36}$-3, Dodecapodna$_{36}$-3 | TCGCAGACGCTTCACGTTGAGCACAGACGTTGACGA (112) |
| Tetrapodna$_{36}$-3 | TCGCAGACGCTTCACGTTGCAGACAGACGTTGACGA (113) |
| Tetrapodna$_{36}$-4 | TCGTCAACGTCTGTCTGCTGTCTGCAACGTCAGCGA (114) |
| Pentapodna$_{36}$-4, Hexapodna$_{36}$-4, Octapodna$_{36}$-4, Dodecapodna$_{36}$-4 | TCGTCAACGTCTGTGCTCGCAGCGTCTTAACGTCGA (115) |
| Pentapodna$_{36}$-5 | TCGACGTTAAGACGCTGCTGTCTGCAACGTCAGCGA (116) |

TABLE 1-continued

Names and sequences of oligonucleotides used in Examples

| | |
|---|---|
| Hexapodna$_{36}$-5, Octapodna$_{36}$-5, Dodecapodna$_{36}$-5 | TCGACGTTAAGACGCTGCAGACGTTCAGGACTACGA (117) |
| Hexapodna$_{36}$-6, Octapodna$_{36}$-6, Dodecapodna$_{36}$-6 | TCGTAGTCCTGAACGTCTTGTCTGCAACGTCAGCGA (118) |
| Octapodna$_{36}$-1 | TCGATGTACGACGTCAGGTCACGTTGACGCTGTCGA (119) |
| Octapodna$_{36}$-7, Dodecapodna$_{36}$-7 | TCGCTGACGTTGCAGACACTACAACGTCTGGATCGA (120) |
| Octapodna$_{36}$-8 | TCGATCCAGACGTTGTAGCCTGACGTCGTACATCGA (121) |
| Dodecapodna$_{36}$-1 | TCGATGTACGACGTCAGATCACGTTGACGCTGTCGA (122) |
| Dodecapodna$_{36}$-8 | TCGATCCAGACGTTGTAGAACGTCGACTCAGATCGA (123) |
| Dodecapodna$_{36}$-9 | TCGATCTGAGTCGACGTTATACAACGCCTGGATCGA (124) |
| Dodecapodna$_{36}$-10 | TCGATCCAGGCGTTGTATCTATCCACACGCTGACGA (125) |
| Dodecapodna$_{36}$-11 | TCGTCAGCGTGTGGATAGGTCTCCAGACGTCATCGA (126) |
| Dodecapodna$_{36}$-12 | TCGATGACGTCTGGAGACTCTGACGTCGTACATCGA (127) |
| Hexapodna$_{40}$-1 | CTGACGTTCTGCTGCAGACATCAGCTTGAGCCTGTGCAAG (128) |
| Hexapodna$_{40}$-2 | CTTGCACAGGCTCAAGCTGAAAGCTGGTGCAGAACGTCAG (129) |
| Hexapodna$_{40}$-3 | CTGACGTTCTGCACCAGCTTGAGCACAGAGCTTGAGCAAG (130) |
| Hexapodna$_{40}$-4 | CTTGCTCAAGCTCTGTGCTCGCAGGCTCTTAGAACGTCAG (131) |
| Hexapodna$_{40}$-5 | CTGACGTTCTAAGAGCCTGCAGAGCTTCAGGACTAGCAAG (132) |
| Hexapodna$_{40}$-6 | CTTGCTAGTCCTGAAGCTCTTGTCTGCAGCAGAACGTCAG (133) |
| Pentapodna$_{48}$-1 | CTGACGTTCTGCTGCAGACAGTCATCAGTCAGCTTGAGCCTGTGCAAG (134) |
| Pentapodna$_{48}$-2 | CTTGCACAGGCTCAAGCTGACTGAAGCTAAGCTGGTGCAGAACGTCAG (135) |
| Pentapodna$_{48}$-3 | CTGACGTTCTGCACCAGCTTAGCTGACTGAGCACAGAGCTTGAGCAAG (136) |
| Pentapodna$_{48}$-4 | CTTGCTCAAGCTCTGTGCTCAGTCGCATGCAGGCTCTTAGAACGTCAG (137) |
| Pentapodna$_{48}$-5 | CTGACGTTCTAAGAGCCTGCATGCTGACTGTCTGCAGCAGAACGTCAG (138) |
| Tripodna$_{60}$-1 | CTAGCGTTGCTAGTGCTAGCGTTGCTAGTGGTGTCCAAACGCTAGGTGTCCAAACGCTAG (139) |
| Tripodna$_{60}$-2 | CTAGCGTTTGGACACCTAGCGTTTGGACACTCAGCCTAACGCTAGTCAGCCTAACGCTAG (140) |
| Tripodna$_{60}$-3 | CTAGCGTTAGGCTGACTAGCGTTAGGCTGACACTAGCAACGCTAGCACTAGCAACGCTAG (141) |
| Tetrapodna$_{60}$-1 | CTGACGTTCTGCTGCAGACAGTCACAGTCATCAGTGTCAGTCAGCTTGAGCCTGTGCAAG (142) |

TABLE 1-continued

Names and sequences of oligonucleotides used in Examples

| | |
|---|---|
| Tetrapodna$_{60}$-2 | CTTGCACAGGCTCAAGCTGACTGACACTGAAGCTGC<br>AGCTAAGCTGGTGCAGAACGTCAG (143) |
| Tetrapodna$_{60}$-3 | CTGACGTTCTGCACCAGCTTAGCTGCAGCTGCACTGG<br>CATGCAGGCTCTTAGAACGTCAG (144) |
| Tetrapodna$_{60}$-4 | CTGACGTTCTAAGAGCCTGCATGCCAGTGCTGACTGT<br>GACTGTCTGCAGCAGAACGTCAG (145) |
| Tripodna$_{80}$-1 | CTGACGTTCTGCTGCAGACAGTCACAGTCAGCTCCA<br>GTCAAGCTGCATGAAGCTGCAGCTAAGCTGGTGCAG<br>AACGTCAG (146) |
| Tripodna$_{80}$-2 | CTGACGTTCTGCACCAGCTTAGCTGCAGCTTCATGCA<br>GCTGCACTGCATTGCACTGGCATGCAGGCTCTTAGAA<br>CGTCAG (147) |
| Tripodna$_{80}$-3 | CTGACGTTCTAAGAGCCTGCATGCCAGTGCAATGCAG<br>TGCTGACTGGAGCTGACTGTGACTGTCTGCAGCAGA<br>ACGTCAG (148) |
| Tripodna$_{90}$-1, Octapodna$_{90}$-7 | CTAGCGTTGCTAGTGCTAGCGTTGCTAGTGCTAGCGT<br>TGCTAGTGGTGTCCAAACGCTAGGTGTCCAAACGCTA<br>GGTGTCCAAACGCTAG (149) |
| Tripodna$_{90}$-2 | CTAGCGTTTGGACACCTAGCGTTTGGACACCTAGCGT<br>TTGGACACTCAGCCTAACGCTAGTCAGCCTAACGCTA<br>GTCAGCCTAACGCTAG (150) |
| Tripodna$_{90}$-3 | CTAGCGTTAGGCTGACTAGCGTTAGGCTGACTAGCGT<br>TAGGCTGACACTAGCAACGCTAGCACTAGCAACGCTA<br>GCACTAGCAACGCTAG (151) |
| Tetrapodna$_{90}$-1, Pentapodna$_{90}$-1,<br>Hexapodna$_{90}$-1, Octapodna$_{90}$-1 | CTGACGTTGCAGACACTGACGTTGCAGACACTGACG<br>TTGCAGACATCACGTTGACGCTGTTCACGTTGACGCT<br>GTTCACGTTGACGCTGT (152) |
| Tetrapodna$_{90}$-2, Pentapodna$_{90}$-2,<br>Hexapodna$_{90}$-2, Octapodna$_{90}$-2 | ACAGCGTCAACGTGAACAGCGTCAACGTGAACAGCG<br>TCAACGTGAAACGTGAAGCGTCTGAACGTGAAGCGT<br>CTGAACGTGAAGCGTCTG (153) |
| Tetrapodna$_{90}$-3 | CAGACGCTTCACGTTCAGACGCTTCACGTTCAGACG<br>CTTCACGTTGCAGACAGACGTTGAGCAGACAGACGT<br>TGAGCAGACAGACGTTGA (154) |
| Tetrapodna$_{90}$-4 | TCAACGTCTGTCTGCTCAACGTCTGTCTGCTCAACGT<br>CTGTCTGCTGTCTGCAACGTCAGTGTCTGCAACGTCA<br>GTGTCTGCAACGTCAG (155) |
| Pentapodna$_{90}$-3, Hexapodna$_{90}$-3,<br>Octapodna$_{90}$-3 | CAGACGCTTCACGTTCAGACGCTTCACGTTCAGACG<br>CTTCACGTTGAGCACAGACGTTGAGAGCACAGACGT<br>TGAGAGCACAGACGTTGA (156) |
| Pentapodna$_{90}$-4, Hexapodna$_{90}$-4,<br>Octapodna$_{90}$-4 | TCAACGTCTGTGCTCTCAACGTCTGTGCTCTCAACGT<br>CTGTGCTCGCAGCGTCTTAACGTGCAGCGTCTTAACG<br>TGCAGCGTCTTAACGT (157) |
| Pentapodna$_{90}$-5 | ACGTTAAGACGCTGCACGTTAAGACGCTGCACGTTA<br>AGACGCTGCTGTCTGCAACGTCAGTGTCTGCAACGT<br>CAGTGTCTGCAACGTCAG (158) |
| Hexapodna$_{90}$-5, Octapodna$_{90}$-5 | ACGTTAAGACGCTGCACGTTAAGACGCTGCACGTTA<br>AGACGCTGCAGACGTTCAGGACTAAGACGTTCAGGA<br>CTAAGACGTTCAGGACTA (159) |
| Hexapodna$_{90}$-6 | TAGTCCTGAACGTCTTAGTCCTGAACGTCTTAGTCCT<br>GAACGTCTTGTCTGCAACGTCAGTGTCTGCAACGTCA<br>GTGTCTGCAACGTCAG (160) |
| Octapodna$_{90}$-6 | TAGTCCTGAACGTCTTAGTCCTGAACGTCTTAGTCCT<br>GAACGTCTCACTAGCAACGCTAGCACTAGCAACGCT<br>AGCACTAGCAACGCTAG (161) |

TABLE 1-continued

| \multicolumn{2}{l}{Names and sequences of oligonucleotides used in Examples} | |
|---|---|
| Octapodna$_{90}$-8 | CTAGCGTTTGGACACCTAGCGTTTGGACACCTAGCGT TTGGACACTGTCTGCAACGTCAGTGTCTGCAACGTCA GTGTCTGCAACGTCAG (162) |
| A$_{36}$ | AAAAAAAAAAAAAAAAAAAAAAAAAAAAAAAAAAAA (163) |
| (CG)$_6$ | CGCGCGCGCGCG (164) |

In the tables, XXXpodnay-Z as a name of each ODN (herein, XXX denotes Tri, Tetra, Penta or the like; and y and Z represent numerical values) means that the sequence is ODN for producing XXXpodnay. For example, Tripodna30 is produced by Tripodna 30-1, Tripodna 30-2 and Tripodna 30-3.

Example 1

(1-1) Formation of Hydrogel Composed of DNA

A structure to be a hydrogel (a nucleic acid monomer and an estimated nucleic acid unit) in conditions at room temperature, at 5 mM to 150 mM sodium chloride concentration (150 mM is substantially physiological concentration), and not containing a DNA ligase was elucidated. At this time, it was found that gelation occurred at milder conditions (low salt concentration) by increasing the number of nucleic acid monomers that were, thought to be capable of constituting the nucleic acid unit. For convenience, nucleic acid units estimated to be formed according to the number of nucleic acid monomers capable of constituting the nucleic acid unit were represented by xxxpodna (xxxpod-like structure forming nucleic acid, xxx is substituted by tri (3), tetra (4) and the like, according to the number of nucleic acid monomers capable of constituting the nucleic acid unit). In Table 2 described below, xxxpodna is an estimated nucleic acid unit, and each of xxx-Y-N is a nucleic acid monomer that can be a constituent element of the nucleic acid unit (xxxpodna) which is mentioned above thereof. When the descriptions of Ys are different from each other, different nucleic acid units can be formed. N denotes numbering of nucleic acid monomers constituting each of the estimated nucleic acid units.

TABLE 2

| \multicolumn{3}{l}{Names and sequences of oligonucleotide used in Example 1-1} | | |
|---|---|---|
| Tripodna | | |
| Tri-A-01 | ACGT TCGTCAACGTCTGTGCTC TCACGTTGACGCTGTCGA | (SEQ ID No. 1) |
| Tri-A-02 | ACGT TCGACAGCGTCAACGTGA AACGTGAAGCGTCTGCGA | (SEQ ID No. 2) |
| Tri-A-03 | ACGT TCGCAGACGCTTCACGTT GAGCACAGACGTTGACGA | (SEQ ID No. 3) |
| Tetrapodna | | |
| Tetra-A-01 | ACGT TCGCTGACGTTGCAGACA TCACGTTGACGCTGTCGA | (SEQ ID No. 4) |
| Tetra-A-02 | ACGT TCGACAGCGTCAACGTGA AACGTGAAGCGTCTGCGA | (SEQ ID No. 2) |
| Tetra-A-03 | ACGT TCGCAGACGCTTCACGTT GCAGACAGACGTTGACGA | (SEQ ID No. 5) |
| Tetra-A-04 | ACGT TCGTCAACGTCTGTCTGC TGTCTGCAACGTCAGCGA | (SEQ ID No. 6) |
| Tetra-B-01 | AACGTT TACGCACGACATCAGCG TCTGGACGCTTCGTCGA | (SEQ ID No. 18) |
| Tetra-B-02 | AACGTT TCGACGAAGCGTCCAGA TCTCGTCAACGCTGCGA | (SEQ ID No. 19) |
| Tetra-B-03 | AACGTT TCGCAGCGTTGACGAGA CAGACGCTGTGACGCTA | (SEQ ID No. 20) |
| Tetra-B-04 | AACGTT TAGCGTCACAGCGTCTG CGCTGATGTCGTGCGTA | (SEQ ID No. 21) |
| Tetra-C-01 | ACGTACGT TAGCACGACATCAGCG TCTGACGCTTCGTCGA | (SEQ ID No. 22) |
| Tetra-C-02 | ACGTACGT TCGACGAAGCGTCAGA TCTCGTCAACGCTGCA | (SEQ ID No. 23) |
| Tetra-C-03 | ACGTACGT TGCAGCGTTGACGAGA CAGACGCTTGACGCTA | (SEQ ID No. 24) |
| Tetra-C-04 | ACGTACGT TAGCGTCAAGCGTCTG CGCTGATGTCGTGCTA | (SEQ ID No. 25) |
| Tetra-D-01 | ACGTTAACGT TGCACGACATCAGCG TCTGACGCTCGTCGA | (SEQ ID No. 26) |

TABLE 2-continued

Names and sequences of oligonucleotide used in Example 1-1

| | | |
|---|---|---|
| Tetra-D-01 | ACGTTAACGT TCGACGAGCGTCAGA TCTCGCAACGCTGCA | (SEQ ID No. 27) |
| Tetra-D-01 | ACGTTAACGT TGCAGCGTTGCGAGA CAGACGCTTGACGCA | (SEQ ID No. 28) |
| Tetra-D-01 | ACGTTAACGT TGCGTCAAGCGTCTG CGCTGATGTCGTGCA | (SEQ ID No. 29) |
| Tetra-E-01 | ACGTCATGACGT TGCACGACATCACGT TGACGCTCGTCGA | (SEQ ID No. 30) |
| Tetra-E-01 | ACGTCATGACGT TCGACGAGCGTCAAT CTCGCAACGTGCA | (SEQ ID No. 31) |
| Tetra-E-01 | ACGTCATGACGT TGCACGTTGCGAGAC AGACGCTTGACGA | (SEQ ID No. 32) |
| Tetra-E-01 | ACGTCATGACGT TCGTCAAGCGTCTGC GTGATGTCGTGCA | (SEQ ID No. 33) |
| Tetra-F-01 | AGCT AGGCACCGTAGTCAATCG CCGATGTGTCCAAAGCCT | (SEQ ID No. 14) |
| Tetra-F-02 | AGCT AGGCTTTGGACACATCGG TGCTCCTACCGTACTCCT | (SEQ ID No. 15) |
| Tetra-F-03 | AGCT AGGAGTACGGTAGGAGCA GTTTCGGCATGTCCACCT | (SEQ ID No. 16) |
| Tetra-F-04 | AGCT AGGTGGACATGCCGAAAC CGATTGACTACGGTGCCT | (SEQ ID No. 17) |
| Pentapodna | | |
| Penta-A-01 | ACGT TCGCTGACGTTGCAGACA TCACGTTGACGCTGTCGA | (SEQ ID No. 4) |
| Penta-A-02 | ACGT TCGACAGCGTCAACGTGA AACGTGAAGCGTCTGCGA | (SEQ ID No. 2) |
| Penta-A-03 | ACGT TCGCAGACGCTTCACGTT GAGCACAGACGTTGACGA | (SEQ ID No. 3) |
| Penta-A-04 | ACGT TCGTCAACGTCTGTGCTC GCAGCGTCTTAACGTCGA | (SEQ ID No. 7) |
| Penta-A-05 | ACGT TCGACGTTAAGACGCTGC TGTCTGCAACGTCAGCGA | (SEQ ID No. 8) |
| Hexapodna | | |
| Hexa-A-01 | ACGT TCGCTGACGTTGCAGACA TCACGTTGACGCTGTCGA | (SEQ ID No. 4) |
| Hexa-A-02 | ACGT TCGACAGCGTCAACGTGA AACGTGAAGCGTCTGCGA | (SEQ ID No. 2) |
| Hexa-A-03 | ACGT TCGCAGACGCTTCACGTT GAGCACAGACGTTGACGA | (SEQ ID No. 3) |
| Hexa-A-04 | ACGT TCGTCAACGTCTGTGCTC GCAGCGTCTTAACGTCGA | (SEQ ID No. 7) |
| Hexa-A-05 | ACGT TCGACGTTAAGACGCTGC TGTCTGCAACGTCAGCGA | (SEQ ID No. 9) |
| Hexa-A-06 | ACGT TCGTAGTCCTGAACGTCT TGTCTGCAACGTCAGCGA | (SEQ ID No. 10) |

Figure 2:
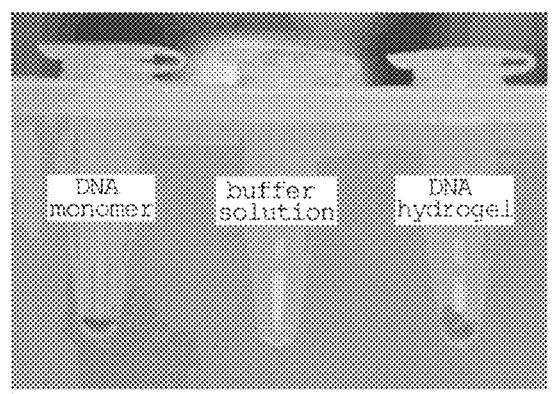
FIG. 2 A photograph showing an outline of the hydrogel formed by the present invention.
Figure 3:
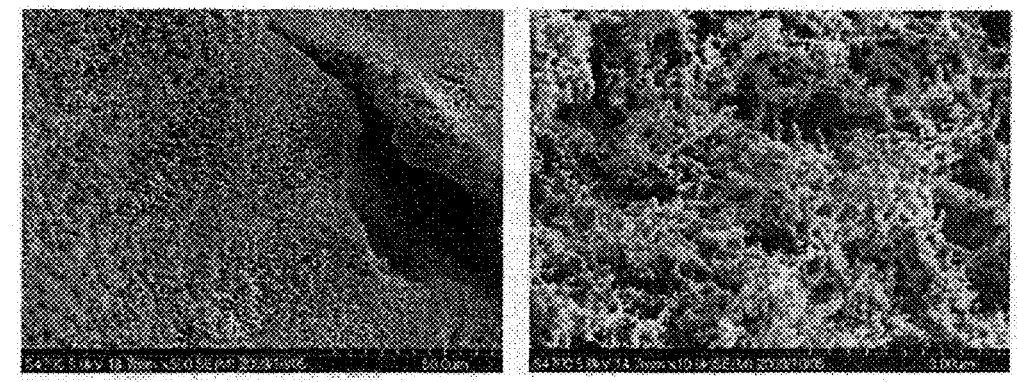
FIG. 3 Scanning electron microscope images of the hydrogel formed by the present invention.

From the above-mentioned investigation using these nucleic acid monomers, it was found that a hydrogel was able to be produced regardless of the base sequence when the cohesive protruding end had four or more bases, and the number of oligonucleotides constituting the nucleic acid unit was three or more. FIG. 1 is an estimated schematic view showing that four nucleic acid monomers (oligonucleotides) from a DNA hydrogel via estimated nucleic acid unit Tetrapodna, and FIG. 2 shows an outline of the hydrogel formed in the case where tetrapodna is used. Furthermore, FIG. 3 shows an internal structure of a gel in the observation under a scanning electron microscope. In FIG. 3, the right side is an enlarged view of the left side, showing that a gel having a network structure is formed. Note here that in this Example, any of the cohesive protruding ends of the nucleic acid monomer constituting xxxpodna have a palindrome sequence, and it is estimated that one kind of nucleic acid units are attached to each other via the palindrome sequence.

(1-2) Nucleic Acid Hydrogel Utilizing Plurality of Nucleic Acid Units

Unlike (1-1) described above, gelation can be controlled by using a nucleic acid monomer including cohesive protruding ends which are not attached to themselves (that is, not palindrome sequence). For example, a hydrogel was able to be prepared by mixing tetrapodna (G) and tetrapodna (H) described below. Furthermore, a similar gel was able to be prepared by using double strand DNA (dsDNA) instead of tetrapodna (H). In the schematic view shown in FIG. 4, the upper side shows formation of a hydrogel using Tetrapodona including two kinds of cohesive protruding ends which do not have a palindrome sequence and which are complementary to each other (corresponding to the following mixture of Tetrapodona (G) and tetrapodna (H)); and the lower side shows formation of a hydrogel using Tetrapodna (A) including a cohesive protruding end which does not have a palindrome sequence, and dsDNA including a cohesive protruding end complementary to the cohesive protruding end (corresponding to the following mixture of Tetrapodona (G) and dsDNA). Table 3 shows nucleic acid monomers used.

TABLE 3

Names and sequences of oligonucleotide used in Example 1-2

Tetrapodna(G)

| | | |
|---|---|---|
| Tetra-G-01 | TCAGAGTCAGTC TGCACGACATCACG TTGACGCTCGTCGA | (SEQ ID No. 34) |
| Tetra-G-01 | TCAGAGTCAGTC TCGACCAGCGTCAA TCTCGCAACGTGCA | (SEQ ID No. 35) |
| Tetra-G-01 | TCAGAGTCAGTC TGCACGTTGCGAGA CAGACGCTTGACGA | (SEQ ID No. 36) |
| Tetra-G-01 | TCAGAGTCAGTC TCGTCAAGCGTCTG CGTGATGTCGTGCA | (SEQ ID No. 37) |

Tetrapodna(H)

| | | |
|---|---|---|
| Tetra-H-01 | GACTGACTCTGA TGCACCACATCACG TTGACGCTCGTCGA | (SEQ ID No. 38) |
| Tetra-H-01 | GACTGACTCTGA TCGACGAGCGTCAA TCTCGCAACGTGCA | (SEQ ID No. 39) |
| Tetra-H-01 | GACTGACTCTGA TGCACGTTGCGAGA CAGACGCTTGACGA | (SEQ ID No. 40) |
| Tetra-H-01 | GACTGACTCTGA TCGTCAAGCGTCTG CGTGATGTCGTGCA | (SEQ ID No. 41) | ds

| | | |
|---|---|---|
| ds-01 | GACTGACTCTGA ACGTCAGCGTTA | (SEQ ID No. 42) |
| ds-02 | GACTGACTCTGA TAACGCTGACGT | (SEQ ID No. 43) |

Example 2-1

Preparation of Hydrogel Internally Enclosing Antigen Protein and Cell

According to Example 1, since preparation of a nucleic acid hydrogel utilizing a nucleic acid monomer was possible, a hydrogel internally enclosing an antigen protein and a cell was tried to be prepared by using thereof. Specifically, Tetrapodna (4-18-18) (SEQ ID NOs.: 2, 4, 5 and 6) shown in Table 1 was prepared into an aqueous solution such that the DNA concentration was 0.5 mM and the NaCl concentration was 5 mM, and an objective encapsulated substance (doxorubicin, egg albumin, or a RAW264.7 cell) was added thereto so as to increase the NaCl concentration to 150 mM. As a result, a hydrogel internally enclosing an antigen protein and a cell was able to be prepared. FIG. 5 shows a scanning electron microscope photograph of the resulting hydrogel internally enclosing an encapsulated substance.

Example 2-2

Incorporation of Living Cell into DNA Hydrogel

An eGFP transgenic mouse (5 weeks old) expressing a enhanced green fluorescence protein (eGFP) under control with a cytomegalovirus/chicken β-actin promoter was purchased from Japan SLC Inc. (Shizuoka, Japan). The mouse was sacrificed under anesthesia with pentobarbital, and all the connective tissue was removed from femur and shank. The femur and the shank were washed with RPMI containing 10% heat-inactivated fetal calf serum with the use of a 26-gauge needle, and a bone marrow cell was isolated. The cell mixture was filtrated through a 40 μm cell filter (BD Falcon, Franklin Lakes, N.J., USA), followed by incubation in 0.1% low osmotic pressure solution of ammonium chloride at room temperature for 5 minutes so as to dissolve the mixed erythrocytes. The remaining cells were subjected to centrifugation at 450×g for 10 minutes, and cells recovered in a pellet were used as bone marrow-derived cells (BMDCs). To each well in a 96 well plate, GFP-BMDCs were added at a density of $1 \times 10^6$ cells/well.

Next, by using ODN (Hexapodna (8-16-16)-2-01 to 06 and Hexapodna (8-16-16)-3-01 to 06) in Table 1, a DNA hydrogel was prepared in a Hanks' balanced salt solution (HESS).

Then, a DNA sample was added into a GFP-BMDC-containing well at a final concentration of 350 μg/well. Two sets of hexapodna for hydrogel were mixed with each other in a well. Thus, a fluorescence image was obtained by using a fluorescence microscope Biozero (KEYENCE CORPORATION, Osaka, Japan).

FIG. 21 shows the image of an x-z section. In FIG. 21, bars and arrows show the height of a hexapodna solution (in the upper view) or a DNA hydrogel (in the lower view). As shown in FIG. 21, the cells were incorporated in the hydrogel.

Example 3

Figure 6:
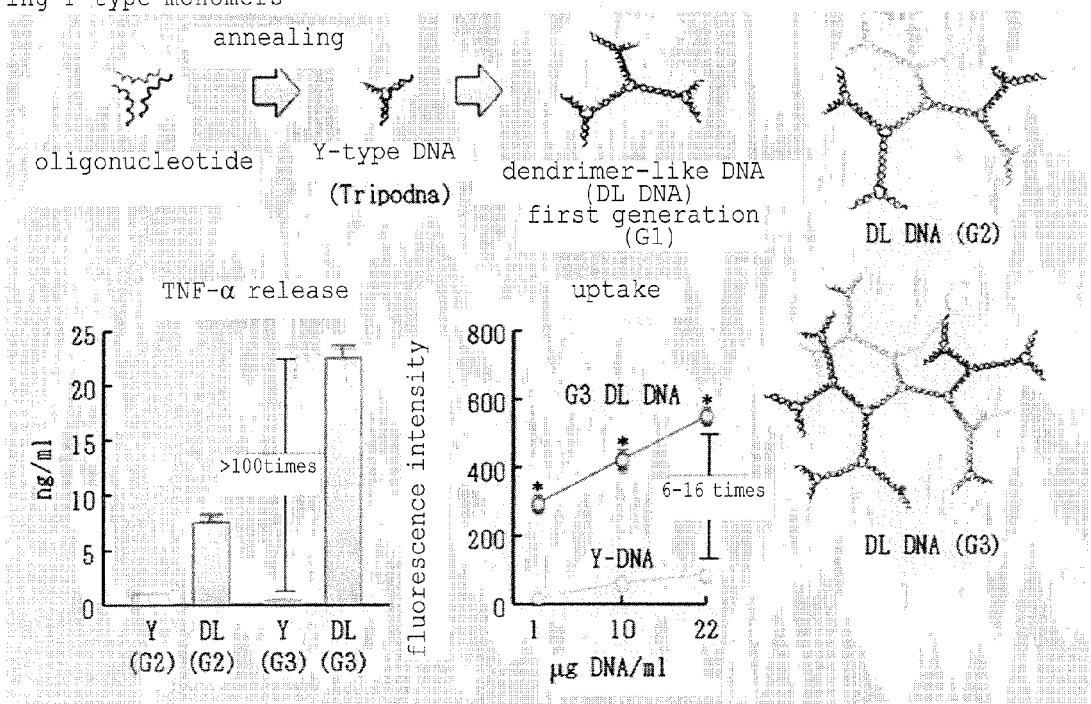
FIG. 6 Schematic views of a Y-type unit formed of oligonucleotides and a dendrimer-like DNA produced by linking the Y-type units, and graphs showing a TNF-α release activity thereof and uptake by cells.

Enhancement Ability of Activation Ability of Immunocyte in Nucleic Acid by Gelation As shown in FIG. 6, by using Tripodna (SEQ ID NOs.: 1, 2 and 3) including a CpG motif, first, Y-type DNA (Ys) as an estimated Tripodna structure was produced by annealing. Next, further four units were subjected to annealing to obtain a dendrimer-like DNA including an estimated structure G1, and further ten units were subjected to annealing to obtain a dendrimer-like DNA including an estimated structure G2. By using them, TNF-α release stimulation ability and uptake rate into a cell were examined. The results are shown in FIG. 6. It can be understood that an increase in molecular weight significantly improves both the TNF-α release activity and the cell uptake rate.

Example 4-1

Figure 7:
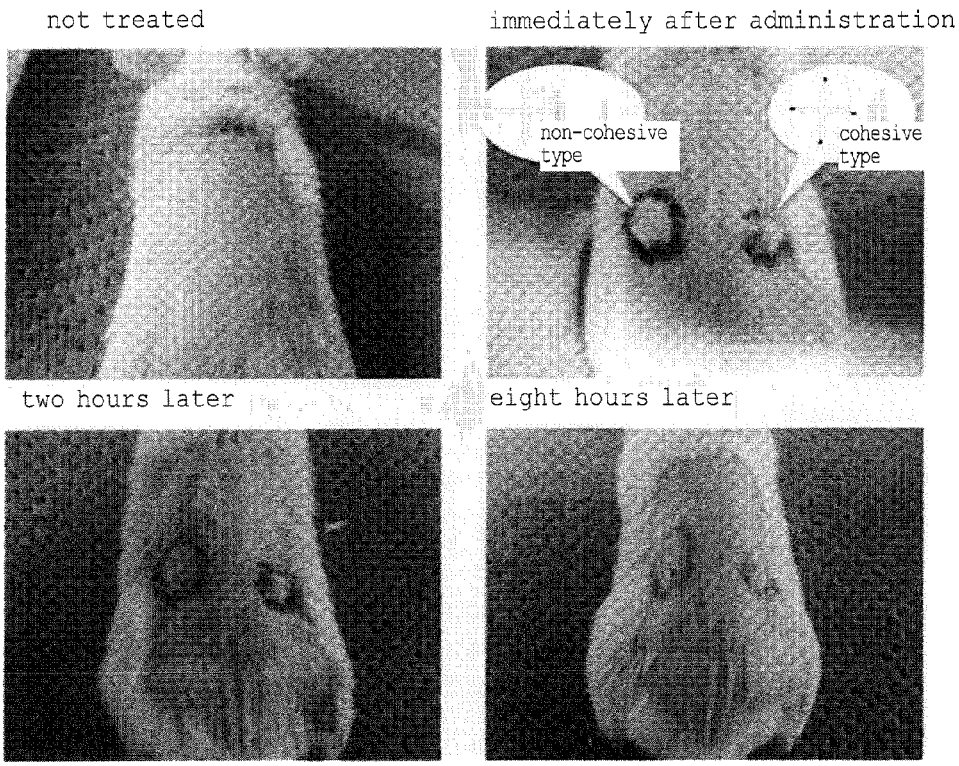
FIG. 7 Photographs showing that after the sol-like composition of the present invention is administered, a gel is formed in a living body.
Figures 1, 8:
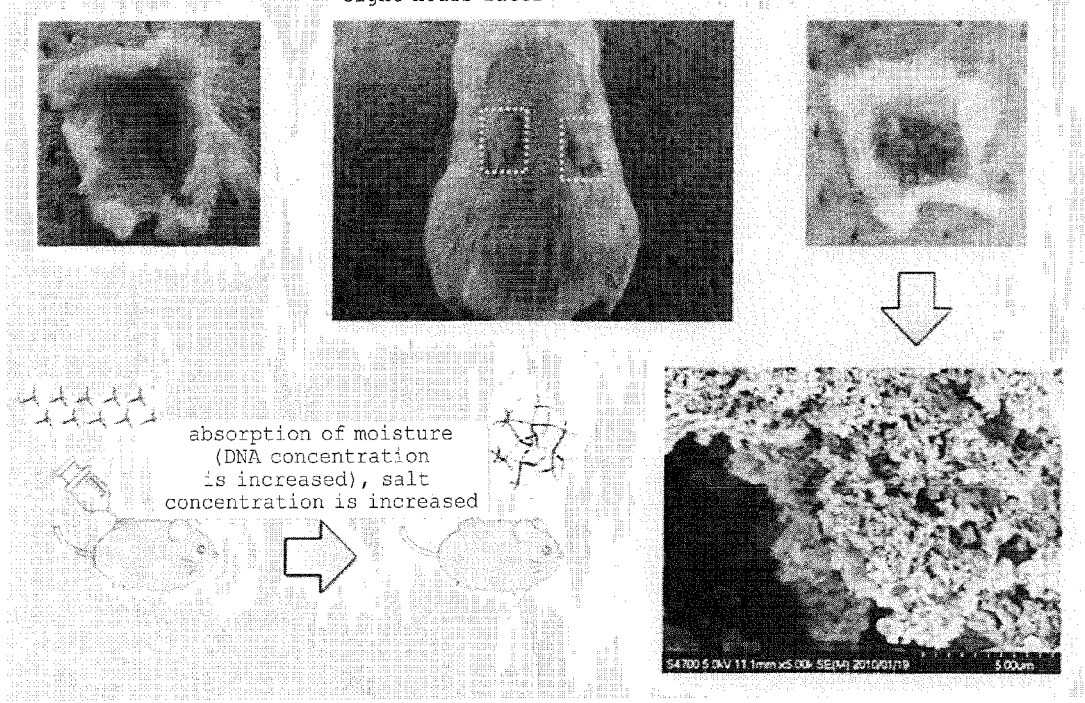
Figures 2, 8:
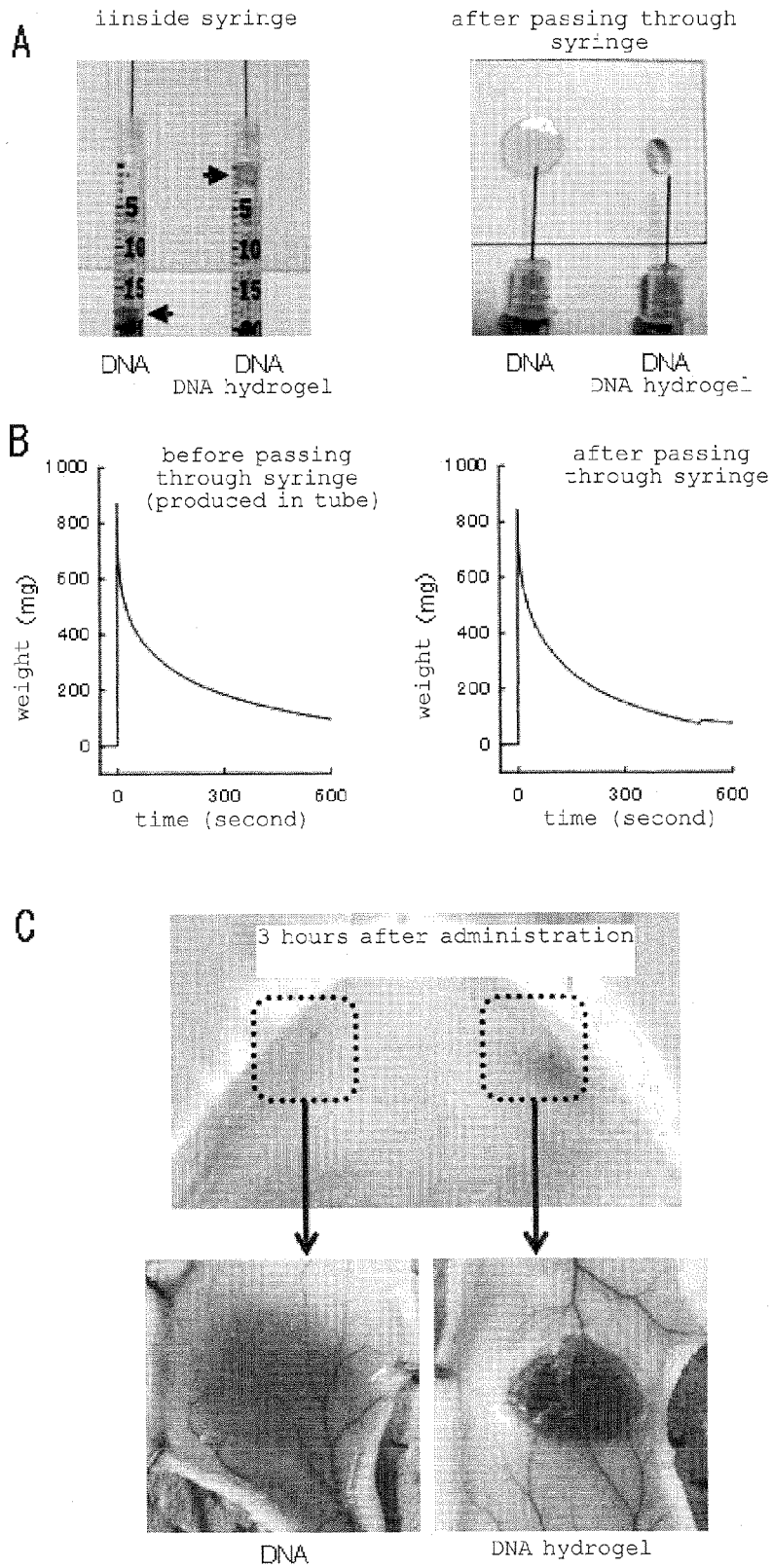

The hydrogel produced in Example 1 was able to be prepared in a sol state by appropriately adjusting conditions. Therefore, the hydrogel was able to be administered in a living body by injection. As shown in FIG. 7, a sol-state solution of control Tetrapodna having non-cohesive protruding ends at ends, and a sol-state solution of Tetrapodna (4-18-18) (SEQ ID NOs.: 2, 4, 5 and 6) in accordance with the present invention having cohesive protruding ends at ends were produced at a total DNA concentration of 2 mM and a NaCl concentration of 5 mM, and then respectively administered by injection to subcutaneous sites in the left and rights side of the back of a mouse. In the results, it was confirmed that as shown in FIG. 7 and FIG. 8-1, a gel was not formed in a living body when control Tetrapodna was used, whereas, when Tetrapodna in accordance with the present invention was used, gelation occurred in a living body after administration by an increase in the DNA concentration due to absorption of moisture from the sol-state aqueous solution with a low salt concentration and an increase in the salt concentration to the salt concentration in a living body. Thus, it was confirmed that a gel is formed in a living body only by preparing the hydrogel in accordance with the present invention in a sol state and administering the hydrogel to a living body. FIG. 8-1 also shows scanning electron microscope photograph of a gel formed in a living body.

Example 4-2

(4-2-1) State of DNA Hydrogel after Passing Through Syringe

For producing DNA (hexapodna) and a DNA hydrogel, the following ODNs in the sequence of Table 1 were used.
DNA (hexapodna): hexapodna (8-16-16)-2-01 to 06, hexapodna (8-16-16)-4-01 to 06;
DNA hydrogel: hexapodna (8-16-16)-2-01 to 06, hexapodna (8-16-16)-3-01 to 06;
Hexapodna (8-16-16)-2-01 to 06, hexapodna (8-16-16)-3-01 to 06, and hexapodna (8-16-16)-4-01 to 06 were heated to 95° C., and then gradually cooled so as to prepare hexapodna-2, hexapodna-3, and hexapodna-4, respectively, and DNA was stained with propidium iodide (PI). At this time, the ODNs were dissolved in a TE buffer (10 mM Tris-HCl, 1 mM EDTA, pH 8) containing 1.5 M NaCl, and prepared so that the final concentration of each ODN became 0.5 mM. A hexapodna-2 solution was suctioned and then hexapodna-4 (DNA) or hexapodna-3 (DNA hydrogel) is suctioned into a syringe with a 29G needle, and they were stirred in the syringe. The presence or absence of gelation was examined by visual observation, and then the DNA solution or the DNA hydrogel were extruded from the syringe.

FIG. 8-2A shows photographs showing the inside of the syringe, and states of the DNA solution and the DNA hydrogel after extrusion. As shown in FIG. 8-2A, the DNA hydrogel was in a gel state after it was extruded from the syringe.
(4-2-2) Measurement of Gel Viscoelasticity A tube including a gel was set to a gel viscoelasticity measurement device (manufactured by Nakayamadenki Co., Ltd). A gaging prong was descended to the upper end of the gel. Thereafter, a load value when the gaging prong was descended by 500 μm was measured over time. For measurement, the DNA hydrogel produced in the tube in (4-2-1) and the DNA hydrogel which was formed in the syringe and then extruded from the syringe were used.

The results of viscoelasticity are shown in FIG. 8-2B. As shown in FIG. 8-2B, the gel which had passed through the syringe had viscoelasticity which was the same level as that of the gel before passing through the syringe.
(4-2-3) Intradermal Administration to Mouse Through Syringe PI-labeled DNA (hexapodna) or a DNA hydrogel was prepared in a syringe with a 29G needle in the same manner as in (4-2-1). An ICR mouse was subjected to anesthesia with isoflurane, hair was removed from the back, and then each sample was intradermally administered by injection. Three hours after administration, the mouse was sacrificed and the skin of the back was removed, and the state of the administered site was observed.

FIG. 8-2C shows a photograph of the administered site three hours after the administration. As shown in FIG. 8-2C, the hydrogel of the present invention was in a gel state in a living body after it had passed through the syringe.

From the results of (4-2-1) to (4-2-3), it was made clear that the hydrogel of the present invention has thixotropy property, and gelation occurs in a living body again even after the hydrogel in a gel state is administered by injection through a syringe, and therefore the hydrogel can be administered by injection in a gel state through a syringe.

Example 5

Production of hydrogel using nucleic acids (including not only DNA but also RNA) having various sequences (5-1) Production of Immunologically Active Gel and Immunologically Inactive Gel As shown in FIG. 9, Tetrapodna (4-18-18) which does not contain a CpG motif (SEQ ID NOs.: 14, 15, 16 and 17) and Tetrapodna (4-18-18) which contains a CpG motif (SEQ ID NOs.: 2, 4, 5 and 6) (in FIG. 9, presence of a CpG motif is shown by underlines) were used to produce a gel as mentioned above. The produced gel was brought into contact with a mouse dendritic cell DC2.4, the gel produced by using Tetrapodna which does not contain a CpG motif did not immunologically stimulate a mouse dendritic cell as is apparent from the right photograph of FIG. 9, and the gel produced by Tetrapodna which contains a CpG motif significantly immunologically stimulated a mouse dendritic cell as is apparent from the canter photograph of FIG. 9. According to the above description, it was proved that an immunologically active gel can be produced by controlling the sequences of the nucleic acid monomer of the present invention, specifically, by allowing a CpG motif to be contained. Furthermore, similarly, it was proved that when a CpG motif is not contained, an immunologically inactive gel can be produced.

(5-2) Preparation Examples of Gel Using Xxxpodna Having Various Sequences

As shown in FIG. 10, it was confirmed that gels can be prepared by using Tripodna (4-18-18) (SEQ ID NOs.: 1, 2 and 3), Tetrapodna (4-18-18) (SEQ ID NOs.: 2, 4, 5 and 6), Tetrapodna (6-17-17) (SEQ ID NOs.: 18, 19, 20 and 21), Tetrapodna (8-16-16) (SEQ ID NOs.: 22, 23, 24 and 25), Tetrapodna (10-15-15) (SEQ ID NOs.: 26, 27, 28 and 29), Tetrapodna (12-14-14) (SEQ ID NOs.: 30, 31, 32 and 33), Pentapodna (4-18-18) (SEQ ID NOs.: 2, 3, 4, 7 and 8) and Hexapodna (4-18-18) (SEQ ID NOs.: 2, 3, 4, 7, 9 and 10), which includes a cohesive protruding end having a palindrome sequence and having a length of 4 base to 12 bases at ends. The lower view of FIG. 10 shows estimated structures of Tripodna, Tetrapodna, Pentapodna and Hexapodna in the gel, respectively.

5-3

As shown in FIG. 11, an aqueous solution containing Tetrapodna (A) (12-14-14) (SEQ ID NOs.: 34, 35, 36 and 37) including a cohesive protruding end which does not have a palindrome sequence and which has a length of 12 bases at ends at a total DNA concentration of 2 mM and a NaCl concentration of 150 mM, and an aqueous solution containing Tetrapodna (B) (12-14-14) (SEQ ID NOs.: 38, 39, 40 and 41) including a cohesive protruding end which has a length of 12 bases and which is complementary to the cohesive protruding end of Tetrapodna (A) at ends at a total DNA concentration of 2 mM and a NaCl concentration of 150 mM were prepared. These Tetrapodna (A) and Tetrapodna (B) cannot singly form a gel even if the DNA concentration and the salt concentration are increased, but a gel was formed when respective aqueous solutions were mixed with each other so that the final DNA concentration was 2 mM and the NaCl concentration was 150 mM. As shown in the lower right view in FIG. 11, Tetrapodna (A) and Tetrapodna (B) did not form a gel singly, but was able to form a gel when Tetrapodna (A) and Tetrapodna (B) were simply mixed with each other.

5-4

As shown in FIG. 12, an aqueous solution containing Tetrapodna (A) (12-14-14) (SEQ ID NOs.: 34, 35, 36 and 37) including a cohesive protruding end which does not have a palindrome sequence and which has a length of 12 bases at ends at a total DNA concentration of 2 mM and a NaCl concentration of 150 mM, and an aqueous solution containing dsDNA (12-14) (SEQ ID NOs.: 42 and 43) including a cohesive protruding end which has a length of 12 bases and which is complementary to the cohesive protruding end of Tetrapodna (A) at ends at a total DNA concentration of 1 mM and a NaCl concentration of 150 mM were prepared. These Tetrapodna (A) and dsDNA cannot singly form a gel even if the DNA concentration and the salt concentration are increased, but a gel was formed when respective aqueous solutions were simply mixed with each other so that the final DNA concentration was 2 mM and the NaCl concentration was 150 mM. As shown in the lower right view in FIG. 12, Tetrapodna (A) and dsDNA did not form a gel singly, but was able to form a gel when Tetrapodna (A) and dsDNA were simply mixed with each other.

5-5

Figure 13:
FIG. 13 Designed views of Tetrapodna including decoy DNA and siRNA. The NF-κB Decoy includes SEQ ID NOs: 169-172 beginning in the upper left quadrant and progressing clockwise to the lower left quadrant, respectively. The siRNA HIF-1α includes SEQ ID NOs:174, 170, 171, and 173 begin- FIG. 14 A protocol and a graph showing enhancement of immune response to stimulation with OVA by immunologically active Tetrapodna.

As shown in FIG. 13, by containing decoy DNA or siRNA in xxxpodna of the present invention, for example, tetrapodna, it is also possible to produce a hydrogel composed of nucleic acid having a function as a nucleic acid medicament inside the gel or the end site. In this way, by utilizing various nucleic acid sequences such as DNA and RNA, the function of the gel of the present invention can be modified.

Example 6

Figure 14:
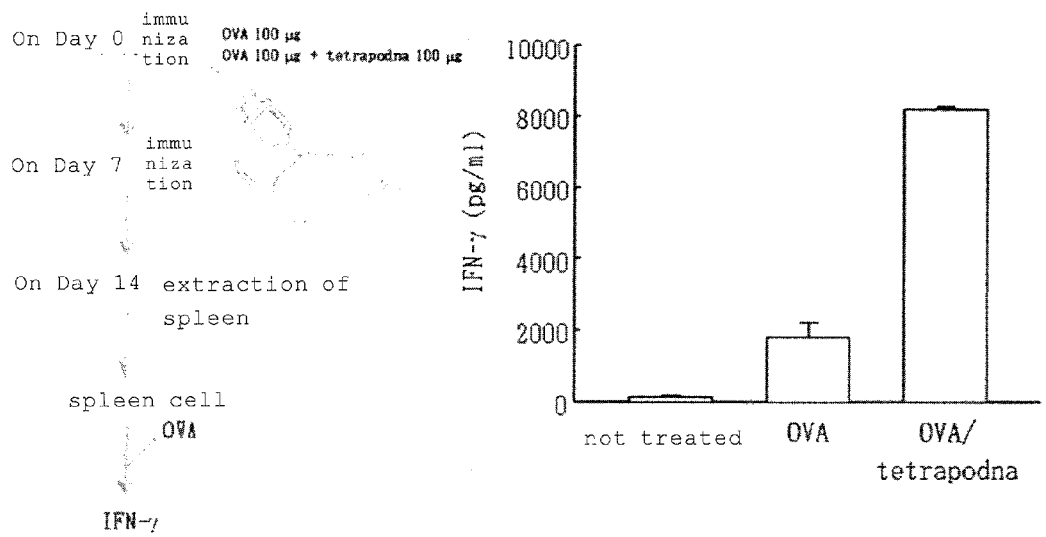

Enhancement of Immune Response Using Gel Internally Enclosing Egg Albumin (OVA) in Immunologically Active Gel As shown in FIG. 14, a sol-state aqueous solution containing 100 µg of OVA (OVA concentration of 2.5 µg/µl and NaCl concentration of 5 mM) as a control, or a sol-state aqueous solution DNA containing 100 µg of OVA and 100 µg of Tetrapodna (4-18-18) (SEQ ID NOs.: 2, 4, 5 and 6) of the present invention (OVA concentration of 2.5 µg/µl, NaCl concentration of 5 mM, and total DNA concentration of 2 mM) were injected into a mouse, respectively (0d immunization), the spleen was extracted on Day 14 of the immunization, and the obtained splenocytes were stimulated with OVA to measure the production of IFN-γ. As shown in the right side of FIG. 14, the splenocytes from the mouse to which Tetrapodna of the present invention was administered together with OVA had a remarkable increase in production amount of IFN-γ as compared with the splenocytes from the control mouse to which only OVA was administered. This demonstrated an effect of enhancing the immune response of a gel formed from Tetrapodna of the present invention.

Example 7

Adjustment of Internal Structure of Gel

FIG. 15 shows an estimated steric structure of the inside of a gel obtained from a nucleic acid monomer capable of forming Tripodna, Tetrapodna, Pentapodna and Hexapodna of the nucleic acid unit of the present invention. As is understood from FIG. 15, as the number of the nucleic acid monomers constituting the nucleic acid unit is large, that is, in Hexapodna rather than Tripodna, the internal structure of the gel is estimated to be more complicated. Furthermore, the structure of the gel can be adjusted by the length of the cohesive protruding end.

FIG. 16 shows scanning electron microscope photographs of the internal structure of a gel including Tripodna (4-18-18) (SEQ ID NOs.: 1, 2 and 3) (the length of the cohesive protruding end is 4 bases) at a DNA concentration of 1.5 mM, the internal structure of a gel including Tetrapodna (4-18-18) (SEQ ID NOs.: 2, 4, 5 and 6) (the length of the cohesive protruding end is 4 bases) at a DNA concentration of 0.5 mM, the internal structure of a gel including Hexapodna (4-18-18) (SEQ ID NOs.: 2, 3, 4, 7, 9 and 10) (the length of the cohesive protruding end is 4 bases) at a DNA concentration of 0.5 mM, and the internal structure of a gel including Tetrapodna (12-14-14) (SEQ ID NOs.: 30, 31, 32 and 33) (the length of the cohesive protruding end is 12 bases) at a DNA concentration of 0.5 mM. As is understood from the photographs, a gel obtained by using Tetrapodna had a finer internal structure than that using Tripodna, and furthermore, a gel obtained by using Hexapodna had a finer internal structure than that using Tetrapodna. When the same Tetrapodna was used, a gel obtained by using a longer cohesive protruding end had a finer internal structure.

Example 8

Figure 17:
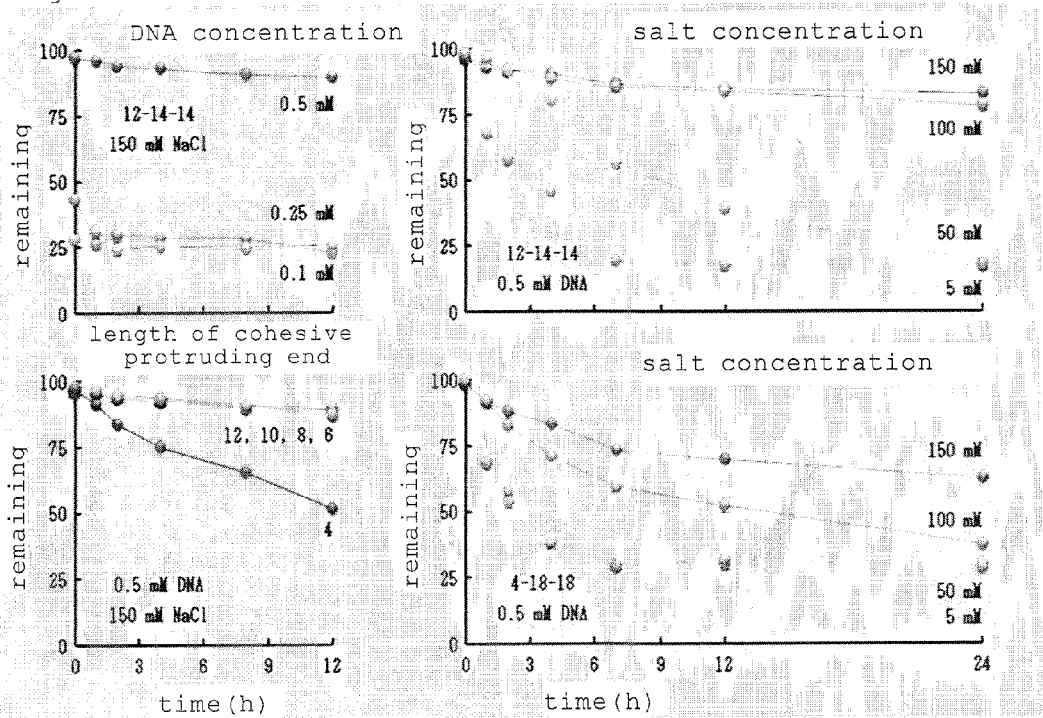
FIG. 17 Graphs showing control of gel properties by a DNA concentration, a length of a cohesive protruding end and a salt concentration.

Adjustment of Gel Strength by Adjusting Internal Structure of Gel (8-1) Adjustment of DNA Concentration Gels were formed by adjusting the NaCl concentration at 150 mM in an aqueous solution containing Tetrapodna (12-14-14) (SEQ ID NOs.: 30, 31, 32 and 33) at a DNA concentration of 0.1 mM, 0.25 mM or 0.5 mM, and the percentage of the remaining gels was measured with the passage of time. The results are shown in a graph in the left upper side of FIG. 17. The lateral axis shows the passage of time. In DNA with a low concentration (0.1 mM), gel formation was only about 25%, and by increasing the DNA concentration to 0.25 mM, the initial percentage of gels was increased, but the percentage of the remaining gels was decreased with the passage of time. On the other hand, in DNA with a high concentration (0.5 mM), the initial percentage of gels was about 100%, and the percentage of gels was decreased with the passage of time only slightly. Accordingly, it was proved that when the salt concentration is constant, as the DNA concentration is higher, it tends to be present not in a sol but in a gel.

(8-2) Adjustment of Length of Cohesive Protruding End

Gels were formed in conditions at a certain DNA concentration (0.5 mM) and a certain NaCl concentration (150 mM), and the percentage of the remaining gels was measured with the passage of time by using Tetrapodna (respectively, SEQ ID NOs.: 2, 4, 5 and 6, SEQ ID NOs.: 18, 19, 20 and 21, SEQ ID NOs.: 22, 23, 24 and 25, SEQ ID NOs.: 26, 27, 28 and 29, as well as SEQ ID NOs.: 30, 31, 32 and 33) having various lengths of the cohesive protruding end (4, 6, 8, 10 or 12 bases). The results are shown in a graph in the left lower side of FIG. 17. The lateral axis shows the passage of time. When the length of the cohesive protruding end is short (4 bases), a gel became a sol with the passage of time. When 12 hours had passed, the percentage of the remaining gels became about 50%. On the other hand, when the length of the cohesive protruding end was long (6, 8, 10 or 12 bases), the initial percentage of gels was about 100%, and the percentage of the remaining gels was decreased with the passage of time only slightly. Accordingly, it was proved that when the DNA concentration and the salt concentration are constant, as the length of the cohesive protruding end is longer, it tends to be present not in a sol but in a gel.

(8-3) Adjustment of Salt Concentration-1

Gels were formed by variously changing the NaCl concentrations (5 mM, 50 mM, 100 mM or 150 mM) of an aqueous solution containing Tetrapodna (12-14-14) (SEQ ID NOs.: 30, 31, 32 and 33) at a DNA concentration of 0.5 mM, and the percentage of the remaining gels was measured with the passage of time. The results are shown in a graph in the right upper side of FIG. 17. The lateral axis shows the passage of time. At a low salt concentration (5 mM), almost all the formed gels became in a sol state when about 6 hours had passed. When the salt concentration was increased to 50 mM, solation tendency was weakened, a change from a gel into a sol occurred moderately (about 40% when 12 hours had passed). On the other hand, at a high salt concentration (100 mM or 150 mM), the initial percentage of gels was about 100%, and the percentage of the remaining gels was decreased with the passage of time only slightly. Accordingly, it was proved that when the DNA concentration is constant, as the salt concentration is higher, it tends to be present not in a sol but in a gel.

(8-4) Adjustment of Salt Concentration-2

The percentage of the remaining gels was measured with the passage of time in the same manner as in (8-3) except that Tetrapodna (4-18-18) (SEQ ID NOs.: 2, 4, 5 and 6) was used instead of Tetrapodna (12-14-14) (SEQ ID NOs.: 30, 31, 32 and 33). The results are shown in a graph in the right lower side of FIG. 17. The lateral axis shows the passage of time. Similar to (8-3), it was proved that when the DNA concentration is constant, as the salt concentration is higher, it tends to be present not in a sol but in a gel. In (8-3), Tetrapodna (12-14-14) (the length of the cohesive protruding end is 12 bases) was used. In (8-4), Tetrapodna (4-18-18) (the length of the cohesive protruding end is 4 bases) was used. When (8-3) was compared with (8-4), it was proved that when the DNA concentration and the salt concentration are the same as each other, as the length of the cohesive protruding end is longer, it tends to be present not in a sol but in a gel.

Accordingly, it was proved that when the other conditions are constant, as the DNA concentration is higher, the salt concentration is higher, and the length of the cohesive protruding end is longer, it tends to be present not in a sol but in a gel. That is, it was proved that the internal structure of a gel, the degree of gelation, and the gel strength can be controlled by appropriately adjusting the DNA concentration, the salt concentration, and the length of the cohesive protruding end.

Example 9

Control of Releasing Rate of Encapsulated Compound in Gel by Control of Internal Structure of Gel, Degree of Gelation and Gel Strength By controlling the nature and salt concentration of protruding ends of Tetrapodna, the change of the releasing rate of an encapsulated compound in a gel was examined. Specifically, Tetrapodna (4-18-18) (SEQ ID NOs.: 2, 4, 5 and 6) including a cohesive protruding end and Tetrapodna (4-18-18) (SEQ ID NOs.: 58, 59, 60 and 61) as a control including a non-cohesive protruding end were used. In an aqueous solution of Tetrapodna which had been prepared such that the DNA concentration was 0.5 mM, the NaCl concentration was adjusted to 5 mM or 150 mM. When the NaCl concentration was increased, egg albumin (OVA, concentration of 2.5 µg/µl) was added as an encapsulated substance to cause gelation, and then the percentage of OVA released from the gel with the passage of time was measured.

Figure 18:
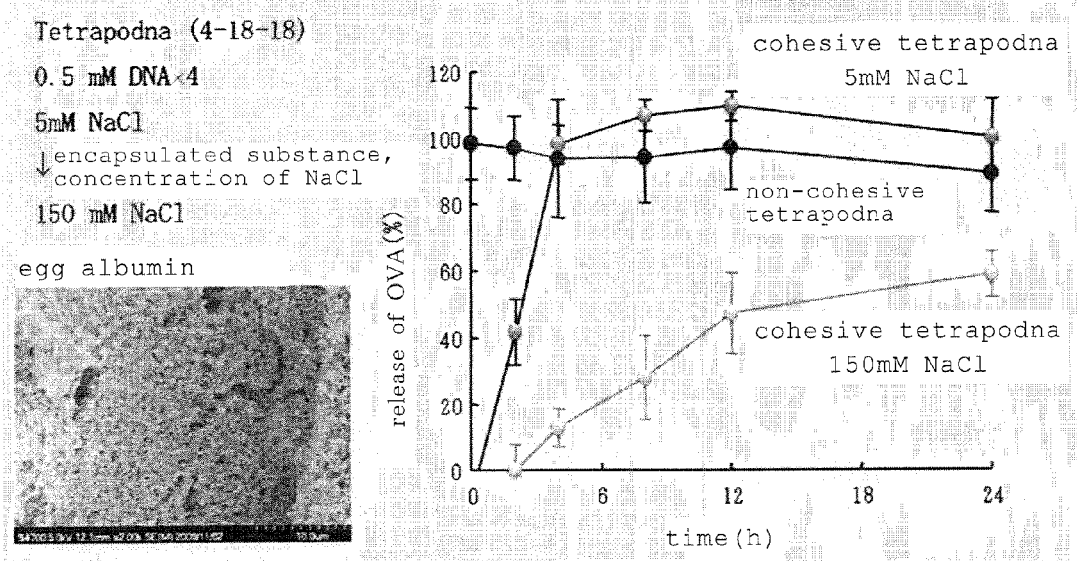
FIG. 18 A graph showing nature of a protruding end of Tetrapodna and control of the release property of an encapsulated substance from a gel by salt concentration.

The results are shown in a graph of FIG. 18. Gelation hardly found in Tetrapodna as a control including a non-cohesive protruding end, and almost 100% of OVA was released from the first. On the other hand, OVA was rapidly released from the gel produced by using Tetrapodna including a cohesive protruding end at a NaCl concentration of 5 mM, and all OVA was released for a short time. In contrast, OVA was gently released from the gel produced by using Tetrapodna including a cohesive protruding end at a NaCl concentration of 150 mM, and about 60% of OVA was released for 24 hours.

Accordingly, it was proved that the internal structure of a gel, the degree of gelation, and the gel strength can be controlled by appropriately controlling the nature and salt concentration of protruding ends, and as a result, the releasing rate of the encapsulated substance can be controlled. Furthermore, the encapsulated substance was gradually released at the salt concentration (150 mM) in a living body, and therefore the gel of the present invention is formed in a living body, thus enabling release control of drugs (achieving sustained release).

Example 10

Utilization of Nucleic Acid Having Modifying Group

Figure 19:
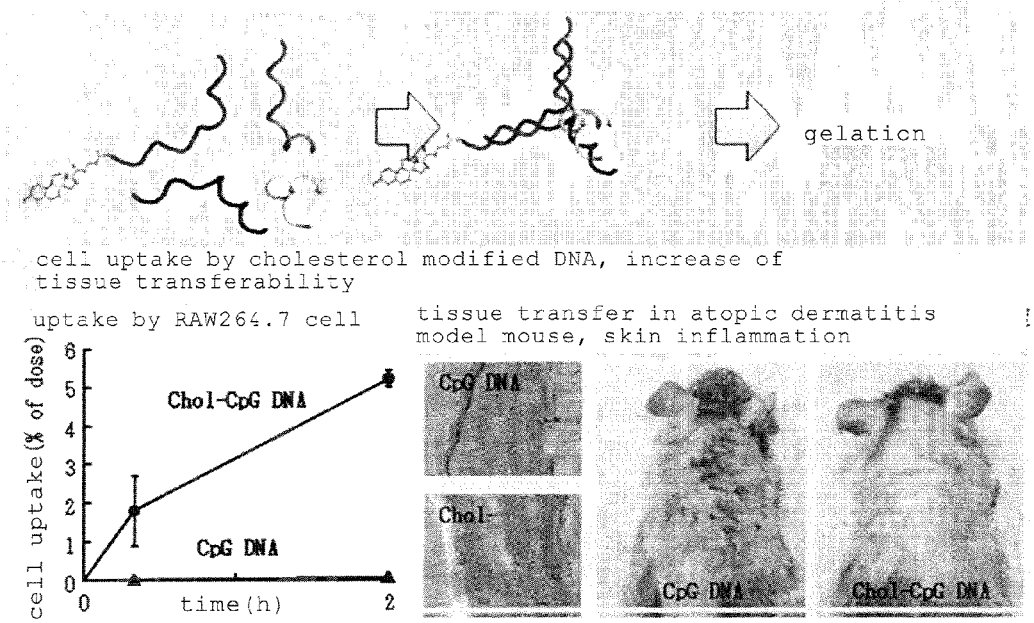
FIG. 19 Schematic views, a graph and photographs showing cell uptake of a gel by using a cholesterol-modified oligonucleotide and an increase in dermal delivery.

In order to examine applicability of nucleic acid having a modifying group, Tetrapodna using cholesterol-modified DNA was prepared. As shown in FIG. 19, a solution containing Tetrapodna (SEQ ID NOs.: 2, 4, 5 and 6: referred to as Chol-CpG DNA in FIG. 19) which contains a cholesterol-modified nucleic acid monomer and a CpG motif in nucleic acid or a solution containing similar Tetrapodna (SEQ ID NOs.: 2, 4, 5 and 6: referred to as CpG DNA in FIG. 19) which is not cholesterol-modified were respectively applied to an atopic dermatitis model mouse. Furthermore, uptake of each Tetrapodna by RAW264.7 cells was measured. As shown in the right lower side of FIG. 19, in Tetrapodna having cholesterol modification, tissue transferability was increased and skin inflammation of mouse was better suppressed as compared with Tetrapodna as a control which does not have cholesterol modification. As shown in the left lower graph in FIG. 19, Tetrapodna having cholesterol modification was incorporated into RAW264.7 cells better than Tetrapodna as a control which does not have cholesterol modification.

Accordingly, it was proved that by the use of a nucleic acid monomer having a modifying group such as cholesterol, properties of a gel can be modified or improved.

Example 11

Formation of Gel by Intranasal Administration of Sol

Figure 20:
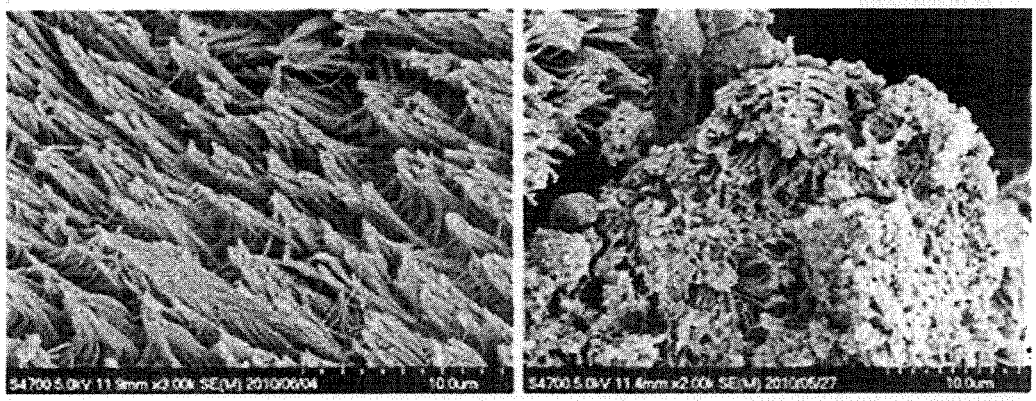
FIG. 20 Photographs showing that a gel is formed as a result of administering an ex vivo sol-like solution intranasally to a mouse.

A sol-state aqueous solution containing Tetrapodna (A) (12-14-14) (SEQ ID NOs.: 34, 35, 36 and 37) at a total DNA concentration of 2 mM and a NaCl concentration of 150 mM and a sol-state aqueous solution containing Tetrapodna (B) (12-14-14) (SEQ ID NOs.: 38, 39, 40 and 41) at a total DNA concentration of 2 mM and a NaCl concentration of 150 mM were intranasally administered to a mouse simultaneously. The results are shown in FIG. 20. It was proved that when they are intranasally administered, the salt concentration is increased, and gelation of the sol-state aqueous solution occurs, so that gels are favorably attached to the intranasal cavities.

Example 12

Investigation of Salt Concentration and Nucleic Acid Concentration for Forming Gel As mentioned above, whether or not a gel is formed, it was made clear that the DNA concentration, the salt concentration and the length of the cohesive protruding end (hereinafter, referred to as X as the number of bases) are important factors. Then, the gel formation conditions were evaluated in more detail.

Specifically, by changing the DNA concentrations of an aqueous solution of Tripodona (4-18-18) (X=4) (SEQ ID NOs.: 1, 2 and 3), Tetrapodna (4-18-18) (X=4) (SEQ ID NOs.: 2, 4, 5 and 6), Hexapodna (4-18-18) (X=4) (SEQ ID NOs.: 2, 3, 4, 7, 9 and 10) and Tetrapodna (8-16-16) (X=8) (SEQ ID NOs.: 22, 23, 24 and 25) as shown in the lines of Table 4, and by changing the NaCl concentration as shown in the rows of Table 4, whether or not a gel is formed at various DNA concentrations and NaCl concentrations was evaluated. The results are shown in Tables 4-1 to 4-4. The results are shown such that the mark "○" is given to cases in which gelation was observed, and the mark "x" is given to cases of a solution state (sol-state).

Table 4: Evaluation of gelation in various DNA concentration and NaCl concentrations

TABLE 4-1

| Tripodna(4-18-18) X = 4 | | | | | | | | | | | |
|---|---|---|---|---|---|---|---|---|---|---|---|
| Na$^+$ concentration | DNA concentration (mM) | | | | | | | | | | |
| (mM) | 1.4 | 1.2 | 1.0 | 0.9 | 0.8 | 0.7 | 0.6 | 0.5 | 0.4 | 0.3 |
| 150 | | | | | | | | | X | |
| 100 | | | | | ○ | ○ | ○ | | | |
| 50 | | | | | | ○ | X | X | X | |
| 20 | | | | | | X | | | | |

TABLE 4-1-continued

| Tripodna(4-18-18) X = 4 | | | | | | | | | | | |
|---|---|---|---|---|---|---|---|---|---|---|---|
| Na$^+$ concentration | DNA concentration (mM) | | | | | | | | | | |
| (mM) | 1.4 | 1.2 | 1.0 | 0.9 | 0.8 | 0.7 | 0.6 | 0.5 | 0.4 | 0.3 |
| 10 | | ○ | | | | | | | | |
| 2 | ○ | X | | | | | | | | |

TABLE 4-2

| Tetrapodna(4-18-18) X = 4 | | | | | | | | | | | |
|---|---|---|---|---|---|---|---|---|---|---|---|
| Na$^+$ concentration | DNA concentration (mM) | | | | | | | | | | |
| (mM) | 1.4 | 1.2 | 1.0 | 0.9 | 0.8 | 0.7 | 0.6 | 0.5 | 0.4 | 0.3 |
| 150 | | | | | | | | ○ | X | |
| 100 | | | | | | | | X | | |
| 50 | | | | | | ○ | ○ | | | |
| 20 | | | | | | X | X | | | |
| 10 | | | | | | | | | | |
| 2 | | | | | ○ | | | | | |

TABLE 4-3

| Hexapodna(4-18-18) X = 4 | | | | | | | | | | | |
|---|---|---|---|---|---|---|---|---|---|---|---|
| Na$^+$ concentration | DNA concentration (mM) | | | | | | | | | | |
| (mM) | 1.4 | 1.2 | 1.0 | 0.9 | 0.8 | 0.7 | 0.6 | 0.5 | 0.4 | 0.3 |
| 150 | | | | | | | | | ○ | X |
| 100 | | | | | | ○ | ○ | X | | |
| 50 | | | | | ○ | X | X | | | |
| 20 | | | | X | | | | | | |
| 10 | | | | | | | | | | |
| 2 | | | | | ○ | | | | | |

TABLE 4-4

| Tetrapodna(8-16-16) X = 8 | | | | | | | | | | | |
|---|---|---|---|---|---|---|---|---|---|---|---|
| Na$^+$ concentration | DNA concentration (mM) | | | | | | | | | | |
| (mM) | 1.4 | 1.2 | 1.0 | 0.9 | 0.8 | 0.7 | 0.6 | 0.5 | 0.4 | 0.3 |
| 150 | | | | | | | | | | |
| 100 | | | | | | | | | | |
| 50 | | | | | | | | | | |
| 20 | | | | | | | | ○ | | |
| 10 | | | | | | | | X | | |
| 2 | | | | | | | ○ | | | |

As is understood from Tables 4-1 to 4-4, gelation hardly tended to occur in the case of Tripodna as compared with Tetrapodna and Hexapodna, and when the number of bases of the cohesive protruding ends X was large, gelation was more likely to occur. From the results shown in Tables 4-1 to 4-4, the tendency is summarized in formulae, and the following formulae are obtained:

(1) Conditions for being maintained as sol: as a function of X, NaCl concentration=80 mM/x or less, and DNA concentration=0.3 mM+1.6/x mM or less (2) Conditions for being maintained as gel: as a function of X, NaCl concentration=640 mM/x−60 mM or more, and DNA concentration=3.2/x mM or more.

That is, it is thought that the DNA concentration and NaCl concentration of the sol-state solution that satisfies the conditions (1) are increased respectively so as to satisfy the conditions (2), and thus gelation occurs.

Example 13

Investigation of Temperature Conditions for Gel Formation

Furthermore, we investigated a possibility that temperature conditions are also involved in gelation. Tetrapodna (4-18-18) (SEQ ID NOs.: 2, 4, 5 and 6), Hexapodna (4-18-18) (SEQ ID NOs.: 2, 3, 4, 7, 9 and 10) and Tetrapodna (8-16-16) (SEQ ID NOs.: 22, 23, 24 and 25) were used to examine the temperature conditions for allowing a gel be present or a sol to be present by fixing the NaCl concentration at 150 mM and changing the DNA concentration variously.

The results are shown in Table 5.

TABLE 5

| | Tetrapodna (4-18-18) | | |
|---|---|---|---|
| DNA concentration | 0.4-0.5 mM | gel at 45° C. or less | sol at 55° C. or more |
| DNA concentration | 0.6-0.8 mM | gel at 55° C. or less | sol at 65° C. or more |
| | Hexapodna(4-18-18) | | |
| DNA concentration | 0.3-0.8 mM | gel at 55° C. or less | sol at 65° C. or more |
| DNA concentration | 1.0 mM | gel at 65° C. or less | sol at 75° C. or more |
| | Tetrapodna(8-16-16) | | |
| DNA concentration | 0.5 mM | gel at 55° C. or less | sol at 75° C. or more |

From the above, it was proved that, in any cases, when temperature is increased, solation occurs, and the higher the DNA concentration is, the more easily gelation occurs, and that the longer the length of X is, the more easily gelation occurs.

Example 14

Characteristics Comparison with Respect to Gel Prepared by Using Ligase (14-1) Preparation of DNA Hydrogel without Using Ligase Tetrapodnas (8-16-16)-1-01 to 04 shown in Table 1 were dissolved in a TE buffer (10 mM Tris-HCl, 1 mM EDTA, pH 8) containing 1.5 M NaCl and ODN mixtures were prepared so that the final concentration of each ODN was 0.5 mM. Each ODN mixture was heated to 95° C., and then gradually cooled so as to obtain a DNA hydrogel.

(14-2) Preparation of DNA Hydrogel Using Ligase

P-tetrapodna (4-18-18)-1-01 to 04 shown in Table 6 below (phosphoric acid group is added to the 5' end of the sequences in Table 1) were dissolved in a TE buffer (10 mM Tris-HCl, 1 mM EDTA, pH 8) containing 50 mM NaCl and ODN mixtures were prepared so that the final concentration of each ODN was 0.75 mM. Each ODN mixture was heated to 95° C., and then gradually cooled so as to obtain P-tetrapodna. A T4 DNA ligase (200 units; Promega, Wis., USA) and a ligation buffer (300 mM Tris-HCl, 100 mM MgCl$_2$, 100 mM DTT, 10 mM ATP) were added to the product so as to be reached at 16° C. for 16 hours, and a DNA hydrogel (using ligase) was obtained.

TABLE 6

| Name | Sequence (5' → 3') |
|---|---|
| P-tetrapodna(4-18-18)-1-01 | /5Phos/ACGT TCGCTGACGTTGCAGACA TCACGTTGACGCTGTCGA |
| P-tetrapodna(4-18-18)-1-02 | /5Phos/ACGT TCGACAGCGTCAACGTGA AACGTGAAGCGTCTGCGA |
| P-tetrapodna(4-18-18)-1-03 | /5Phos/ACGT TCGCAGACGCTTCACGTT GCAGACAGACGTTGACGA |
| P-tetrapodna(4-18-18)-1-04 | /5Phos/ACGT TCGTCAACGTCTGTCTGC TGTCTGCAACGTCAGCGA |

/5Phos/ denotes a phosphoric acid group at 5' end (14-3) Measurement of Gel Viscoelasticity The obtained gel or a solvent was placed in a tube, and the tube was set to a gel viscoelasticity measurement device (manufactured by Nakayamadenki Co., Ltd). A gaging prong was descended to the upper end of the gel. Thereafter, a load value (weight) when the gaging prong was descended by 500 μm was measured over time.

Figure 22:
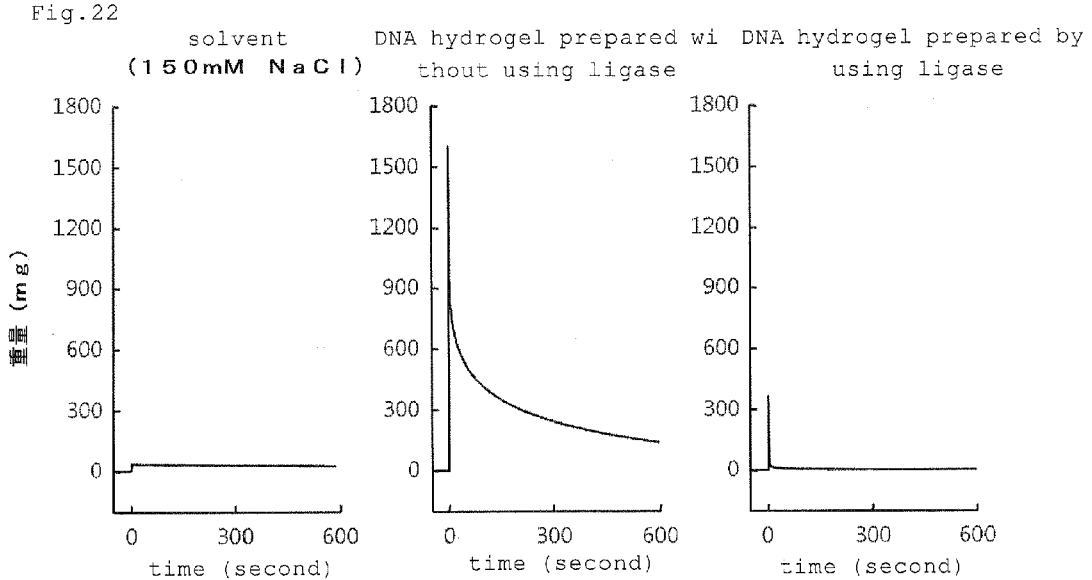
FIG. 22 Graphs showing comparison of gel viscoelasticity between a DNA hydrogel prepared by using a ligase and a DNA hydrogel prepared without using a ligase.

The results are shown in FIG. 22. A peak value in the drawing is a parameter corresponding to the hardness of the gel. In the same DNA concentration conditions, a DNA hydrogel prepared by using a self-gelatinizable nucleic acid showed a high value (about 1600 mg and about 400 mg). It was made clear that a self-gelatinizable nucleic acid which does not use a ligase is harder than a DNA hydrogel produced by using a ligase. Furthermore, the gradient of the transition curve in FIG. 22 is a parameter corresponding to the viscoelasticity of a gel. It was made clear that the DNA hydrogel prepared by using a self-gelatinizable nucleic acid shows gentler, and the DNA hydrogel shows excellent viscoelasticity. The DNA hydrogel produced by using a ligase was fragile.

Example 15

PAGE Analysis of Polypodna Preparation Using 3 to 12 Pods ssDNA, dsDNA and each poolypodna preparation were prepared in the same manner as in Example 1 by using the sequences in Table 1, and the prepared products were subjected to electrophoresis on a 6% polyacrylamide gel for 20 minutes and at 200 V, respectively.

Figure 23:
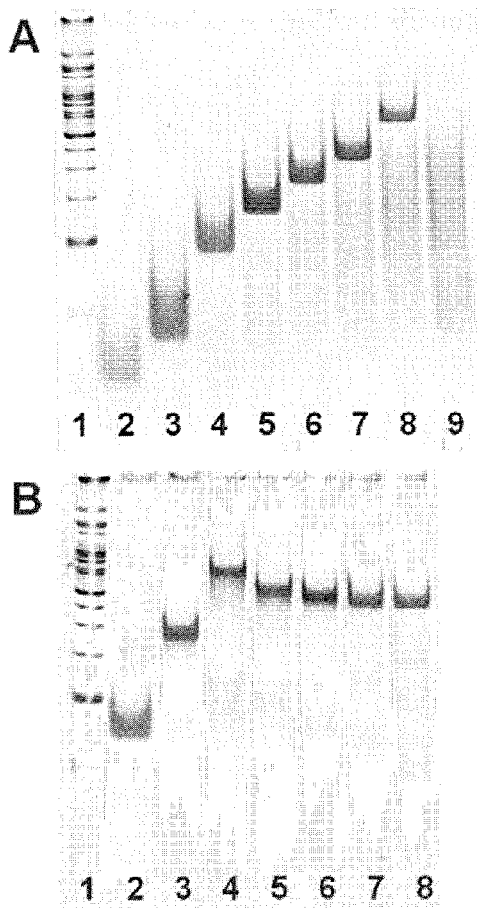
FIG. 23 Photographs showing a result of PAGE analysis of polypodna preparations including 3 to 12 pods.

The results are shown in FIG. 23. Each lane in FIGS. 23A and B, and correlation with the electrophoresis product are shown in Table 7 below.

TABLE 7

| FIG. 23A | |
|---|---|
| Lane 1 | 100 bp DNA ladder |
| Lane 2 | ssDNA$_{36}$ |
| Lane 3 | dsDNA$_{36}$ |
| Lane 4 | tripodna$_{36}$ |
| Lane 5 | tetrapodna$_{36}$ |
| Lane 6 | pentapodna$_{36}$ |
| Lane 7 | hexapodna$_{36}$ |
| Lane 8 | octapodna$_{36}$ |
| Lane 9 | dodecapodna$_{36}$ |
| FIG. 23B | |
| Lane 1 | 100 bp DNA ladder |
| Lane 2 | tripodna$_{30}$ |
| Lane 3 | tripodna$_{60}$ |
| Lane 4 | tripodna$_{90}$ |
| Lane 5 | tripodna$_{80}$ |
| Lane 6 | tetrapodna$_{60}$ |
| Lane 7 | pentapodna$_{48}$ |
| Lane 8 | hexapodna$_{40}$ |

As shown in FIG. 23A, in tripodna$_{36}$, tetrapodna$_{36}$, pentapodna$_{36}$, hexapodna$_{36}$ and octapodna$_{36}$, a major single band was observed. This showed that a polypod-like structure is formed at high efficiency. On the other hand, in dodecapodna$_{36}$, a major band was not formed. It is thought that dodecapodna has low thermal stability and a critical point is present between the pod of 8 and the pod of 12. Furthermore, when the number of pods was increased, the degree of electrophoresis was deteriorated.

The lanes 2 to 5 of FIG. 23B show PAGE analyses of tripodna having 30, 60 or 90 nucleotides. When the ODN length in the tripodna was increased, the degree of electrophoresis was increased. The degree of electrophoresis seems to be changed dependent upon the number of bases in the polypodna preparation. The degrees of electrophoresis of various polypodnas having 240 bases (FIG. 23B, lanes 6 to 8) were the same as each other. This shows that the degree of electrophoresis is dependent upon the number of nucleotides and is not dependent upon the steric structure.

Example 16

CD Spectrum (Circular Dichroism Spectrum)

dsDNA$_{36}$, A$_{36}$, (CG)$_6$, and each poolypodna preparation were prepared in the same manner as in Example 1 by using the sequences in Table 1. Each annealed DNA sample was diluted with a TE buffer containing 5 mM sodium chloride so that the final DNA concentration was 25 mg/ml. Then, a CD spectrum (circular dichroism spectrum) of DNA was recorded by using JASCO-820 type spectropolarimeter (JASCO, Tokyo, Japan) at 4° C. with the use of a quartz cell having 0.1 cm passage length at 25° C. The CD spectrum (circular dichroism spectrum) of DNA was measured in a range from 200 nm to 320 nm. For promoting comparison, in order to obtain a mol elliptic rate, background cut-off, smoothing, and concentration adjustment for the CD spectrum (circular dichroism spectrum) were carried out.

The results are shown in FIG. 24. In the case of dsDNA$_{36}$, a positive peak and a negative peak are observed around 280 nm and 240 nm. This shows a typical spectrum of B-type DNA. All the polypodnas showed the same peaks as in dsDNA$_{36}$ (FIG. 24A). The spectrum of (CG)$_6$ in FIG. 24B is a typical spectrum of Z-type DNA. Hexapodna$_{36}$ showed a peak different therefrom. Accordingly, it was made clear that each polypodna has a B-type DNA structure as a structure in normal conditions of a double strand DNA.

Example 17

Tm Value and Apparent Size

Each DNA preparation was prepared in the same manner as in Example 1 by using the sequences in Table 1. The absorbance of polypodna or other DNA preparations at 260 nm was measured by using a Shimadzu UV-1600 PC spectrometer (Kyoto, Japan) equipped with a TMSPC-8 temperature controller 18. The melting temperature (Tm) was obtained from the melting curve at the sodium concentration of 5 mM in each preparation.

Furthermore, the apparent size of each polypodna was measured by using Malvern Zetasizer 3000HS (Malvern Instruments, Malvern, UK) according to a dynamic light scattering method at 20° C. The measurement was repeated at least three times, and the results thereof were represented as an average±standard error (S.E.) of the reproducible results. The result of the size was obtained as average±S.E. of three (tripodna$_{36}$, tetrapodna$_{36}$, pentapodna$_{36}$, hexapodna$_{36}$, tripodna$_{80}$, tetrapodna$_{60}$, pentapodna$_{48}$ and hexapodna$_{40}$) or six (octapodna$_{36}$, tripodna$_{60}$ and tripodna$_{90}$).

Each result is shown in Table 8.

TABLE 8

| DNA preparation | Tm (° C.) | Size (nm) |
|---|---|---|
| dsDNA$_{36}$ | 66.5 | N.D. |
| Tripodna$_{36}$ | 54.6 | 6.16 ± 0.04 |
| Tetrapodna$_{36}$ | 50.8 | 7.39 ± 0.15 [a] |
| Pentapodna$_{36}$ | 47.9 | 7.68 ± 0.06 [a] |
| Hexapodna$_{36}$ | 44.8 | 8.16 ± 0.08 [a] |
| Octapodna$_{36}$ | 43.9 | 8.33 ± 0.42 [a] |
| Tripodna$_{30}$ | 46.5 | N.D. |
| Tripodna$_{60}$ | 61.2 | 8.87 ± 0.13 [b] |
| Tripodna$_{80}$ | 64.9 | 10.7 ± 0.2 [d,e,f] |
| Tripodna$_{90}$ | 68.3 | 12.1 ± 0.4 |
| Tetrapodna$_{60}$ | 59.8 | 9.14 ± 0.17 [c,f] |
| Pentapodna$_{48}$ | 53.2 | 8.48 ± 0.31 [c,f] |
| Hexapodna$_{40}$ | 48.5 | 6.47 ± 0.30 [c,d,e] |

[a] P < 0.05 tripodna$_{36}$ -;
[b] P < 0.05 tripodna$_{90}$ -;
[c] P < 0.05 tripodna$_{80}$ -;
[d] P < 0.05 tetrapodna$_{60}$ -;
[e] P < 0.05 pentapodna$_{48}$ -;
[f] P < 0.05 hexapodna$_{40}$ -;
N.D. not detectable As shown in Table 8, the Tm value of dsDNA$_{36}$ was higher than that of the other preparations using 36 mer ODN. The Tm value is a function of the number of pods, and it was made clear that as the number of pods was increased, the Tm value was reduced. Furthermore, it was made clear that the Tm value of the tripodna preparation is dependent upon the length of ODN, and that Tripodna$_{90}$ shows the maximum Tm value.

Furthermore, as shown in Table 8, it was made clear that when the length of ODN is increased from 30 to 90, the apparent size of the tripodna preparation is increased. The sizes of polypodnas (Tripodna$_{80}$, Tetrapodna$_{60}$, Pentapodna$_{48}$ and Hexapodna$_{40}$) having 240 bases were dependent upon the length of ODN. In the polypodna preparation including 36 mer ODN, when the number of pods was increased, the size thereof was slightly increased. This is presumed that in the preparations having a large number of pods, the stacking of bases is reduced, thus expanding the structure.

Example 18

Stability of Polypodna in Serum

Each poolypodna preparation was prepared in the same manner as in Example 1 by using the sequences in Table 1.

Each Polypodna preparation was incubated together with a 20% mouse serum which had been diluted with a RPMI1640 medium at 37° C. and at a concentration of 10 µg/100 µl. When 0, 2, 4, 8, 12 or 24 hours had passed after the incubation, 10 µl aliquot of the sample solution was transferred to a plastic tube, mixed with 20 µl of a 0.5 M EDTA solution to stop degradation, and the mixture was stored at −20° C. before use. These samples were subjected to electrophoresis by 12% PAGE at 4° C., and stained with SYBR Gold (Molecular Probes, Eugene, Oreg., SA). The density of the DNA band was quantitatively evaluated by using Multi Gauge software (Fujifilm Corporation, Tokyo, Japan).

The results are shown in FIGS. 25A to D. These experiments were carried out three times, and the same results were obtained. FIGS. 25A and C show one typical gel. As shown in FIGS. 25A and B, it was made clear that as the length of pod of the tripodna is longer, the degradation rate is higher. Furthermore, as shown in FIGS. 25C and D, it was made clear that as the number of pods is larger, the stability in the mouse serum is low. This is presumed that DNA is degraded mainly by exonuclease in a body fluid, and therefore the DNA is easily degraded when the number of pods is larger and the number of ends is larger.

Example 19

Transfer of DNA Hydrogel to Local Lymph Node

Hexapodna (8-16-16)-2-01 in Table 1 was end-labeled with $^{32}$P. That is, ODN was reacted with γ-$^{32}$P ATP at 37° C. for 30 minutes by using T4 polynucleotide kinase (T4 PNK; TAKARA BIO INC., Otsu, Japan), and heated at 80° C. for 12 minutes to denature T4 PNK. The labeled product was purified by using a NAP5 column (GE Healthcare, Tokyo, Japan). A tracer amount of $^{32}$P-hexapodna (8-16-16)-2-01 and the other ODNs shown in Table 9 below were used so as to prepare $^{32}$P-labeled samples.

TABLE 9

| $^{32}$P-ssDNA | $^{32}$P-hexapodna(8-16-16)-2-01 |
| | hexapodna(8-16-16)-2-01 |
| | hexapodna(8-16-16)-3-01 |
| $^{32}$P-Hexapodna | $^{32}$P-hexapodna(8-16-16)-2-01 |
| | hexapodna(8-16-16)-2-01 to 06 |
| | hexapodna(8-16-16)-4-01 to 06 |
| $^{32}$P-DNA hydrogel | $^{32}$P-hexapodna(8-16-16)-2-01 |
| | hexapodna(8-16-16)-2-01 to 06 |
| | hexapodna(8-16-16)-3-01 to 06 |

Each $^{32}$P-DNA sample was injected to the skin of the back of a 4-week old male ICR mouse at an administration dose of 10 mg/kg. After a predetermined interval of the infusing, the mouse was subjected to anesthesia with isoflurane, the skin of the back as well as inguinal and axillary lymph nodes were collected from the infusion site and the local lymph node, respectively. Each sample was placed in a 20 ml polypropylene scintillation vial containing 700 µl of Soluene-350 (PerkinElmer Japan Co., Ltd., Kanagawa, Japan), and incubated overnight at 60° C. for digestion. To the vial, 2-propanol (200 µl) and hydrogen peroxide (200 µl, 30% w/v; SAN-TOKU CHEMICAL INDUSTRIES CO., LTD, Tokyo, Japan) were continuously added. The sample was stood still at room temperature until foaming disappeared.

Next, 100 µl of a 5 M hydrogen chloride solution and 5 ml of Clear-sol I (NACALAI TESQUE, INC., Kyoto, Japan) were added to the sample. Radioactivity of the sample was measured by a Tri-Carb 3110TR liquid scintillation analyzer (PerkinElmer, Norwalk, Conn., USA). The results are calculated as percentage of the infusion amount of the radioactivity for each sample, and represented as average±S.D. of three mice.

Figure 26:
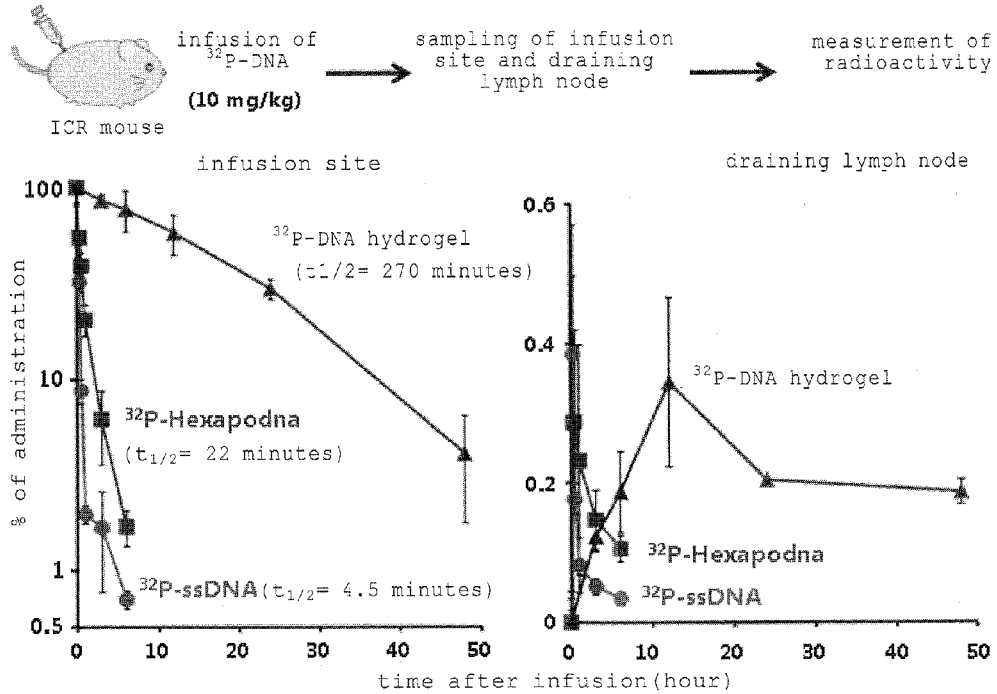
FIG. 26 Graphs showing time courses of radioactivity in an injection site and a draining lymph node after intradermal injection of a $^{32}$P-DNA hydrogel into a mouse.

The results are shown in FIG. 26. As shown in FIG. 26, it was made clear that the DNA hydrogel remains in the injection site for a longer time than hexapodna or ssDNA, and transfers to the local lymph node over a long time. This supports that the sustained release properties of the DNA hydrogel is high.

Example 20

Collapse of DNA Hydrogel, Release of DXR from DNA Hydrogel, and Tumor Proliferation in Mouse A DNA hydrogel was prepared in the same manner as in Example 1 by using ODN (hexapodna (8-16-16)-2-01 to 06 and hexapodna (8-16-16)-3-01 to 06) shown in Table 1.

In order to prepare a doxorubicin (DXR)/DNA hydrogel, DXR in aqueous Mili-Q was added to an injector, and two hexapodna preparations were added to DXR continuously. After incubation at room temperature for one hour, the mixture was used as a DXR/DNA hydrogel. The mixing ratio of DXR and DNA was fixed to 1:40 weight ratio.

To the DXR/DNA hydrogel (300 µg/10 µl), 10 µl of a physiological saline solution or a 20% mouse serum was added, and incubated at 37° C. After predetermined time had passed, the sample was collected. After centrifugation at 2000×g for 5 seconds, the supernatant was collected, and the absorbance of DNA and the fluorescence of DXR were measured at excitation and light-emitting wavelength of 485 nm and 560 nm, respectively, by using a spectrophotometer (UV-1600, SHIMADZU, Japan) and multi label counter (ARVO™ MX 1420, Wallac, Finland). Then, concentrations of DNA and DXR were estimated.

Figure 27:
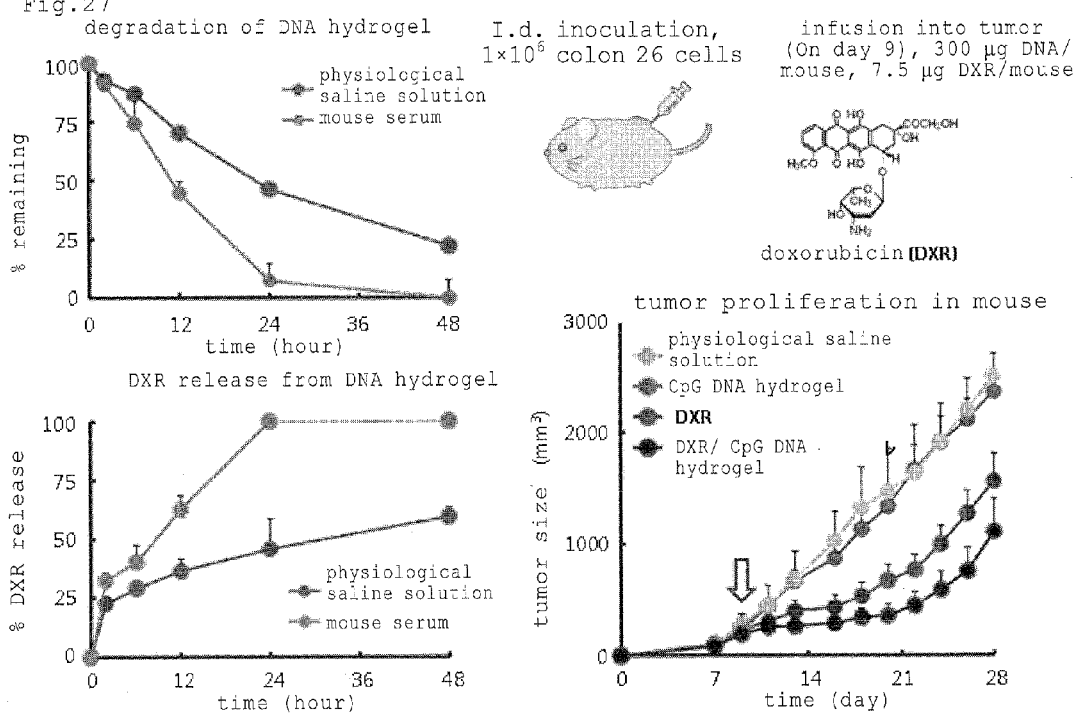
FIG. 27 A graph showing degradation over time of a DNA hydrogel in a mouse serum (left upper view); a graph showing change over time of the release of DXR from a DNA hydrogel internally enclosing DXR (left lower view); and a graph showing an effect of CpG DNA hydrogel internally enclosing DXR on suppressing tumor growth (right view).

The results are shown in the left upper view and left lower view of FIG. 27. The DNA hydrogel was degraded in the mouse serum earlier than in the physiological saline solution (the left upper in FIG. 27). Furthermore, DXR in the DNA hydrogel was released in the mouse serum in a larger amount than in the physiological saline solution (the left lower in FIG. 27).

A hydrogel was prepared in the same manner as in Example 1 by using

ODNs (hexapodna (8-16-16)-2-01 to 06 and hexapodna (8-16-16)-3-01 to 06) shown in Table 1, and a DXR/DNA hydrogel was prepared in the same manner as mentioned above. On the other hand, the skin of the back of a BALB/c mouse was inoculated with Colon26/Luc cells (5×10$^5$ cells/mouse). Nine days after the tumor inoculation, a physiological saline solution, DXR (7.5 µg/mouse), a DNA hydrogel (300 µg/mouse) or a DXR/DNA hydrogel (7.5 µg of DXR and 300 µg of DNA/mouse) were infused to the tumor of the mouse. The tumor size was measured regularly by using a caliper.

The results are show in the right view of FIG. 27. It was made clear that DXR shows high tumor growth suppressing ability when it is contained in a DNA hydrogel (the right view of FIG. 27).

Example 21

IL-6 Induction

DNA samples were prepared by using ODNs of Table 10 in the sequences shown in Table 1.

TABLE 10

| | |
|---|---|
| CpG ssDNA | hexapodna(8-16-16)-2-01 |
| | hexapodna(8-16-16)-3-01 |
| CpG hexapodna | hexapodna(8-16-16)-2-01 to 06 |
| | hexapodna(8-16-16)-4-01 to 06 |
| CpG DNA hydrogel (fragment) | hexapodna(8-16-16)-2-01 to 06 |
| | hexapodna(8-16-16)-3-01 to 06 |
| GpC ssDNA | hexapodna(8-16-16)-5-01 |
| | hexapodna(8-16-16)-6-01 |
| GpC hexapodna | hexapodna(8-16-16)-5-01 to 06 |
| | hexapodna(8-16-16)-7-01 to 06 |
| GpC DNA hydrogel (fragment) | hexapodna(8-16-16)-5-01 to 06 |
| | hexapodna(8-16-16)-6-01 to 06 |

Mouse dendritic DC2.4 cells were seeded on a 96-well culture plate at a density of $5 \times 10^4$ cells/well, and incubated overnight in 5% $CO_2$ at 37° C. DNA samples were added to the cells at the indicated concentration, and the cells were incubated for 16 hours.

Subsequently, the supernatant was collected, and stored at −80° C. until measurement. According to the manufacturer's protocol (BD Biosciences, San Diego, Calif., USA), the concentration of IL-6 was measured by Enzyme-Linked Immunosorbent Assay (ELISA).

The results are shown in FIG. 28. As shown in FIG. 28, it was made clear that CpG DNA in a hydrogel state shows higher immune stimulation properties than CpG DNA of a single strand or hexapodna.

Example 22

Release of Cytokine from RAW264.7 Cell by DNA Preparation

Each sample was prepared in the same manner as in Example 1 by using the sequences in Table 1.

In a RPMI1640 medium to which 10% heat inactivated FBS, 0.15% sodium bicarbonate, 100 units/ml penicillin, 100 mg/ml streptomycin and 2 mML-glutamine were added, murine macrophage-like RAW264.7 cells were proliferated in humidified air containing 5% $CO_2$ at 37° C. Subsequently, cells were seeded on a 24-well or 96-well culture plate at a density of $5 \times 10^5$ cells/well, and cultured for 24 hours before use.

The RAW264.7 cells were seeded on a 24-well plate at a density of $2.5 \times 10^5$ cells/well, and incubated for 24 hours before treatment. Then, ssDNA, dsDNA, or several kinds of polypodnas diluted in 0.5 ml of Opti-MEM were added to the cells at a final concentration of 0.5, 1 or 2 µg/ml. The cells were incubated for 8 hours, the supernatant was recovered and stored at −70° C. before use. The concentrations of TNF-α and IL-6 in the supernatant were measured by Enzyme-Linked Immunosorbent Assay (ELISA) using an OptEIA™ set (Pharmingen, San Diego, Calif., USA).

Figure 29:
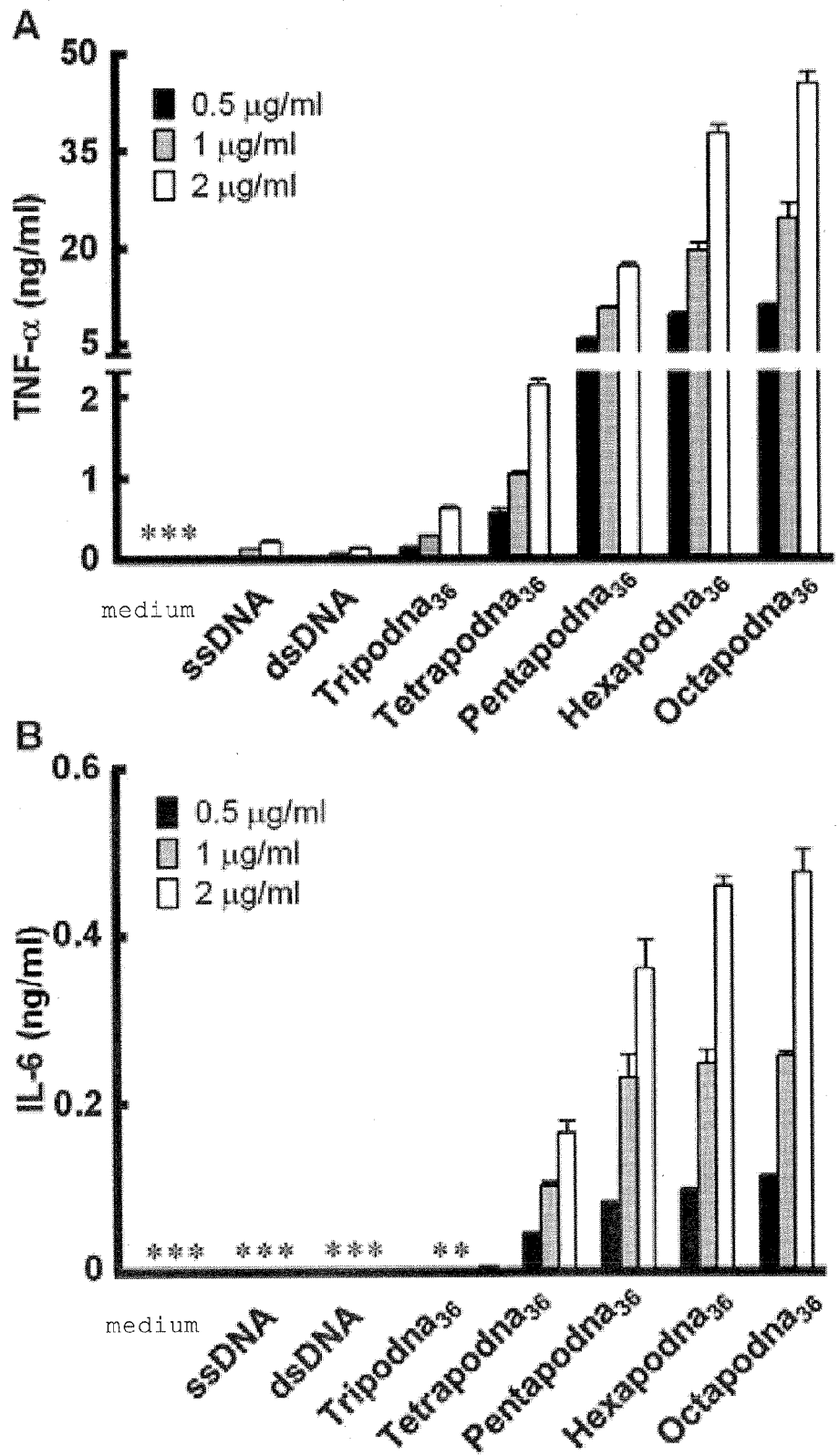
FIG. 29 Graphs showing induction of release of TNF-α (A) and IL-6 (B) by polypodna preparations containing CpG.

The results are represented as average±S.D of three measurements and shown in FIG. 29. Data is a representative of four (TNF-α) or two (IL-6) independent experiments. The mark "*" in the drawing indicates that the value is below the detection limit. In the case of ssDNA and dsDNA, the TNF-α release hardly occurred. On the contrary, polypodna preparations induced the release of cytokine from the RAW264.7 cells in a manner dependent upon the DNA concentration (FIG. 29A). Furthermore, it was also made clear that when the number of pods is larger, the amount of TNF-α released is increased. The same results are also shown in FIG. 29B which shows the results about IL-6 release. Accordingly, it was made clear that the polypodna preparation has higher immune stimulation activity of CpGDNA as the number of pods is larger.

Example 23

Release of TNF-α from RAW264.7 Cell by Polypodna Preparation

The same experiment as in Example 22 was carried out except that each poolypodna preparation was prepared in the same manner as in Example 1 by using the sequences in Table 1. However, the added DNA was equal amount in each case.

Figure 30:
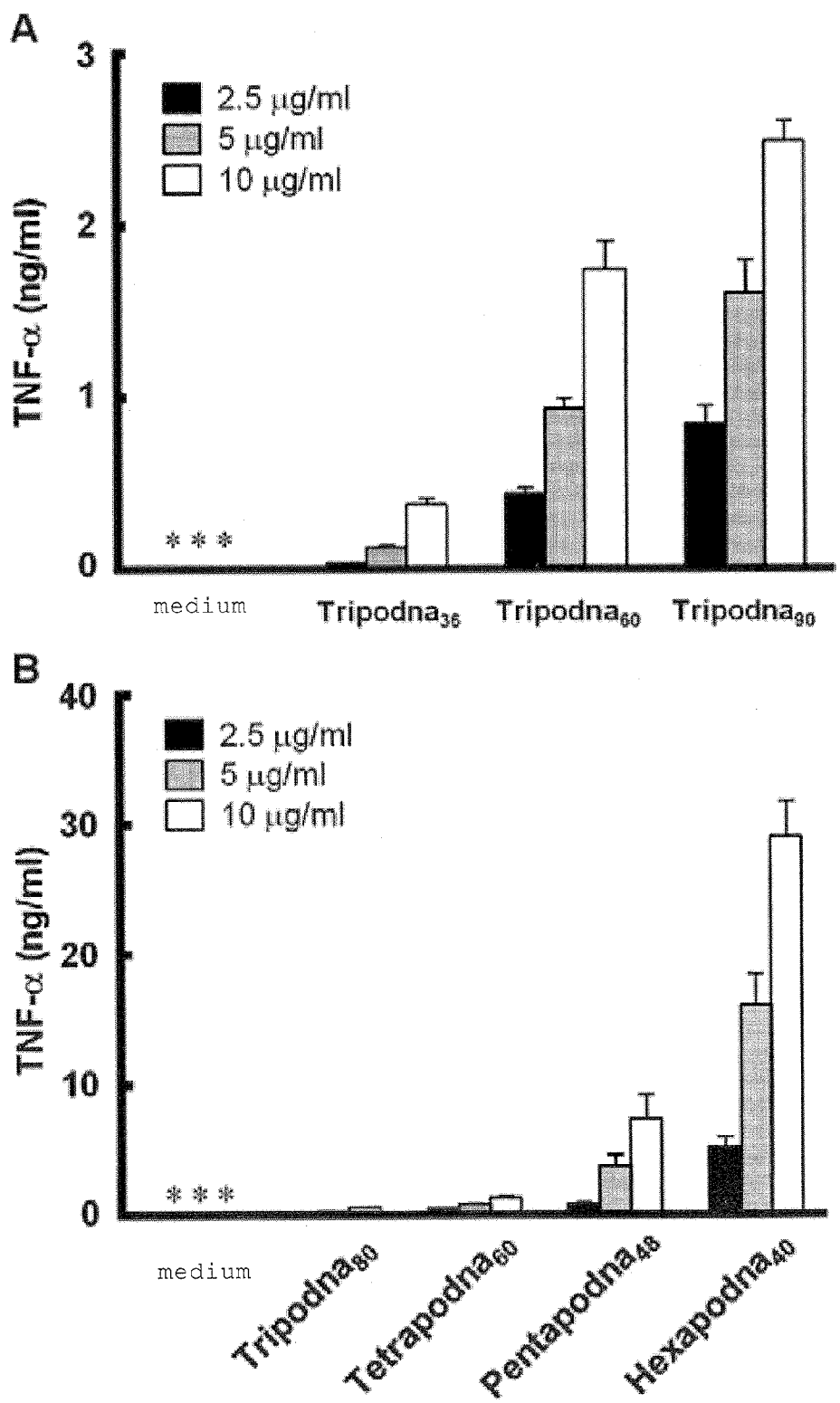
FIG. 30 Graphs showing induction of release of TNF-α by polypodna preparations containing CpG.

The results are represented as average±S.D of three measurements and shown in FIG. 30. Data is a representative of four (FIG. 30A) or three (FIG. 30B) independent experiments. The mark "*" in the drawing indicates that the value is below the detection limit. As shown in FIG. 30A, in the tripodna, the number of nucleotides is increased, the release of TNF-α is also increased. Furthermore, as shown in FIG. 30B, among polypodna preparations including 240 nucleotides, hexapodna$_{40}$ showed the highest TNF-α release. These results showed that an increasing in the number of pods is effective for increasing the immune stimulation activity of CpGDNA.

Example 24-1

Uptake of DNA in RAW264.7 Cell

An Alexa Fluor 488-labeled DNA sample was prepared with the use of the above-mentioned material and method, as well as in the same manner as in Example 1 by using the sequences in Table 1. RAW264.7 cells were placed on a 96-well plate at a density of $5 \times 10^4$ cells/well, and incubated together with Alexa Fluor 488-labeled ssDNA, dsDNA, or polypodna at 37° C. or 4° C. for 8 hours. Thereafter, the cells were washed with 200 µl of a phosphate buffered physiological saline solution (PBS) twice and collected. Then, the average fluorescence intensity (MFI) of the cells was measured by using CellQuest software (version 3.1, BD Biosciences) through flow cytometory (FACS Calibur, BD Biosciences, NJ, USA).

The results are shown in FIG. 31A. The average fluorescence intensity was higher in the order from octapodna, hexapodna, pentapodna, tetrapodna and tripodna. The cell release had the same tendency as in the case of cytokine release. This showed that when the number of pods is increased, the induction of cytokine is increased.

Example 24-2

Fluorescence Microscope Observation of DNA Uptake

RAW264.7 cells were seeded on a 13 mm-diameter glass cover slip, and incubated for 24 hours. The culture medium was substituted by Opti-MEM containing Alexa Fluor 488-labeled hexapodna$_{36}$. After incubation at 37° C. for three hours, the cells were washed with PBS three times, fixed with 4% paraformaldehyde for 20 minutes, and washed again with PBS three times. Then, in order to stain a nucleus, 60 nM 4',6-diamino-2-phenyl indole (DAPI) was added and incubated for 10 minutes, followed by washing with PBS three times. Then, the cover slip was loaded on a glass slide by SlowFade (registered trademark) Gold (Invitrogen, Carlsbad, Calif., USA), and observed by using a fluorescence microscope (Biozero BZ-8000, KEYENCE CORPORATION, Osaka, Japan).

The results are shown in FIGS. 31B to E. In the drawings, B denotes DAPI staining, C denotes Alexa Fluor 488-labeled hexapodna$_{36}$, D denotes a superimposed image, and E denotes a bright field. As shown in FIGS. 31B to E, fluorescence signals were detected in dots in a cell. This suggested that the cell uptake is carried out by endocytosis.

Example 25

TLR9-Dependent Activation

DNA samples were prepared in the same manner as in Example 1 by using the sequences of SEQ ID NOs.: 86 to 95 among the sequences in Table 1.

Next, in a manner described in the document (Blood, 2000; 96: 3029-39), bone marrow-derived dendritic cells (BMDC) were created from 8 to 10-week old male C57BL/6 mice and a TLR9 knockout mouse (TLR9-/-) having genetic background of C57BL/6. That is, femur and shank were washed with RPMI by using a 26-gauge needle, bone marrow cells were isolated. After the bone marrow cells were filtrated through a 40 μm cell filter (BD Falcon, Franklin Lakes, N.J., USA), the bone marrow cells were suspended again in 0.86% ammonium chloride for 5 minutes to dissolve the erythrocyte.

Thereafter, in RPMI supplemented with 10% heat inactivated FBS, 0.2% sodium bicarbonate, 100 IU/ml penicillin, 100 μg/ml streptomycin, 2 mML-glutamine, 0.5 mM monothioglycerol and 100 ng/ml mouse recombinant Flt-3 ligand (Peprotech, Rocky Hill, N.J., USA), remaining cells were cultured at a density of $5 \times 10^6$ cells/ml for eight days. The cells were proliferated in 5% $CO_2$-containing humidified air at 37° C. On day 7 of the culture, non-cohesive cells were collected and the cells were used as BMDC. For release experiment of cytokine, the cells were plated again on a 96-well culture plate at a density of $3 \times 10^5$ cells/well. The cells were incubated together with 2 μg/ml ssDNA (Tripodna (0-18-18)-1-02) or polypodna. Thereafter, the culture supernatant was collected, and stored at −80° C. before used for Enzyme-Linked Immunosorbent Assay (ELISA). The concentration of the mouse IL-6 was measured by using an OptEIA™ set (Pharmingen, San Diego, Calif., USA).

Figure 32:
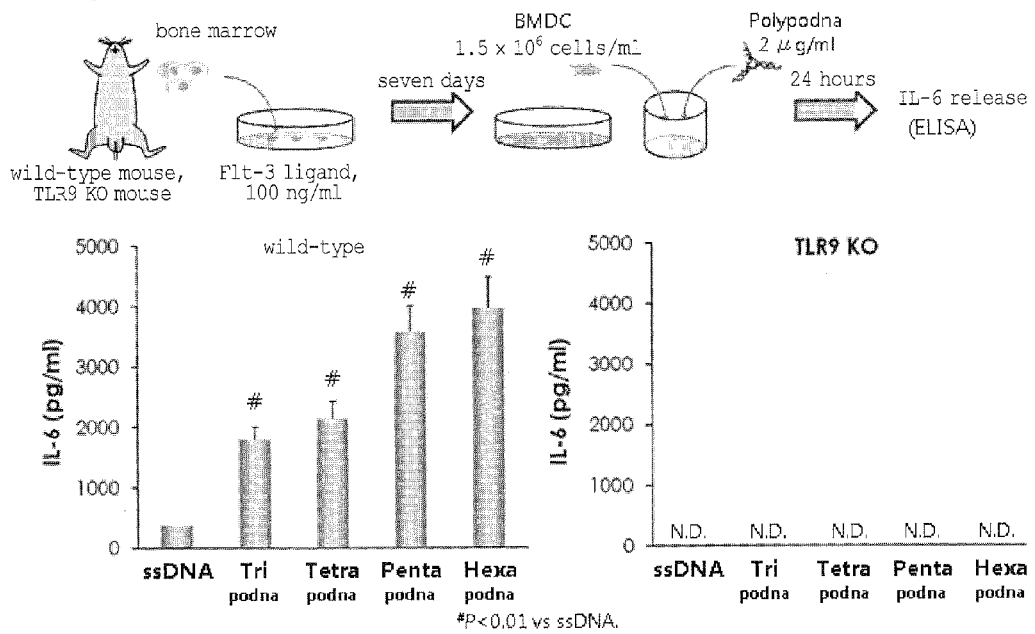
FIG. 32 Graphs showing that activation of IL-6 release by polypodna preparations is carried out in a TLR9-dependent manner.

The results are shown in FIG. 32. It was made clear that the release of IL-6 by hydrogel prepared by polypodna containing CpG was dependent upon TLR9.

Example 26

Monocyte-Dependent Uptake of Polypodna

DNA samples were prepared in the same manner as in Example 1 by using the sequences of SEQ ID NOs.: 96 to 104 among the sequences in Table 1.

Human peripheral blood monocytes (PBMC) were isolated from the peripheral blood of healthy volunteer according to the manufacturer's protocol by Ficoll-Paque PLUS (GE healthcare, Piscataway, N.J., USA) density gradient centrifugation. The collected PBMCs were plated again on a 48-well culture plate at a density of $6 \times 10^5$ cells/well, and used for release experiment of cytokine. The PBMC at a density of $6 \times 10^5$ cells/well were incubated together with a 2 μg/ml Alexa Fluor 488-labeled polypodna preparation on a 96-well culture plate for four hours. Thereafter, the cells were washed with 200 μl of a phosphate buffered physiological saline solution twice. Then, the fluorescence intensity of the cell was analyzed by using CellQuest software (version 3.1, BD Biosciences) through flow cytometory (FACS Calibur, BD Biosciences, Franklin Lakes, N.J., USA). For examination of PBMC, cells were gated based on forward scattering (FSC) and side scattering (SSC) properties (Clin Chem, 1998; 44: 966-72.). Thereafter, MFI of the cells in a monocyte-rich region 1 and a lymphocyte-rich region 2 were measured.

Figure 33:
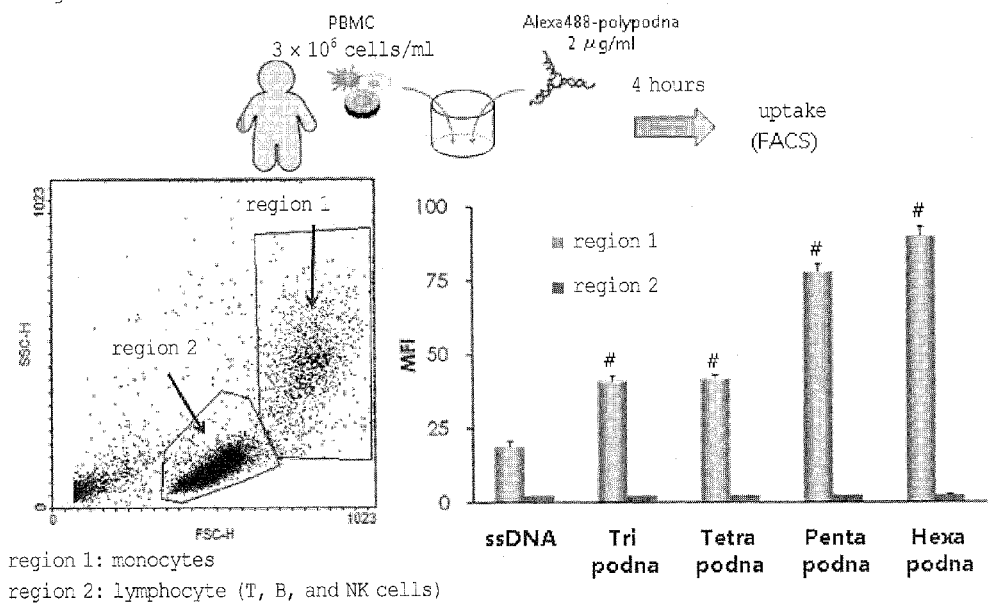
FIG. 33 A graph showing that polypodna preparations are taken up into a cell by monocytes.

The results are shown in FIG. 33. It was made clear that the uptake of polypodna was caused by monocytes.

Example 27

Induction of IL-6 mRNA Expression

Each DNA sample was prepared in the same manner as in Example 1 by using ODNs shown in Table 11 below among the sequences in Table 1.

TABLE 11

| CpG ssDNA | hexapodna(8-16-16)-2-01 |
| | hexapodna(8-16-16)-3-01 |
| CpG hexapodna | hexapodna(8-16-16)-2-01 to 06 |
| | hexapodna(8-16-16)-4-01 to 06 |
| CpG DNA hydrogel | hexapodna(8-16-16)-2-01 to 06 |
| | hexapodna(8-16-16)-3-01 to 06 |
| GpC ssDNA | hexapodna(8-16-16)-5-01 |
| | hexapodna(8-16-16)-6-01 |
| GpC hexapodna | hexapodna(8-16-16)-5-01 to 06 |
| | hexapodna(8-16-16)-7-01 to 06 |
| GpC DNA hydrogel | hexapodna(8-16-16)-5-01 to 06 |
| | hexapodna(8-16-16)-6-01 to 06 |

To the skin of the back of a C57BL/6 mouse under anesthesia with isoflurane, each DNA sample was injected in an amount of 200 μg/mouse. At a predetermined interval after the injection, the mouse was subjected to anesthesia with isoflurane, the skin of the back as well as inguinal and axillary lymph nodes were collected from the injection site and the local lymph node, respectively. The total RNA of the skin sample was extracted by using RNeasy mini kit (QIAGEN GmbH, Hilden, Germany) according to the manufacturer's protocol. The total RNA of the lymph node was extracted by using Sepasol RNAI super (NACALAI TESQUE, INC.). The extracted RNA was subjected to reverse transcription by using ReverTra Ace (registered trademark) qPCR RT Kit (TOYOBO, Osaka, Japan). For quantitative analysis of mRNA expression, RT-PCR of total RNA was carried out by using KAPA SYBR FAST ABI Prism 2X qPCR Master Mix (KAPA BIOSYSTEMS, Boston, Mass., USA). ODN primers used for amplification are shown in Table 12 below. An amplified product was detected on line through intercalation of SYBR GREEN as fluorescence dye by using StepOnePlus Real Time PCR System (Applied Biosystems, Foster City, Calif., USA). IL-6 mRNA expression was normalized in the mRNA level of β-actin.

TABLE 12

| | | | |
|---|---|---|---|
| IL-6 | forward | (5'-GTTCTCTGGGAAATCGTGGA-3') | (SEQ ID NO.: 165) |
| | reverse | (5'-TGTACTCCAGGTAGCTATGG-3') | (SEQ ID NO.: 166) |
| β-actin | forward | (5'-CATCCGTAAAGACCTCTATGC-3') | (SEQ ID NO.: 167) |
| | reverse | (5'-ATGGAGCCACCGATCCACA-3') | (SEQ ID NO.: 168) |

The results are shown in FIG. 34. It was made clear that the CpG hydrogel induced expression of IL-6 mRNA strongly and continuously.

Example 28

Induction of Adaptive Immune Response by OVA/CpG DNA Hydrogel (28-1) Collection of Serum Samples DNA samples were prepared in the same manner as in Example 1 by using the sequences in Table 1. Under anesthesia with isoflurane, a complete Freund's adjuvant (CFA) containing 200 μg of the DNA sample and 50 μg of OVA (10 μl/administration) or 50 μg of OVA (20 μl/administration) was injected to the skin of the back of a C57BL/6 mouse. Three times, that is, on Days 0, 7 and 14, the mouse was subjected to immunization. Seven days after the final immunization, the mouse was sacrificed, and the serum and the spleen were collected. The serum sample was stored at −80° C. before measurement.

(28-2) OVA-Specific IgG

For measuring a total IgG level specific to OVA by ELISA, the serum sample was continuously diluted. That is, a 96-well flat-bottomed plate was covered with OVA (1 mg/ml) at 4° C. for 8 to 16 hours. Then, the well was blocked with 0.5 w/w % Tween-20 in a phosphate buffered physiological saline solution (T-PBS) containing 5% BSA. After the sample was washed with T-PBS, 100 μl of the diluted serum sample was continuously added to each well. After incubation at 37° C. for two hours, the well was washed with T-PBS five times, and then 100 μl of anti-IgG-HRP conjugate (Sigma, St. Louis, Mo., USA) which had been diluted at 3000:1 with 5% BSA-containing T-PBS was added to each well. After incubation at 37° C. for one hour, each well was washed with T-PBS, and then 200 μl of a newly prepared o-phenylenediamine dihydrochloride (Wako Pure Chemical Industries, Ltd., Osaka, Japan) solution containing 20 μl of hydrogen peroxide in citric acid phosphate buffer solution (pH 5) was added to each well. Four minutes after the incubation, 50 μl of 1 M sulfuric acid was added, and then the absorbance at 490 nm was measured.

The results are shown in the left view of FIG. 35. It was made clear that IgG titer is increased when it is in a hydrogel state.

(28-3) IFN-γ from Spleen Cell

Seven days after the final immunization, the splenocytes were isolated by mechanical dissection. The mixed erythrocytes were dissolved with 1.5 M ammonium chloride. In the presence of OVA (1 mg/ml), splenocytes were cultured at a density of 5×10$^6$ cells/ml in a 96-well culture plate for four days. The supernatant was collected and stored at −80° C. before use. The concentration of IFN-γ was measured according to the manufacturer's protocol (Ready-SET-Go! mouse IFN-γ ELISA, eBioscience, San Diego, Calif., USA) by ELISA.

The results are shown in the center view of FIG. 35. This shows that the concentration of IFN-γ is increased when it is in a hydrogel state.

(28-4) CTL Assay

Seven days after the final immunization, the splenocytes were isolated by mechanical dissection. The mixed erythrocytes were dissolved with 1.5 M ammonium chloride. In order to prepare CTL, 5×10$^6$ EG7-OVA cells which had been treated with mitomycin C and the splenocytes (5×10$^7$ cells) were co-cultured at 37° C. in 5% $CO_2$ for five days. Target cells, that is, EG7-OVA and EL4 were labeled with $^{51}$Cr-labeled sodium chromate ($Na_2{}^{51}CrO_4$, FUJIFILM RI Pharma Co., Ltd., Tokyo, Japan). The boost splenocytes were diluted continuously, and incubated together with the target cells at 37° C. for four hours. From the incubation without including an effector cell (spleen cell) and with including 1% Triton-X, natural release of $^{51}$Cr itself and maximum release were evaluated, respectively. The radioactivity of the supernatant was measured by using a gamma counter. The percentage of the specific dissolution was calculated according to the following equation:

% of specific dissolution=(observed release−natural release)/(maximum release−natural release)

The results are shown in the right view of FIG. 35. This shows that specific dissolution is higher in a hydrogel state than in a single strand state or in a state of a nucleic acid unit (polypodna).

Example 29

Adverse Effect

DNA samples were prepared in the same manner as in Example 1 by using the sequences in Table 1.

To the skin of the back of a C57BL/6 mouse under anesthesia with isoflurane, 200 mg of the DNA sample and 50 μg of OVA (10 μl), and CFA containing 50 mg of OVA (10 μl), or 100 μg of Alum and 50 μg of OVA (20 μl) were infused. Seven days after the infusion, the skin including the infusion site was extracted, fixed in 4% paraformaldehyde, and incorporated into paraffin. The paraffin was thinly cut into 5 μm slice, and then the slice was subjected to hematoxylin-eosin staining. The stained sample was observed under microscope (Biozero BZ-8000 manufactured by KEYENCE CORPORATION, Osaka, Japan) for histological evaluation. As mentioned above, at an interval of one week, seven days after the third immunization, spleen was collected from a C57BL/6 mouse in different pairs. The weight of the spleen was measured to evaluate the splenomegaly.

Figure 36:
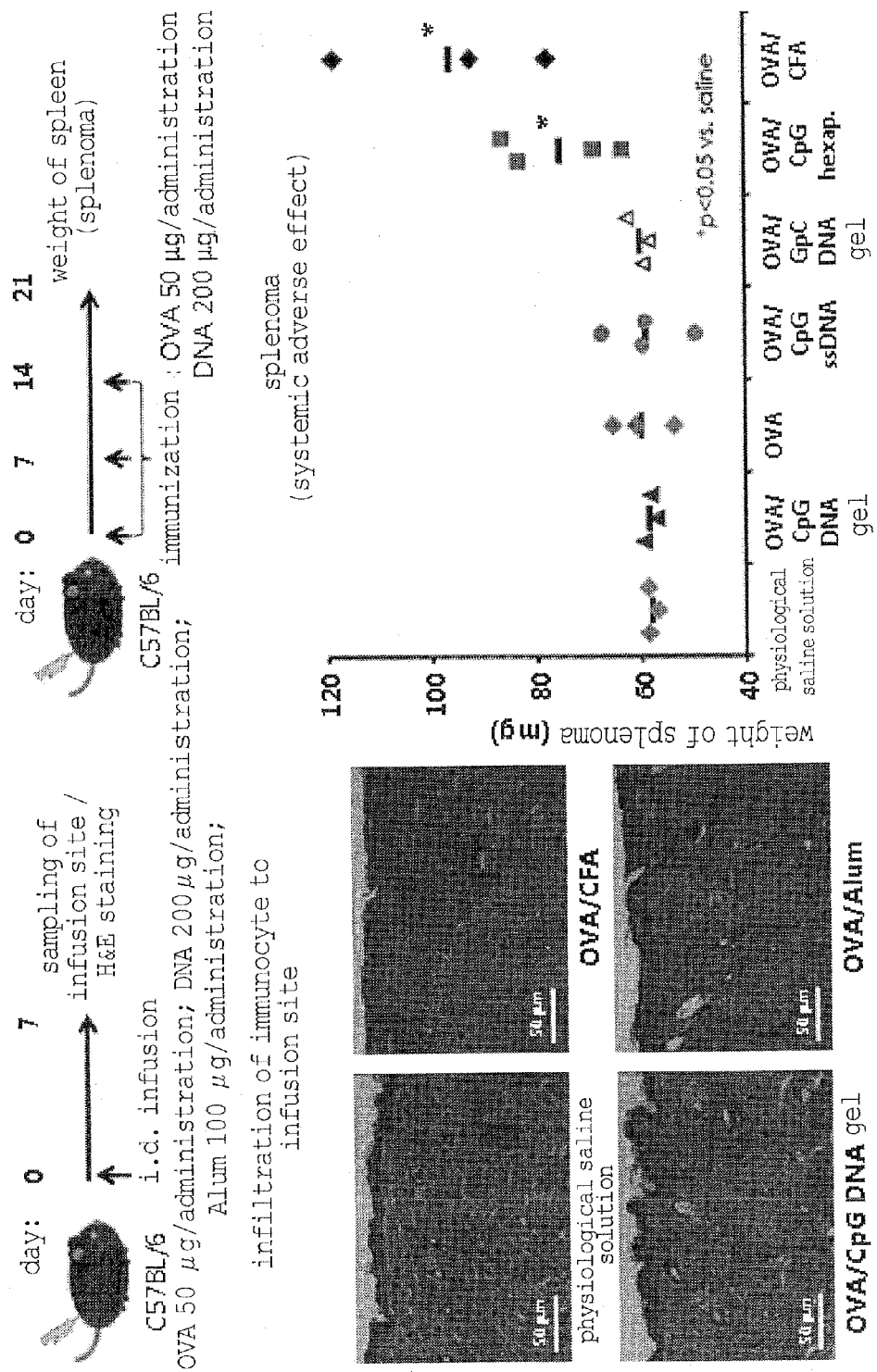
FIG. 36 Photographs showing infiltration of immune cells at an injection site (left view) and a graph showing spleen weight (right view) in comparison with various adjuvants.

The results are shown in FIG. 36. As shown in the left view of FIG. 36, it was made clear that the hydrogel gives small infiltration of immune cells to an infusion site and a small local adverse effect. Furthermore, as shown in the right view of FIG. 36, it was made clear that the hydrogel gives small splenomegaly and a small systemic adverse effect.

INDUSTRIAL APPLICABILITY

The present invention is applicable for various applications such as sustained release agents, immunostimulants and tissue transferability DNA. A gel produced from the composition of the present invention is considered to be utilized as a controlled release system in wide variety of substances (drugs, antigens and cells). Furthermore, by incorporating an immunological activation structure, typically, a CpG motif, a function as an immunological adjuvant can be added. Thus, a synergistic effect with an anticancer drug, antigen protein, and immunocyte can be expected. Furthermore, the gel can be administered in a sol (solution) state, and therefore it can be developed as a spray agent, so that it is considered to be useful for administering antigen to the nasal cavity or the like, and can be widely utilized for therapy requiring control of the immune response.

Sequence Listing

The invention claimed is:

1. A nucleic acid gel composition comprising a mixture of two or more oligonucleotides composed of a cohesive protruding end moiety and a complementary base sequence moiety in the composition at a nucleic acid concentration of 3.2/x mM or more and containing a salt at a concentration of 640 mM/x-60 mM or more in terms of a NaCl concentration, wherein the nucleic acid gel composition does not contain a nucleic acid linking enzyme, and wherein x is the number of bases in the protruding end moiety, the cohesive protruding end moiety is a single strand nucleic acid moiety having 4 or more nucleotide length and being complementary to a cohesive protruding end moiety in at least one other oligonucleotide to such a degree as to form a double strand sequence showing a melting temperature that is equal to or higher than the body temperature in a physiological condition, and the complementary base sequence moiety that binds to the other oligonucleotide in a complementary manner has 8 or more nucleotide length and is complementary to the complementary base sequence moiety in the other oligonucleotide to such a degree as to form a double strand sequence showing a melting temperature that is equal to or higher than the body temperature in a physiological condition.

2. The nucleic acid gel composition according to claim 1, wherein the cohesive protruding end includes a palindrome sequence structure.

3. The nucleic acid gel composition according to claim 1, wherein one or more of the two or more oligonucleotides include a CpG motif.

4. The nucleic acid gel composition according to claim 1, wherein the two or more oligonucleotides are 2 to 8 oligonucleotides.

5. The nucleic acid gel composition according to claim 1, wherein the cohesive protruding end moiety has 4 to 12 nucleotide length and the complementary base sequence moiety has 8 to 45 nucleotide length.

* * * * *

```
                       SEQUENCE LISTING

<160> NUMBER OF SEQ ID NOS: 174

<210> SEQ ID NO 1
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 1
acgttcgtca acgtctgtgc tctcacgttg acgctgtcga                          40

<210> SEQ ID NO 2
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 2
acgttcgaca gcgtcaacgt gaaacgtgaa gcgtctgcga                          40

<210> SEQ ID NO 3
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 3
acgttcgcag acgcttcacg ttgagcacag acgttgacga                          40

<210> SEQ ID NO 4
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 4
acgttcgctg acgttgcaga catcacgttg acgctgtcga                          40

<210> SEQ ID NO 5
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 5
acgttcgcag acgcttcacg ttgcagacag acgttgacga                          40

<210> SEQ ID NO 6
<211> LENGTH: 40
```

```
<212> TYPE: DNA
<213> ORGANISM: Artificial
<220> FEATURE:
<223> OTHER INFORMATION: Synthetic Construct; Nucleic acid monomer

<400> SEQUENCE: 6
acgttcgtca acgtctgtct gctgtctgca acgtcagcga                          40

<210> SEQ ID NO 7
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 7
acgttcgtca acgtctgtgc tcgcagcgtc ttaacgtcga                          40

<210> SEQ ID NO 8
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 8
acgttcgacg ttaagacgct gctgtctgca acgtcagcga                          40

<210> SEQ ID NO 9
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 9
acgttcgacg ttaagacgct gcagacgttc aggactacga                          40

<210> SEQ ID NO 10
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 10
acgttcgtag tcctgaacgt cttgtctgca acgtcagcga                          40

<210> SEQ ID NO 11
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 11
acgttcgatc cagacgttgt agcctgacgt cgtacatcga                          40

<210> SEQ ID NO 12
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 12
```
acgttcgatg tacgacgtca ggtcacgttg acgctgtcga        40

<210> SEQ ID NO 13
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 13
acgttcgctg acgttgcaga cactacaacg tctggatcga        40

<210> SEQ ID NO 14
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 14
agctaggcac cgtagtcaat cgccgatgtg tccaaagcct        40

<210> SEQ ID NO 15
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 15
agctaggctt tggacacatc ggtgctccta ccgtactcct        40

<210> SEQ ID NO 16
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 16
agctaggagt acggtaggag cagtttcggc atgtccacct        40

<210> SEQ ID NO 17
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 17
agctaggtgg acatgccgaa accgattgac tacggtgcct        40

<210> SEQ ID NO 18
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 18
aacgtttacg cacgacatca gcgtctggac gcttcgtcga        40

<210> SEQ ID NO 19
<211> LENGTH: 40
<212> TYPE: DNA
<213> ORGANISM: Artificial

```
<220> FEATURE:
<223> OTHER INFORMATION: Synthetic Construct; Nucleic acid monomer

<400> SEQUENCE: 19
aacgtttcga cgaagcgtcc agatctcgtc aacgctgcga                    40

<210> SEQ ID NO 20
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 20
aacgtttcgc agcgttgacg agacagacgc tgtgacgcta                    40

<210> SEQ ID NO 21
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 21
aacgtttagc gtcacagcgt ctgcgctgat gtcgtgcgta                    40

<210> SEQ ID NO 22
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 22
acgtacgtta gcacgacatc agcgtctgac gcttcgtcga                    40

<210> SEQ ID NO 23
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 23
acgtacgttc gacgaagcgt cagatctcgt caacgctgca                    40

<210> SEQ ID NO 24
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 24
acgtacgttg cagcgttgac gagacagacg cttgacgcta                    40

<210> SEQ ID NO 25
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 25
acgtacgtta gcgtcaagcg tctgcgctga tgtcgtgcta                    40
```

```
<210> SEQ ID NO 26
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 26
acgttaacgt tgcacgacat cagcgtctga cgctcgtcga                              40

<210> SEQ ID NO 27
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 27
acgttaacgt tcgacgagcg tcagatctcg caacgctgca                              40

<210> SEQ ID NO 28
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 28
acgttaacgt tgcagcgttg cgagacagac gcttgacgca                              40

<210> SEQ ID NO 29
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 29
acgttaacgt tgcgtcaagc gtctgcgctg atgtcgtgca                              40

<210> SEQ ID NO 30
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 30
acgtcatgac gttgcacgac atcacgttga cgctcgtcga                              40

<210> SEQ ID NO 31
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 31
acgtcatgac gttcgacgag cgtcaatctc gcaacgtgca                              40

<210> SEQ ID NO 32
<211> LENGTH: 40
<212> TYPE: DNA
<213> ORGANISM: Artificial
<220> FEATURE:
<223> OTHER INFORMATION: Synthetic Construct; Nucleic acid monomer
```

<400> SEQUENCE: 32
acgtcatgac gttgcacgtt gcgagacaga cgcttgacga         40

<210> SEQ ID NO 33
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 33
acgtcatgac gttcgtcaag cgtctgcgtg atgtcgtgca         40

<210> SEQ ID NO 34
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 34
tcagagtcag tctgcacgac atcacgttga cgctcgtcga         40

<210> SEQ ID NO 35
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 35
tcagagtcag tctcgacgag cgtcaatctc gcaacgtgca         40

<210> SEQ ID NO 36
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 36
tcagagtcag tctgcacgtt gcgagacaga cgcttgacga         40

<210> SEQ ID NO 37
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 37
tcagagtcag tctcgtcaag cgtctgcgtg atgtcgtgca         40

<210> SEQ ID NO 38
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 38
gactgactct gatgcacgac atcacgttga cgctcgtcga         40

<210> SEQ ID NO 39

```
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 39
gactgactct gatcgacgag cgtcaatctc gcaacgtgca                               40

<210> SEQ ID NO 40
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 40
gactgactct gatgcacgtt gcgagacaga cgcttgacga                               40

<210> SEQ ID NO 41
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 41
gactgactct gatcgtcaag cgtctgcgtg atgtcgtgca                               40

<210> SEQ ID NO 42
<211> LENGTH: 24
<212> TYPE: DNA
<213> ORGANISM: Artificial
<220> FEATURE:
<223> OTHER INFORMATION: Synthetic Construct; Nucleic acid monomer

<400> SEQUENCE: 42
gactgactct gaacgtcagc gtta                                                24

<210> SEQ ID NO 43
<211> LENGTH: 24
<212> TYPE: DNA
<213> ORGANISM: Artificial
<220> FEATURE:
<223> OTHER INFORMATION: Synthetic Construct; Nucleic acid monomer

<400> SEQUENCE: 43
gactgactct gataacgctg acgt                                                24

<210> SEQ ID NO 44
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 44
tcctgacgtt gctagacgct gtcagcacgt cgtagtgcaa                               40

<210> SEQ ID NO 45
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 45
```
tcctgacgtt gctagacgct gtcagcacgt cgtagtgcaa        40

<210> SEQ ID NO 46
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 46
tcctgacgtt gatcgacgtc tgcttgacgc tcagctgcaa        40

<210> SEQ ID NO 47
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 47
tcctgacgtt gcagctgagc gtcagacgct gatctagcaa        40

<210> SEQ ID NO 48
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 48
tcctgacgtt gctagatcag cgtcctcacg ttgactacaa        40

<210> SEQ ID NO 49
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 49
tcctgacgtt gtagtcaacg tgagtgacag cgtctagcaa        40

<210> SEQ ID NO 50
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 50
tcctgacgtt gcagctgagc gtcatgacag cgtctagcaa        40

<210> SEQ ID NO 51
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 51
cgtcaggacg ttgaatccat gacgttgtat gactgcaacg        40

<210> SEQ ID NO 52
<211> LENGTH: 40
<212> TYPE: DNA

```
<213> ORGANISM: Artificial
<220> FEATURE:
<223> OTHER INFORMATION: Synthetic Construct; Nucleic acid monomer

<400> SEQUENCE: 52
cgtcaggacg ttgcagtcat acaatcctga cgctctgacg                                40

<210> SEQ ID NO 53
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 53
cgtcaggacg tcagagcgtc aggacgttca tcagtatacg                                40

<210> SEQ ID NO 54
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 54
cgtcaggacg tatactgatg aacgaagtga cgtctcaacg                                40

<210> SEQ ID NO 55
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 55
cgtcaggacg ttgagacgtc acttatcgac gtctgagacg                                40

<210> SEQ ID NO 56
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 56
cgtcaggacg tctcagacgt cgatcgtcat ggattcaacg                                40

<210> SEQ ID NO 57
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 57
cgtcaggacg ttaactgatg aacgcgtcat ggattcaacg                                40

<210> SEQ ID NO 58
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 58
agtctcgctg acgttgcaga catcacgttg acgctgtcga                                40
```

<210> SEQ ID NO 59
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 59
agtctcgaca gcgtcaacgt gaaacgtgaa gcgtctgcga                    40

<210> SEQ ID NO 60
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 60
agtctcgcag acgcttcacg ttgcagacag acgttgacga                    40

<210> SEQ ID NO 61
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 61
agtctcgtca acgtctgtct gctgtctgca acgtcagcga                    40

<210> SEQ ID NO 62
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 62
gcagacgacg ttgaatccat gacgttgtat gactgcaacg                    40

<210> SEQ ID NO 63
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 63
gcagacgacg ttgcagtcat acaatcctga cgctctgacg                    40

<210> SEQ ID NO 64
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 64
gcagacgacg tcagagcgtc aggacgttca tcagtatacg                    40

<210> SEQ ID NO 65
<211> LENGTH: 40
<212> TYPE: DNA
<213> ORGANISM: Artificial
<220> FEATURE:

<223> OTHER INFORMATION: Synthetic Construct; Nucleic acid monomer

<400> SEQUENCE: 65
gcagacgacg tatactgatg aacgaagtga cgtctcaacg            40

<210> SEQ ID NO 66
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 66
gcagacgacg ttgagacgtc acttatcgac gtctgagacg            40

<210> SEQ ID NO 67
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 67
gcagacgacg tctcagacgt cgatcgtcat ggattcaacg            40

<210> SEQ ID NO 68
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 68
tcctgagctt gctagagcct gtcaggagca gctagtgcaa            40

<210> SEQ ID NO 69
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 69
tcctgagctt gcactagctg ctccagcaga gctcgatcaa            40

<210> SEQ ID NO 70
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 70
tcctgagctt gatcgagctc tgcttgagcc tcagctgcaa            40

<210> SEQ ID NO 71
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 71
tcctgagctt gcagctgagg ctcagagcct gatctagcaa            40

```
<210> SEQ ID NO 72
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 72
tcctgagctt gctagatcag gctcctcagc ttgactacaa                40

<210> SEQ ID NO 73
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 73
tcctgagctt gtagtcaagc tgagtgacag gctctagcaa                40

<210> SEQ ID NO 74
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 74
gctcaggagc ttgaatccat gagcttgtat gactgcaagc                40

<210> SEQ ID NO 75
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 75
gctcaggagc ttgcagtcat acaatcctga gcctctgagc                40

<210> SEQ ID NO 76
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 76
gctcaggagc tcagaggctc aggagcttca tcagtatagc                40

<210> SEQ ID NO 77
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 77
gctcaggagc tatactgatg aagcaagtga gctctcaagc                40

<210> SEQ ID NO 78
<211> LENGTH: 40
<212> TYPE: DNA
<213> ORGANISM: Artificial
<220> FEATURE:
<223> OTHER INFORMATION: Synthetic Construct; Nucleic acid monomer
```

<400> SEQUENCE: 78
gctcaggagc ttgagagctc acttatgcag ctctgagagc                           40

<210> SEQ ID NO 79
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 79
gctcaggagc tctcagagct gcatgctcat ggattcaagc                           40

<210> SEQ ID NO 80
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 80
gctgtccagc ttgaatccat gagcttgtat gactgcaagc                           40

<210> SEQ ID NO 81
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 81
gctgtccagc ttgcagtcat acaatcctga gcctctgagc                           40

<210> SEQ ID NO 82
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 82
gctgtccagc tcagaggctc aggagcttca tcagtatagc                           40

<210> SEQ ID NO 83
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 83
gctgtccagc tatactgatg aagcaagtga gctctcaagc                           40

<210> SEQ ID NO 84
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 84
gctgtccagc ttgagagctc acttatgcag ctctgagagc                           40

<210> SEQ ID NO 85
<211> LENGTH: 40

```
<212> TYPE: DNA
<213> ORGANISM: Artificial
<220> FEATURE:
<223> OTHER INFORMATION: Synthetic Construct; Nucleic acid monomer

<400> SEQUENCE: 85
gctgtccagc tctcagagct gcatgctcat ggattcaagc                          40

<210> SEQ ID NO 86
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 86
tcgtcaacgt ctgtgctctc acgttgacgc tgtcga                              36

<210> SEQ ID NO 87
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 87
tcgacagcgt caacgtgaaa cgtgaagcgt ctgcga                              36

<210> SEQ ID NO 88
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 88
tcgcagacgc ttcacgttga gcacagacgt tgacga                              36

<210> SEQ ID NO 89
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 89
tcgctgacgt tgcagacatc acgttgacgc tgtcga                              36

<210> SEQ ID NO 90
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 90
tcgcagacgc ttcacgttgc agacagacgt tgacga                              36

<210> SEQ ID NO 91
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 91
```
tcgtcaacgt ctgtctgctg tctgcaacgt cagcga      36

<210> SEQ ID NO 92
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 92
tcgtcaacgt ctgtgctcgc agcgtcttaa cgtcga      36

<210> SEQ ID NO 93
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 93
tcgacgttaa gacgctgctg tctgcaacgt cagcga      36

<210> SEQ ID NO 94
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 94
tcgacgttaa gacgctgcag acgttcagga ctacga      36

<210> SEQ ID NO 95
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 95
tcgtagtcct gaacgtcttg tctgcaacgt cagcga      36

<210> SEQ ID NO 96
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 96
tcgtcgttcc gtcgttacac tgctctggcg gtcgtt      36

<210> SEQ ID NO 97
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 97
aacgaccgcc agagcagtcg tgtcgtacta cgacga      36

<210> SEQ ID NO 98
<211> LENGTH: 36
<212> TYPE: DNA
<213> ORGANISM: Artificial

<220> FEATURE:
<223> OTHER INFORMATION: Synthetic Construct; Nucleic acid monomer

<400> SEQUENCE: 98
tcgtcgtagt acgacacggt aacgacggaa cgacga                                    36

<210> SEQ ID NO 99
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 99
tcgtcgtagt acgacacggt cgtaagcctg gtcgta                                    36

<210> SEQ ID NO 100
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 100
tacgaccagg cttacgacgt aacgacggaa cgacga                                    36

<210> SEQ ID NO 101
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 101
tacgaccagg cttacgacag tctagctgat cgacga                                    36

<210> SEQ ID NO 102
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 102
tcgtcgatca gctagactgt aacgacggaa cgacga                                    36

<210> SEQ ID NO 103
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 103
tcgtcgatca gctagactgc tgtcgatgcc aacgac                                    36

<210> SEQ ID NO 104
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 104
gtcgttggca tcgacagcgt aacgacggaa cgacga                                    36

<210> SEQ ID NO 105
<211> LENGTH: 30
<212> TYPE: DNA
<213> ORGANISM: Artificial
<220> FEATURE:
<223> OTHER INFORMATION: Synthetic Construct; Nucleic acid monomer

<400> SEQUENCE: 105
ctagcgttgc tagtggtgtc caaacgctag                                      30

<210> SEQ ID NO 106
<211> LENGTH: 30
<212> TYPE: DNA
<213> ORGANISM: Artificial
<220> FEATURE:
<223> OTHER INFORMATION: Synthetic Construct; Nucleic acid monomer

<400> SEQUENCE: 106
ctagcgtttg gacactcagc ctaacgctag                                      30

<210> SEQ ID NO 107
<211> LENGTH: 30
<212> TYPE: DNA
<213> ORGANISM: Artificial
<220> FEATURE:
<223> OTHER INFORMATION: Synthetic Construct; Nucleic acid monomer

<400> SEQUENCE: 107
ctagcgtttg gacactcagc ctaacgctag                                      30

<210> SEQ ID NO 108
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 108
tcgctgacgt tgcagacatc acgttgacgc tgtcga                               36

<210> SEQ ID NO 109
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 109
tcgacagcgt caacgtgatg tctgcaacgt cagcga                               36

<210> SEQ ID NO 110
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 110
tcgtcaacgt ctgtgctctc acgttgacgc tgtcga                               36

<210> SEQ ID NO 111
<211> LENGTH: 36
<212> TYPE: DNA
<213> ORGANISM: Artificial
<220> FEATURE:
<223> OTHER INFORMATION: Synthetic Construct; Nucleic acid monomer

```
<400> SEQUENCE: 111
tcgacagcgt caacgtgaaa cgtgaagcgt ctgcga                                  36

<210> SEQ ID NO 112
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 112
tcgcagacgc ttcacgttga gcacagacgt tgacga                                  36

<210> SEQ ID NO 113
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 113
tcgcagacgc ttcacgttgc agacagacgt tgacga                                  36

<210> SEQ ID NO 114
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 114
tcgtcaacgt ctgtctgctg tctgcaacgt cagcga                                  36

<210> SEQ ID NO 115
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 115
tcgtcaacgt ctgtgctcgc agcgtcttaa cgtcga                                  36

<210> SEQ ID NO 116
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 116
tcgacgttaa gacgctgctg tctgcaacgt cagcga                                  36

<210> SEQ ID NO 117
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 117
tcgacgttaa gacgctgcag acgttcagga ctacga                                  36

<210> SEQ ID NO 118
```

```
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 118
tcgtagtcct gaacgtcttg tctgcaacgt cagcga                              36

<210> SEQ ID NO 119
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 119
tcgatgtacg acgtcaggtc acgttgacgc tgtcga                              36

<210> SEQ ID NO 120
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 120
tcgctgacgt tgcagacact acaacgtctg gatcga                              36

<210> SEQ ID NO 121
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 121
tcgatccaga cgttgtagcc tgacgtcgta catcga                              36

<210> SEQ ID NO 122
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 122
tcgatgtacg acgtcagatc acgttgacgc tgtcga                              36

<210> SEQ ID NO 123
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 123
tcgatccaga cgttgtagaa cgtcgactca gatcga                              36

<210> SEQ ID NO 124
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 124
```
tcgatctgag tcgacgttat acaacgcctg gatcga				36

<210> SEQ ID NO 125
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 125
tcgatccagg cgttgtatct atccacacgc tgacga				36

<210> SEQ ID NO 126
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 126
tcgtcagcgt gtggataggt ctccagacgt catcga				36

<210> SEQ ID NO 127
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 127
tcgatgacgt ctggagactc tgacgtcgta catcga				36

<210> SEQ ID NO 128
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 128
ctgacgttct gctgcagaca tcagcttgag cctgtgcaag			40

<210> SEQ ID NO 129
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 129
cttgcacagg ctcaagctga aagctggtgc agaacgtcag			40

<210> SEQ ID NO 130
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 130
ctgacgttct gcaccagctt gagcacagag cttgagcaag			40

<210> SEQ ID NO 131
<211> LENGTH: 40
<212> TYPE: DNA

```
<213> ORGANISM: Artificial
<220> FEATURE:
<223> OTHER INFORMATION: Synthetic Construct; Nucleic acid monomer

<400> SEQUENCE: 131
cttgctcaag ctctgtgctc gcaggctctt agaacgtcag                    40

<210> SEQ ID NO 132
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 132
ctgacgttct aagagcctgc agagcttcag gactagcaag                    40

<210> SEQ ID NO 133
<211> LENGTH: 40
<212> TYPE: DNA
<213> ORGANISM: Artificial
<220> FEATURE:
<223> OTHER INFORMATION: Synthetic Construct; Nucleic acid monomer

<400> SEQUENCE: 133
cttgctagtc ctgaagctct tgtctgcagc agaacgtcag                    40

<210> SEQ ID NO 134
<211> LENGTH: 48
<212> TYPE: DNA
<213> ORGANISM: Artificial
<220> FEATURE:
<223> OTHER INFORMATION: Synthetic Construct; Nucleic acid monomer

<400> SEQUENCE: 134
ctgacgttct gctgcagaca gtcatcagtc agcttgagcc tgtgcaag           48

<210> SEQ ID NO 135
<211> LENGTH: 48
<212> TYPE: DNA
<213> ORGANISM: Artificial
<220> FEATURE:
<223> OTHER INFORMATION: Synthetic Construct; Nucleic acid monomer

<400> SEQUENCE: 135
cttgcacagg ctcaagctga ctgaagctaa gctggtgcag aacgtcag           48

<210> SEQ ID NO 136
<211> LENGTH: 48
<212> TYPE: DNA
<213> ORGANISM: Artificial
<220> FEATURE:
<223> OTHER INFORMATION: Synthetic Construct; Nucleic acid monomer

<400> SEQUENCE: 136
ctgacgttct gcaccagctt agctgactga gcacagagct tgagcaag           48

<210> SEQ ID NO 137
<211> LENGTH: 48
<212> TYPE: DNA
<213> ORGANISM: Artificial
<220> FEATURE:
<223> OTHER INFORMATION: Synthetic Construct; Nucleic acid monomer

<400> SEQUENCE: 137
cttgctcaag ctctgtgctc agtcgcatgc aggctcttag aacgtcag           48
```

<210> SEQ ID NO 138
<211> LENGTH: 48
<212> TYPE: DNA
<213> ORGANISM: Artificial
<220> FEATURE:
<223> OTHER INFORMATION: Synthetic Construct; Nucleic acid monomer

<400> SEQUENCE: 138
ctgacgttct aagagcctgc atgctgactg tctgcagcag aacgtcag                    48

<210> SEQ ID NO 139
<211> LENGTH: 60
<212> TYPE: DNA
<213> ORGANISM: Artificial
<220> FEATURE:
<223> OTHER INFORMATION: Synthetic Construct; Nucleic acid monomer

<400> SEQUENCE: 139
ctagcgttgc tagtgctagc gttgctagtg gtgtccaaac gctaggtgtc caaacgctag       60

<210> SEQ ID NO 140
<211> LENGTH: 60
<212> TYPE: DNA
<213> ORGANISM: Artificial
<220> FEATURE:
<223> OTHER INFORMATION: Synthetic Construct; Nucleic acid monomer

<400> SEQUENCE: 140
ctagcgtttg gacacctagc gtttggacac tcagcctaac gctagtcagc ctaacgctag       60

<210> SEQ ID NO 141
<211> LENGTH: 60
<212> TYPE: DNA
<213> ORGANISM: Artificial
<220> FEATURE:
<223> OTHER INFORMATION: Synthetic Construct; Nucleic acid monomer

<400> SEQUENCE: 141
ctagcgttag gctgactagc gttaggctga cactagcaac gctagcacta gcaacgctag       60

<210> SEQ ID NO 142
<211> LENGTH: 60
<212> TYPE: DNA
<213> ORGANISM: Artificial
<220> FEATURE:
<223> OTHER INFORMATION: Synthetic Construct; Nucleic acid monomer

<400> SEQUENCE: 142
ctgacgttct gctgcagaca gtcacagtca tcagtgtcag tcagcttgag cctgtgcaag      60

<210> SEQ ID NO 143
<211> LENGTH: 60
<212> TYPE: DNA
<213> ORGANISM: Artificial
<220> FEATURE:
<223> OTHER INFORMATION: Synthetic Construct; Nucleic acid monomer

<400> SEQUENCE: 143
cttgcacagg ctcaagctga ctgacactga agctgcagct aagctggtgc agaacgtcag      60

<210> SEQ ID NO 144
<211> LENGTH: 60
<212> TYPE: DNA
<213> ORGANISM: Artificial
<220> FEATURE:

<223> OTHER INFORMATION: Synthetic Construct; Nucleic acid monomer

<400> SEQUENCE: 144
ctgacgttct gcaccagctt agctgcagct gcactggcat gcaggctctt agaacgtcag    60

<210> SEQ ID NO 145
<211> LENGTH: 60
<212> TYPE: DNA
<213> ORGANISM: Artificial
<220> FEATURE:
<223> OTHER INFORMATION: Synthetic Construct; Nucleic acid monomer

<400> SEQUENCE: 145
ctgacgttct aagagcctgc atgccagtgc tgactgtgac tgtctgcagc agaacgtcag    60

<210> SEQ ID NO 146
<211> LENGTH: 80
<212> TYPE: DNA
<213> ORGANISM: Artificial
<220> FEATURE:
<223> OTHER INFORMATION: Synthetic Construct; Nucleic acid monomer

<400> SEQUENCE: 146
ctgacgttct gctgcagaca gtcacagtca gctccagtca agctgcatga agctgcagct    60
aagctggtgc agaacgtcag                                               80

<210> SEQ ID NO 147
<211> LENGTH: 80
<212> TYPE: DNA
<213> ORGANISM: Artificial
<220> FEATURE:
<223> OTHER INFORMATION: Synthetic Construct; Nucleic acid monomer

<400> SEQUENCE: 147
ctgacgttct gcaccagctt agctgcagct tcatgcagct gcactgcatt gcactggcat    60
gcaggctctt agaacgtcag                                               80

<210> SEQ ID NO 148
<211> LENGTH: 80
<212> TYPE: DNA
<213> ORGANISM: Artificial
<220> FEATURE:
<223> OTHER INFORMATION: Synthetic Construct; Nucleic acid monomer

<400> SEQUENCE: 148
ctgacgttct aagagcctgc atgccagtgc aatgcagtgc tgactggagc tgactgtgac    60
tgtctgcagc agaacgtcag                                               80

<210> SEQ ID NO 149
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 149
ctagcgttgc tagtgctagc gttgctagtg ctagcgttgc tagtggtgtc caaacgctag    60
gtgtccaaac gctaggtgtc caaacgctag                                    90

<210> SEQ ID NO 150
<211> LENGTH: 90
<212> TYPE: DNA
<213> ORGANISM: Artificial

```
<220> FEATURE:
<223> OTHER INFORMATION: Synthetic Construct; Nucleic acid monomer

<400> SEQUENCE: 150
ctagcgtttg gacacctagc gtttggacac ctagcgtttg gacactcagc ctaacgctag    60
tcagcctaac gctagtcagc ctaacgctag                                    90

<210> SEQ ID NO 151
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 151
ctagcgttag gctgactagc gttaggctga ctagcgttag gctgacacta gcaacgctag    60
cactagcaac gctagcacta gcaacgctag                                    90

<210> SEQ ID NO 152
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 152
ctgacgttgc agacactgac gttgcagaca ctgacgttgc agacatcacg ttgacgctgt    60
tcacgttgac gctgttcacg ttgacgctgt                                    90

<210> SEQ ID NO 153
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 153
acagcgtcaa cgtgaacagc gtcaacgtga acagcgtcaa cgtgaaacgt gaagcgtctg    60
aacgtgaagc gtctgaacgt gaagcgtctg                                    90

<210> SEQ ID NO 154
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 154
cagacgcttc acgttcagac gcttcacgtt cagacgcttc acgttgcaga cagacgttga    60
gcagacagac gttgagcaga cagacgttga                                    90

<210> SEQ ID NO 155
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 155
tcaacgtctg tctgctcaac gtctgtctgc tcaacgtctg tctgctgtct gcaacgtcag    60
tgtctgcaac gtcagtgtct gcaacgtcag                                    90
```

```
<210> SEQ ID NO 156
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 156
cagacgcttc acgttcagac gcttcacgtt cagacgcttc acgttgagca cagacgttga      60
gagcacagac gttgagagca cagacgttga                                       90

<210> SEQ ID NO 157
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 157
tcaacgtctg tgctctcaac gtctgtgctc tcaacgtctg tgctcgcagc gtcttaacgt      60
gcagcgtctt aacgtgcagc gtcttaacgt                                       90

<210> SEQ ID NO 158
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 158
acgttaagac gctgcacgtt aagacgctgc acgttaagac gctgctgtct gcaacgtcag      60
tgtctgcaac gtcagtgtct gcaacgtcag                                       90

<210> SEQ ID NO 159
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 159
acgttaagac gctgcacgtt aagacgctgc acgttaagac gctgcagacg ttcaggacta      60
agacgttcag gactaagacg ttcaggacta                                       90

<210> SEQ ID NO 160
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 160
tagtcctgaa cgtcttagtc ctgaacgtct tagtcctgaa cgtcttgtct gcaacgtcag      60
tgtctgcaac gtcagtgtct gcaacgtcag                                       90

<210> SEQ ID NO 161
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 161
```

```
tagtcctgaa cgtcttagtc ctgaacgtct tagtcctgaa cgtctcacta gcaacgctag    60
cactagcaac gctagcacta gcaacgctag                                      90

<210> SEQ ID NO 162
<211> LENGTH: 90
<212> TYPE: DNA
<213> ORGANISM: Artificial
<220> FEATURE:
<223> OTHER INFORMATION: Synthetic Construct; Nucleic acid monomer

<400> SEQUENCE: 162
ctagcgtttg gacacctagc gtttggacac ctagcgtttg gacactgtct gcaacgtcag    60
tgtctgcaac gtcagtgtct gcaacgtcag                                      90

<210> SEQ ID NO 163
<211> LENGTH: 36
<212> TYPE: DNA
<213> ORGANISM: Artificial
<220> FEATURE:
<223> OTHER INFORMATION: Synthetic Construct; Nucleic acid monomer

<400> SEQUENCE: 163
aaaaaaaaaa aaaaaaaaaa aaaaaaaaaa aaaaaa                               36

<210> SEQ ID NO 164
<211> LENGTH: 12
<212> TYPE: DNA
<213> ORGANISM: Artificial
<220> FEATURE:
<223> OTHER INFORMATION: Synthetic Construct; Nucleic acid monomer

<400> SEQUENCE: 164
cgcgcgcgcg cg                                                         12

<210> SEQ ID NO 165
<211> LENGTH: 20
<212> TYPE: DNA
<213> ORGANISM: Artificial
<220> FEATURE:
<223> OTHER INFORMATION: Synthetic Construct; primer

<400> SEQUENCE: 165
gttctctggg aaatcgtgga                                                 20

<210> SEQ ID NO 166
<211> LENGTH: 20
<212> TYPE: DNA
<213> ORGANISM: Artificial
<220> FEATURE:
<223> OTHER INFORMATION: Synthetic Construct; primer

<400> SEQUENCE: 166
tgtactccag gtagctatgg                                                 20

<210> SEQ ID NO 167
<211> LENGTH: 21
<212> TYPE: DNA
```

```
<213> ORGANISM: Artificial
<220> FEATURE:
<223> OTHER INFORMATION: Synthetic Construct; primer

<400> SEQUENCE: 167
catccgtaaa gacctctatg c                                           21

<210> SEQ ID NO 168
<211> LENGTH: 19
<212> TYPE: DNA
<213> ORGANISM: Artificial
<220> FEATURE:
<223> OTHER INFORMATION: Synthetic Construct; primer

<400> SEQUENCE: 168
atggagccac cgatccaca                                              19

<210> SEQ ID NO 169
<211> LENGTH: 40
<212> TYPE: DNA
<213> ORGANISM: Artificial Sequence
<220> FEATURE:
<223> OTHER INFORMATION: Synthetic Construct; Nucleic acid monomer

<400> SEQUENCE: 169
acgttcgcgg gatttcccga catcacgttg acgctgtcga                       40

<210> SEQ ID NO 170
<211> LENGTH: 40
<212> TYPE: DNA
<213> ORGANISM: Artificial Sequence
<220> FEATURE:
<223> OTHER INFORMATION: Synthetic Construct; Nucleic acid monomer

<400> SEQUENCE: 170
acgttcgaca gcgtcaacgt gaaacgtgaa gcgtctgcga                       40

<210> SEQ ID NO 171
<211> LENGTH: 40
<212> TYPE: DNA
<213> ORGANISM: Artificial Sequence
<220> FEATURE:
<223> OTHER INFORMATION: Synthetic Construct; Nucleic acid monomer

<400> SEQUENCE: 171
acgttcgcag acgcttcacg ttgcagacag acgttgacgt                       40

<210> SEQ ID NO 172
<211> LENGTH: 40
<212> TYPE: DNA
<213> ORGANISM: Artificial Sequence
<220> FEATURE:
<223> OTHER INFORMATION: Synthetic Construct; Nucleic acid monomer

<400> SEQUENCE: 172
acgttcgtca acgtctgtct gctgtcggga aatcccgcga                       40

<210> SEQ ID NO 173
<211> LENGTH: 48
<212> TYPE: DNA
<213> ORGANISM: Artificial Sequence
<220> FEATURE:
<223> OTHER INFORMATION: Synthetic Construct; Nucleic acid monomer

<400> SEQUENCE: 173
aacgttcgtc aacgtctgtc tgctgtuuca uaucgaggcu gugucuuu              48
```

```
<210> SEQ ID NO 174
<211> LENGTH: 40
<212> TYPE: DNA
<213> ORGANISM: Artificial Sequence
<220> FEATURE:
<223> OTHER INFORMATION: Synthetic Construct; Nucleic acid monomer

<400> SEQUENCE: 174
gacacagccu cgauaugaaa catcacgttg acgctgtcga                            40
```